United States Patent
Zender et al.

(10) Patent No.: US 9,186,381 B2
(45) Date of Patent: Nov. 17, 2015

(54) MEDICAMENT FOR LIVER REGENERATION AND FOR TREATMENT OF LIVER FAILURE

(75) Inventors: Lars Zender, Braunschweig (DE); Torsten Wuestefeld, Braunschweig (DE)

(73) Assignees: Helmholtz Zentrum Fuer Infektionsforschung GmbH, Braunschweig (DE); Medizinische Hochschule Hannover, Hannover (DE)

( * ) Notice: Subject to any disclaimer, the term of this patent is extended or adjusted under 35 U.S.C. 154(b) by 0 days.

(21) Appl. No.: 14/009,738

(22) PCT Filed: Apr. 10, 2012

(86) PCT No.: PCT/EP2012/056481
§ 371 (c)(1),
(2), (4) Date: Dec. 23, 2013

(87) PCT Pub. No.: WO2012/136859
PCT Pub. Date: Oct. 11, 2012

(65) Prior Publication Data
US 2014/0141510 A1    May 22, 2014

Related U.S. Application Data

(60) Provisional application No. 61/473,015, filed on Apr. 7, 2011.

(30) Foreign Application Priority Data

Apr. 7, 2011  (EP) .................................... 11161588
May 24, 2011  (EP) .................................... 11167373

(51) Int. Cl.

| | | |
|---|---|---|
| *C12N 15/11* | (2006.01) | |
| *C12N 5/00* | (2006.01) | |
| *C12N 5/02* | (2006.01) | |
| *A61K 35/407* | (2015.01) | |
| *C12N 15/113* | (2010.01) | |
| *A61K 31/353* | (2006.01) | |
| *A61K 31/00* | (2006.01) | |
| *A61K 31/416* | (2006.01) | |
| *A61K 31/713* | (2006.01) | |
| *C07C 237/42* | (2006.01) | |
| *C07D 213/75* | (2006.01) | |
| *C07D 231/56* | (2006.01) | |

(52) U.S. Cl.
CPC .............. *A61K 35/407* (2013.01); *A61K 31/00* (2013.01); *A61K 31/353* (2013.01); *A61K 31/416* (2013.01); *A61K 31/713* (2013.01); *C07C 237/42* (2013.01); *C07D 213/75* (2013.01); *C07D 231/56* (2013.01); *C12N 15/1137* (2013.01); *C12Y 207/11024* (2013.01); *C12N 2310/14* (2013.01); *C12N 2310/141* (2013.01); *C12N 2310/531* (2013.01)

(58) Field of Classification Search
None
See application file for complete search history.

(56) References Cited

U.S. PATENT DOCUMENTS

| | | | |
|---|---|---|---|
| 7,569,575 B2 | 8/2009 | Sorensen et al. | |
| 2005/0059005 A1* | 3/2005 | Tuschl et al. | 435/6 |
| 2008/0145442 A1* | 6/2008 | Yarmush et al. | 424/520 |
| 2010/0074959 A1* | 3/2010 | Hansom et al. | 424/489 |

FOREIGN PATENT DOCUMENTS

| | | |
|---|---|---|
| EP | 1 506 784 | 2/2005 |
| WO | WO 98/39352 | 11/1998 |
| WO | WO 99/14226 | 3/1999 |
| WO | WO 2004/112824 | 12/2004 |
| WO | WO 2011/016829 | 2/2011 |
| WO | WO 2011/032981 | 3/2011 |

OTHER PUBLICATIONS

Sales et al., "Genistein decreases liver fibrosis and cholestasis induced by prolonged biliary obstruction in the rat," Annals of Hepatology 2007;6(1)January-March:41-47.*
Abalea et al, "Repair of iron-induced DNA oxidation by the flavanoid myricetin in primary rat hepatocyte cultures," Free Radical Biology and Medicine, vol. 26, Nos. 11/12, pp. 1457-1466 (1999).*
Kuzu, Nalan, et al., "Protective Role of Genistein in Acute Liver Damage Induced by Carbon Tetrachloride, Mediators of Inflammation", vol. 22, No. 9, Jan. 1, 2007, 6 pages.
Marasa, Bernard, S., et al., "Increased MKK4 Abundance with Replicative Senescence in Linked to the Joint Reduction of Multiple MicroRNAs", Science Signaling, vol. 2, No. 94, Oct. 27, 2009, pp. ra69-1-ra69-8.
Takamura, Masaaki, et al., "An inhibitor of c-Jun NH2-terminal kinase, SP600125, protects mice from D-galactosamine/lipopolysaccharide-induced hepatic failure by modulating BH3-only proteins", Life Sciences, vol. 80, No. 14, Mar. 1, 2007, pp. 1335-1344.
European Office Action Dated Mar. 17, 2015.

* cited by examiner

*Primary Examiner* — Craig Ricci
*Assistant Examiner* — Jared D Barsky
(74) *Attorney, Agent, or Firm* — Greer, Burns & Crain, Ltd.

(57) ABSTRACT

The present invention relates to the use of a compound which inhibits the activity of MKK4 as a medicament for the treatment of a patient suffering from an impaired liver function, to the use of a compound as a medicament for the treatment of liver failure, including acute/fulminant or chronic liver failure and/or for increasing the regeneration of liver tissue in a patient.

3 Claims, 8 Drawing Sheets

Figure 1:
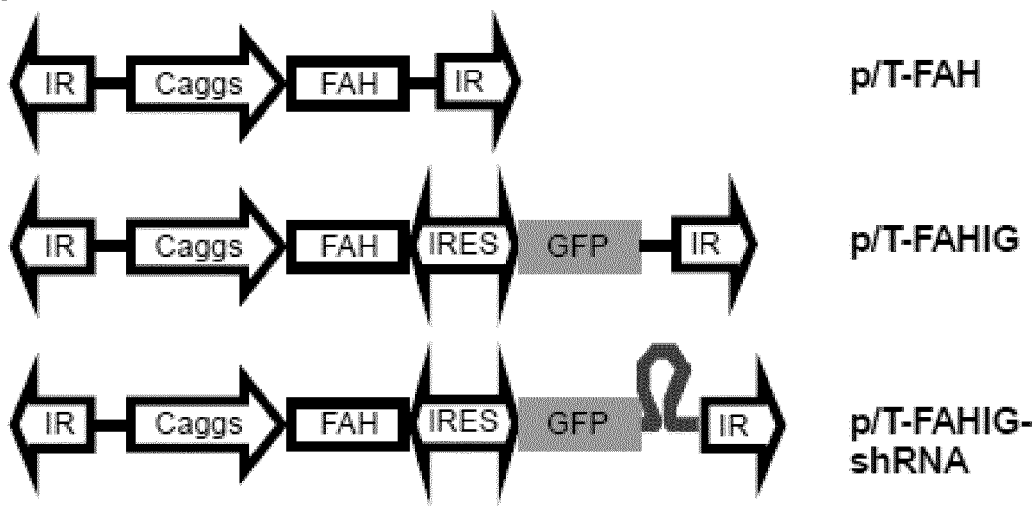

FAHIG-shCtr          FAHIG-          FAHIG-
                    shMKK4-A        shMKK4-B

MEDICAMENT FOR LIVER REGENERATION AND FOR TREATMENT OF LIVER FAILURE

The present invention relates to the use of a compound as a medicament for the treatment of a patient suffering from an impaired liver function, to the use of a compound as a medicament for the treatment of liver failure, including acute/fulminant or chronic liver failure and/or for increasing the regeneration of liver tissue in a patient. Also, the invention relates to the use of the compound to increase the robustness and regeneration of cultured hepatocytes in vitro to improve cell based therapies, e.g. to a process for cultivating hepatocytes in the presence of the compound, including the use of the cultivated hepatocytes as a transplant, and for hepatocyte transplantation, respectively, into a patient suffering from liver failure. Further, the invention relates to the use of the compound for the production of the medicament, and to the use of hepatocytes cultured in vitro in the presence of the compound for the production of a hepatocyte transplant.

Further, the invention relates to a bio-artificial liver comprising cultivated hepatocytes which contain or are contacted by the compound which can be used as a medicament. Further, the invention relates to a process for producing hepatocytes which comprise the compound used as a medicament, and to the use of cultivated hepatocytes being contacted by the medicament for use as a medicament in the treatment of a functionally impaired liver, for the treatment of liver failure, and/or for supporting liver regeneration. Liver failure which can be treated according to the invention includes acute and/or fulminant hepatitis due to infection with hepatotropic viruses, alcohol abuse, obesity, genetic diseases like Wilson's disease, hemochromatosis, alpha1-antitrypsin deficiency and related conditions. Liver failure which can be treated according to invention also includes all forms of chronic liver failure with liver cirrhosis induced by e.g. the causes as indicated above.

STATE OF THE ART

To-date, liver failure is treated by transplantation of a donor liver, however there is a severe shortage of donor organs.

WO98/39352, WO99/14226, and U.S. Pat. No. 7,569,575 B2 describe use and synthesis of locked nucleic acids (LNA).

OBJECTS OF THE INVENTION

It is an object of the invention to provide a medicament suitable for the treatment of insufficient liver function, e.g. liver failure, and to provide cultivated hepatocytes, which can be kept in culture for use in a bio-artificial liver, e.g. for use in the purification of blood or for transplantation into patients with impaired liver function.

GENERAL DESCRIPTION OF THE INVENTION

The invention achieves the objects by the features of the claims, and especially by providing a compound inhibiting or inactivating the mitogen-activated protein kinase kinase 4 (MAP2K4, also termed MKK4). The nucleotide sequence of the mRNA encoding human MKK4 according to accession No. NM_003010 is given as SEQ ID NO: 1204. Inhibition or inactivation of the activity of MKK4 can be by reduction of the expression of MKK4, e.g. by RNA interference induced by siRNA, especially shRNA or microRNA hybridizing to the mRNA encoding MKK4, or by inhibition of MKK4 present in a hepatocyte, e.g. by a kinase-specific inhibitor compound like SP600125, myricitine, Genistein, and PD98059.

The invention is based on the finding that the reduction or deletion of active MKK4 in hepatocytes, which can be both cultivated hepatocytes in vitro and hepatocytes of a liver of an animal or human patient, results in increased regeneration of hepatocytes, e.g. in extended cultivation periods and in an increase of regeneration of a damaged or impaired liver in vivo, e.g. in experimental animals after induction of an experimental liver failure representing liver failure in a human patient. It has been found that the reduction or deletion of active MKK4 in hepatocytes can result in an increased proliferative capacity due to an earlier cell cycle entry and in an increased resistance against apoptosis. In summary, contacting hepatocytes in vivo by the compound inhibiting or inactivating MKK4 results in an increased survival of mice in experimental models of liver failure. Further, contacting cultured hepatocytes in vitro by the compound inhibiting or inactivating MKK4 results in extended cultivation periods and in production of cultivated hepatocytes, which can be used as a medicament, e.g. as a transplant, or which can be used as part of a device for the continuous purification of blood withdrawn from and returned to a patient.

Inactivation or deletion of MKK4 can be obtained by preventing the expression of functional MKK4 in liver cells, e.g. by inactivating the endogenous gene encoding MKK4, e.g. by insertional mutagenesis of the endogenous gene encoding MKK4, e.g. by inserting a nucleotide sequence comprising at least one nucleotide, for disruption of the endogenous gene encoding MKK4, by preventing translation of the mRNA encoding MKK4, or by pharmacological means, e.g. by contacting hepatocytes in vivo or in vitro by a compound which inhibits the kinase function of MKK4.

Preferably, inactivation of MKK4 is obtained by reduction or prevention of expression of MKK4 by administration of an inhibitory RNA through RNA interference (RNAi), which is e.g. an oligonucleotide hybridizing to the mRNA encoding MKK4, which inhibitory RNA can e.g. be an siRNA, an shRNA or any form of shRNA contained in a microRNA, e.g. a microRNA based shRNA, an antisense oligonucleotide, or a mixture of these. Preferably, the oligonucleotide hybridizing to the mRNA encoding MKK4 comprises or consists of 19, 21 or 22 nucleotides which are complementary, especially under physiological and cellular conditions, to the mRNA sequence encoding MKK4, and a second section, e.g. an antisense strand, which is complementary in sequence to the first section. From such a double-stranded siRNA molecule, in a cellular environment, the first section is released from the second section and binds to the mRNA encoding MKK4 to induce the degradation of this mRNA or to induce inhibition of translation. Double stranded RNA molecules (siRNAs) which later release one section for mRNA targeting can be directly delivered into livers or liver cells but can also be contained in shRNAs or miRNAs from which the double stranded RNA is later released by enzymatic processing through the cellular RNAi machinery. The sequence of the oligonucleotide hybridising to the mRNA encoding MKK4 to induce its degradation or to prevent its translation can be 100% complementary in sequence as usually is the case with siRNAs or shRNAs, but also can contain mismatches as is often the case with endogenous miRNA, e.g. endogenous miR-15b, miR-24, miR-25, and miR-141, which are also included as compounds for use in the invention, can target MKK4 mRNA with being only partially complementary in sequence. In the description, exemplary oligonucleotide sequences which are hybridizing to the mRNA encoding MKK4 are given, which oligonucleotides can be contained in an siRNA, e.g. as a first section, preferably forming a double-strand with a reverse complementary second section contained in the siRNA.

It has been found that inactivation of MKK4 activity, preferably by reduction or inhibition of the expression of MKK4 by presence of an oligonucleotide hybridizing to the mRNA encoding MKK4, can be obtained by contacting hepatocytes in vivo or in vitro with at least one oligonucleotide specifically hybridizing to the mRNA encoding MKK4. Contacting in hepatocytes the mRNA which encodes MKK4 can be obtained by administrating to a human or animal patient the RNA hybridizing to the mRNA encoding MKK4 using RNAi through siRNAs by transient in vivo transfection of the siRNA, or alternatively by using, e.g. as a medicament, any means of stable delivery of siRNA, e.g. shRNA, especially microRNA based shRNA or antisense oligonucleotides which are hybridizing to the mRNA encoding MKK4, e.g. use of a viral or transposon-based nucleic acid construct which contains an expression cassette encoding the shRNA, for transcription of the shRNA from the expression cassette. The siRNA, or the nucleic acid construct containing an expression cassette encoding the siRNA, is used as a medicament. The nucleic acid construct can e.g. be a viral vector or a transposon-containing nucleic acid construct additionally encoding transposase for integrative stable transduction.

Generally, an oligonucleotide hybridizing to the mRNA encoding MKK4 for reducing or preventing the expression of MKK4 in a liver cell is an oligonucleotide having a sequence hybridizing to the mRNA encoding MKK4, especially hybridizing to SEQ ID NO: 1204, under physiological conditions, e.g. in the cellular environment of a liver cell. The sequence can be fully complementary, i.e. be reverse complementary to a section of the mRNA of SEQ ID NO: 1204, or the sequence can have mismatches as it often occurs in microRNA mediated inhibition of translation, e.g. the oligonucleotide sequence has a nucleotide sequence of at least 80%, preferably of at least 85%, more preferably of at least 90% or of 95% identity to a reverse complementary section of SEQ ID NO: 1204, including as examples the endogenous miRNAs miR-15b, miR-24, miR-25, and miR-141.

Preferred inhibitory oligonucleotides, e.g. shRNA, comprise or consist of one or more of the following oligonucleotides: SEQ ID NO: 1 to SEQ ID NO: 1203. For the design of these sequences the DSIR tool for siRNA and shRNA target design (BMC Bioinformatics. 2006 Nov. 30; 7(1):520.) with a score threshold of 70 was used, and therefore all SEQ ID NO: 1 to 1203 have score of at least 70. Inhibitory oligonucleotide sequences, and groups of inhibitory oligonucleotide sequences having higher scores are preferred. The sequences are given in an order of descending score value, e.g. SEQ ID NO: 1 has the highest score (107.1), and SEQ ID NO: 1200, SEQ ID NO: 1201, SEQ ID NO: 1202, and SEQ ID NO: 1203 have the lowest score (70.0 each). SEQ ID NO: 1 to SEQ ID NO: 11 have a score of at least 100, SEQ ID NO: 12 to SEQ ID NO: 55 have a score of at least 95.1, e.g. of 99.8 to 95.1, SEQ ID NO: 56 to SEQ ID NO: 136 have a score of at least 90.0, e.g. of 94.8 to 90.0, SEQ ID NO: 137 to SEQ ID NO: 317 have a score of at least 85, e.g. of 89.9 to 85.0, SEQ ID NO: 318 to SEQ ID NO: 593 have a score of at least 80, e.g. of 84.9 to 80.0, SEQ ID NO: 594 to SEQ ID NO: 915 have a score of at least 75.0, e.g. of 79.9 to 75.0, and SEQ ID NO: 916 to SEQ ID NO: 1203 have a score between 74.9 and 70.0. Further, shRNA or microRNA molecules can comprise one of these oligonucleotides which are complementary to the mRNA encoding MKK4, e.g. comprising one of these oligonucleotides as a first section and a complementary second section in the siRNA as hybridizing sections in a microRNA.

The oligonucleotides hybridizing to the mRNA encoding MKK4 for use as a medicament for the regeneration of liver tissue, or for the treatment of liver failure, liver insufficiency and/or liver cirrhosis, can preferably be in the form of RNA, DNA, or hybrids of DNA and RNA, peptide-linkage nucleic acids (PNA), and nucleic acid derivatives containing a ribose moiety with substituents bridging the 2'-carbon atom and the 4'-carbon atom, e.g. by an oxymethylene group or an aminomethylene group, which derivatives are termed locked nucleic acids (LNA), including further derivatives of the phosphate-sugar backbone, single-stranded, preferably double-stranded, which by intracellular processing by the RNAi enzymatic machinery release a single stranded oligonucleotide for hybridization to the mRNA encoding MKK4.

In the alternative to consisting of the use of a nucleic acid sequence hybridizing to the mRNA encoding MKK4, e.g. for direct use as a medicament, the inhibitory RNA can be contained as a coding sequence under the control of a promoter in an expression cassette. Depending on the promoter, which can be a constitutive or an inducible promoter, upon introduction into the hepatocyte the inhibitory RNA is produced by transcription.

For introduction of nucleic acid constructs reducing or deleting the expression of active MKK4, e.g. nucleic acid constructs which interrupt the endogenous gene encoding MKK4 of a hepatocyte or inhibitory RNA hybridizing to the mRNA encoding MKK4, the nucleic acid constructs are preferably provided in the form of one or more oligonucleotides in a pharmaceutically acceptable carrier formulation or in the form of a viral vector packaged in a viral particle or in a virus-like particle. A viral vector can be a retroviral, a lentiviral vector, an adeno-associated viral vector, or adenoviral vector.

A formulation of the compounds or compositions of the invention for inhibiting or inactivating MKK4 in a pharmaceutically acceptable carrier can e.g. be in a formulation of lipid nanoparticles (LNP) (as e.g. available from Alnylam Pharmaceuticals, USA), a liposome formulation, and/or in a formulation containing a combination with at least one transfection enhancing agent, e.g. lipofectamine and/or as a Calcium complex.

In the alternative or in addition to an oligonucleotide having a sequence hybridizing to the mRNA encoding MKK4, e.g. an RNAi hybridizing to the mRNA encoding MKK4, agents inactivating the activity of MKK4, e.g. agents blocking the function of MKK4 protein, can be used as compounds for use as a medicament according to the invention. Exemplary compounds suitable for inactivating MKK4 are e.g. SP600125, myricitine, Genistein, and PD98059, especially for use as medicaments for the treatment of liver failure, and for the regeneration of liver tissue, respectively.

Histologic analysis of mouse livers with stable knock down of MKK4, experimentally generated by transfection with a nucleic acid construct containing an expression cassette for shRNA hybridizing to the mRNA encoding MKK4 showed normal histology. Further, no increase in neoplasms was detected in the experimental animals, indicating that deletion of MKK4 does not augment the risk of cancer development.

DETAILED DESCRIPTION OF THE INVENTION

Figure 2:
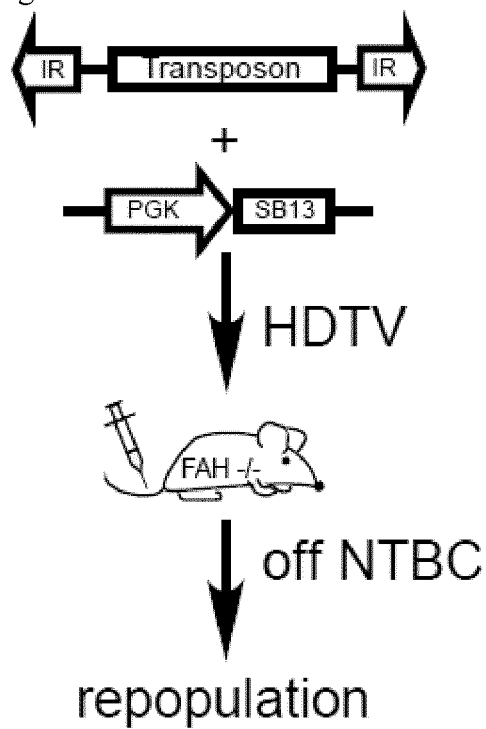
Figure 3:
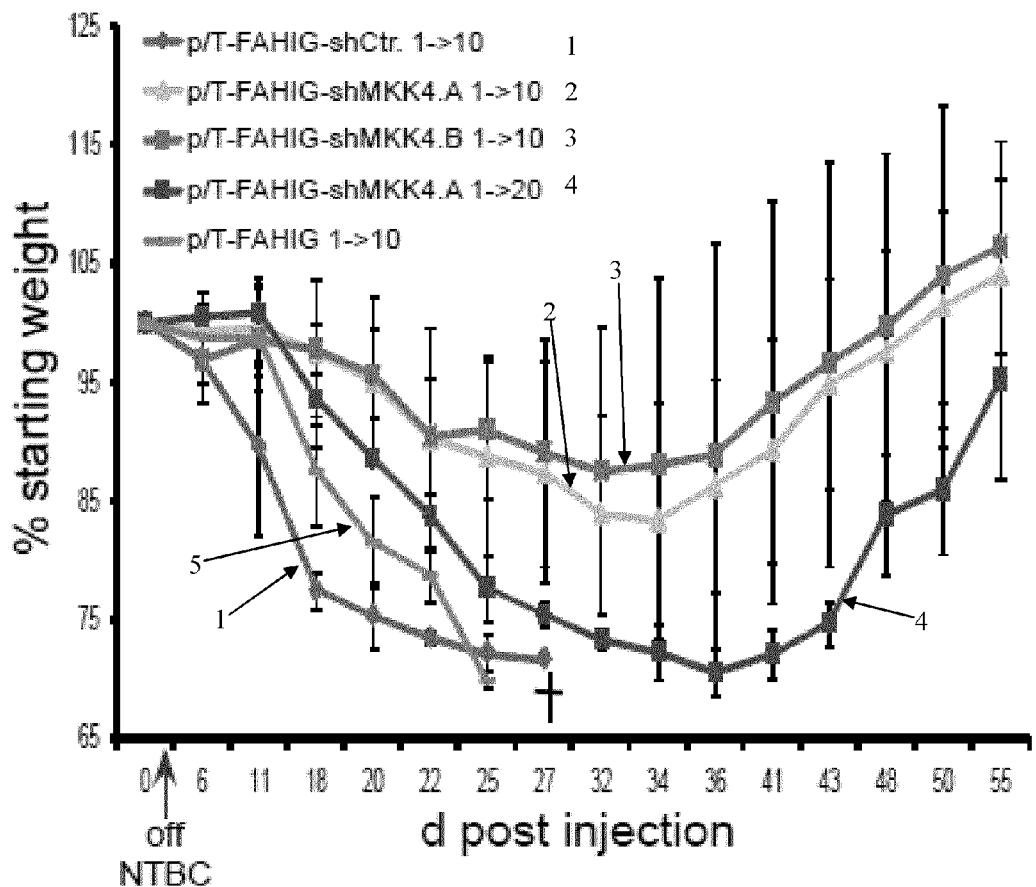
Figure 4:
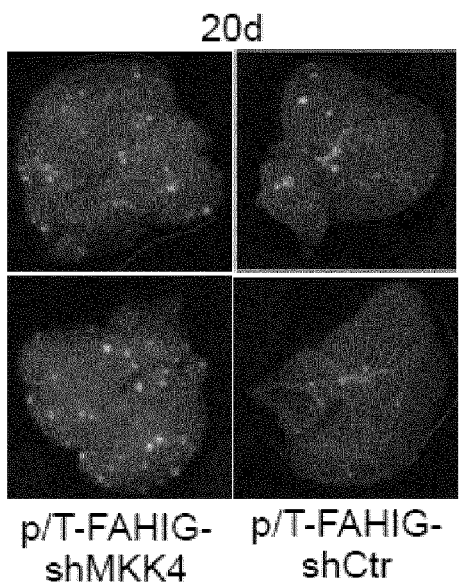
Figure 5:
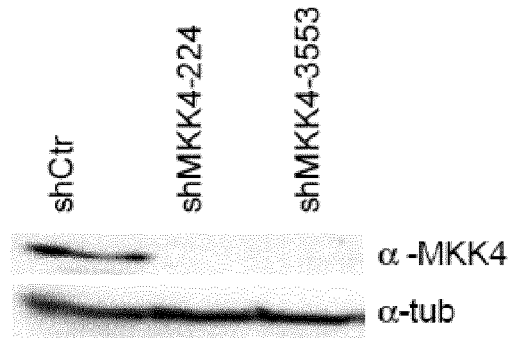
Figure 6:
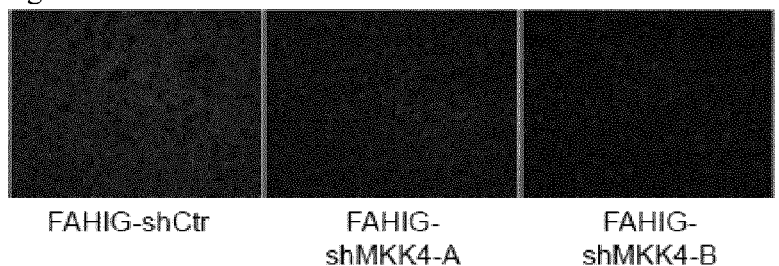
Figure 7:
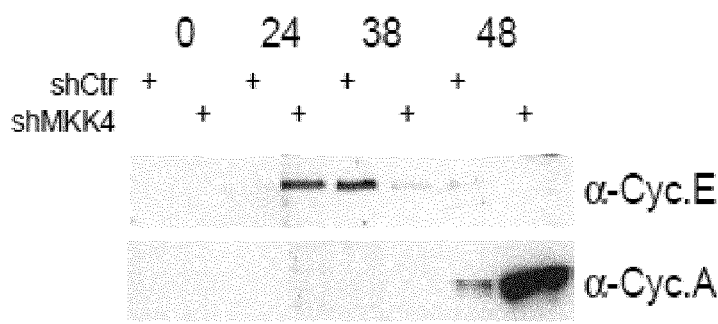
Figure 8:
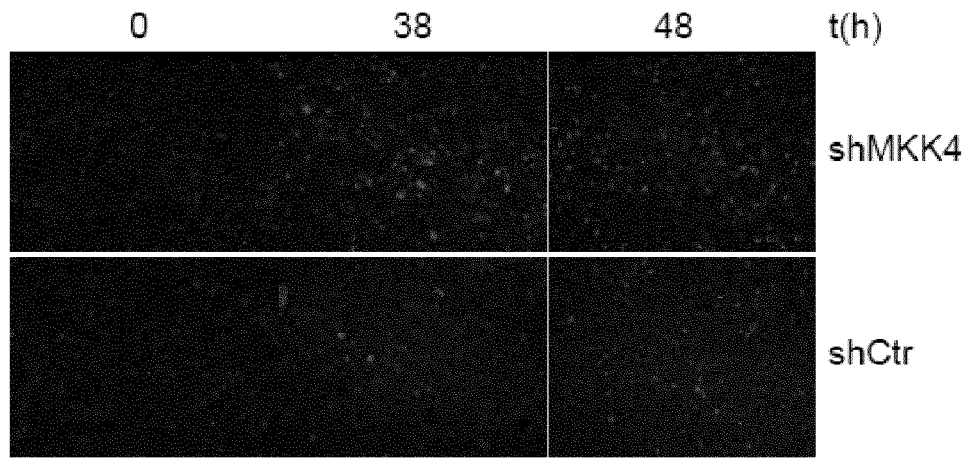
Figure 9:
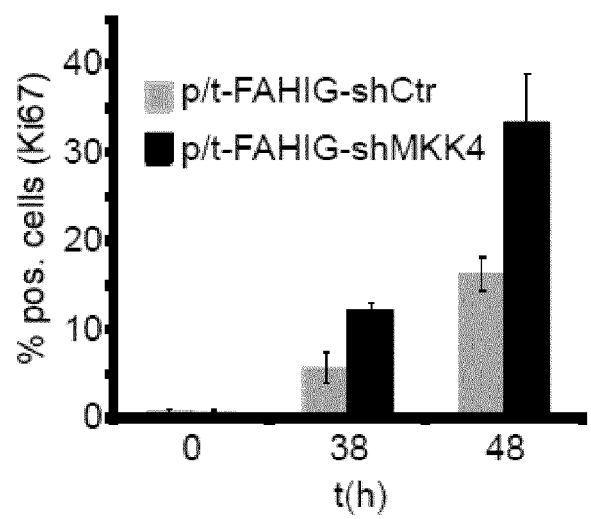
Figure 10:
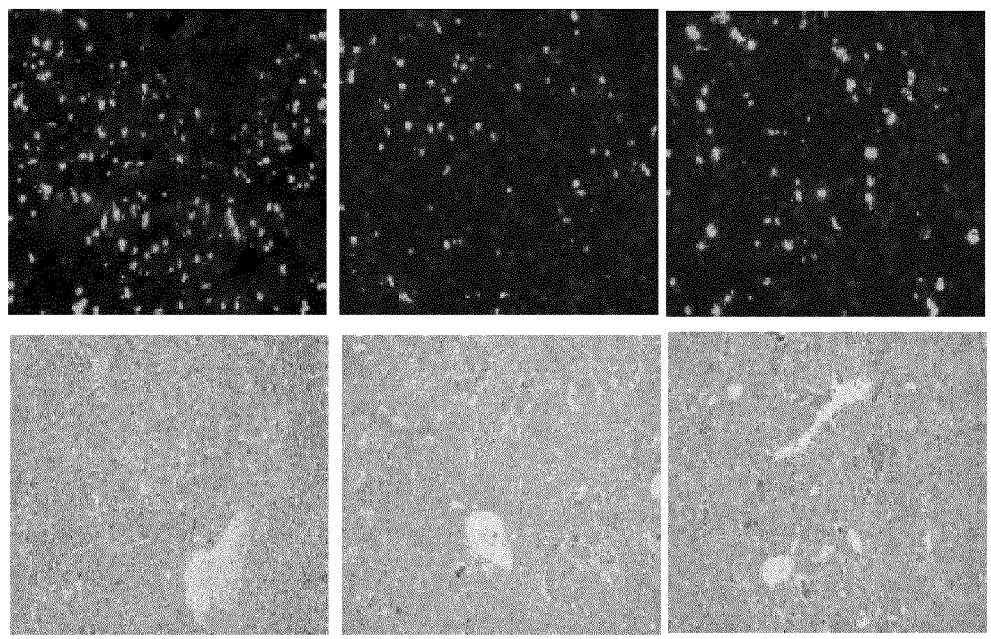
Figure 11:
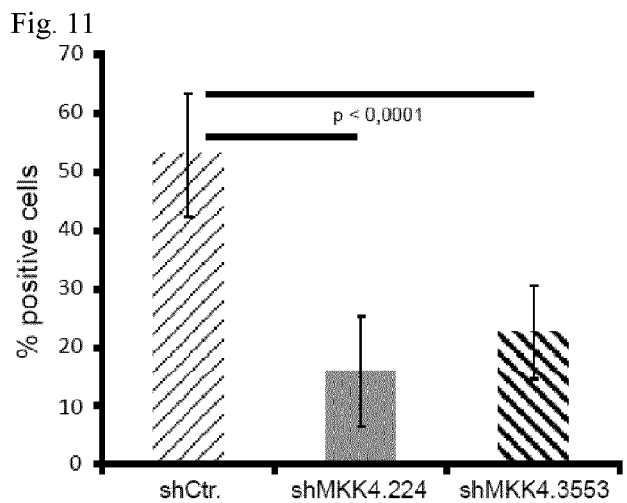
Figure 12:
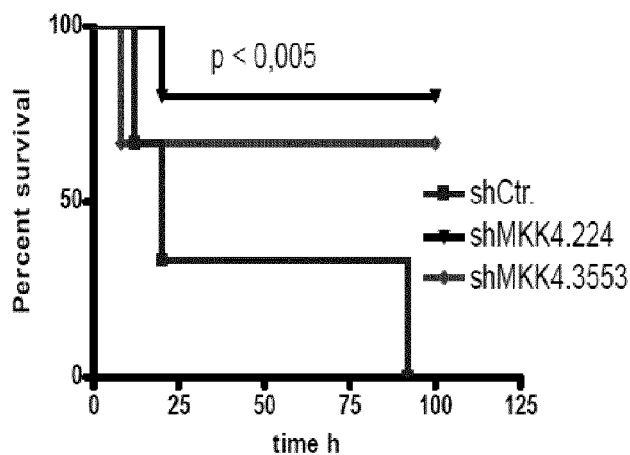
Figure 13:
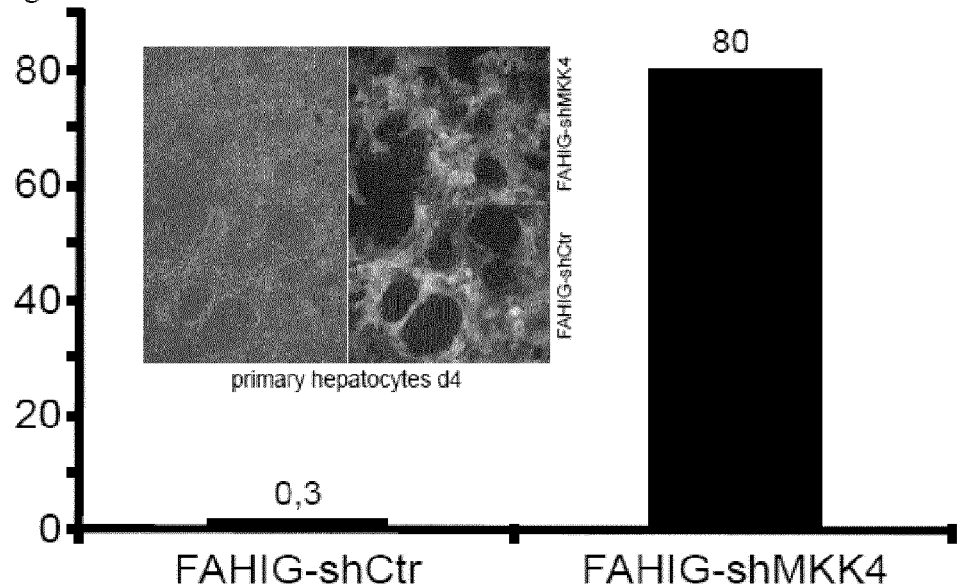
Figure 14:
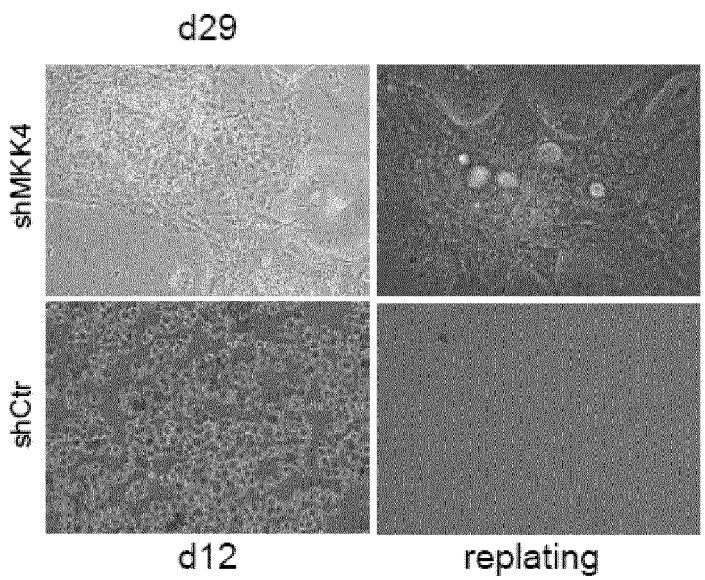
Figure 15:
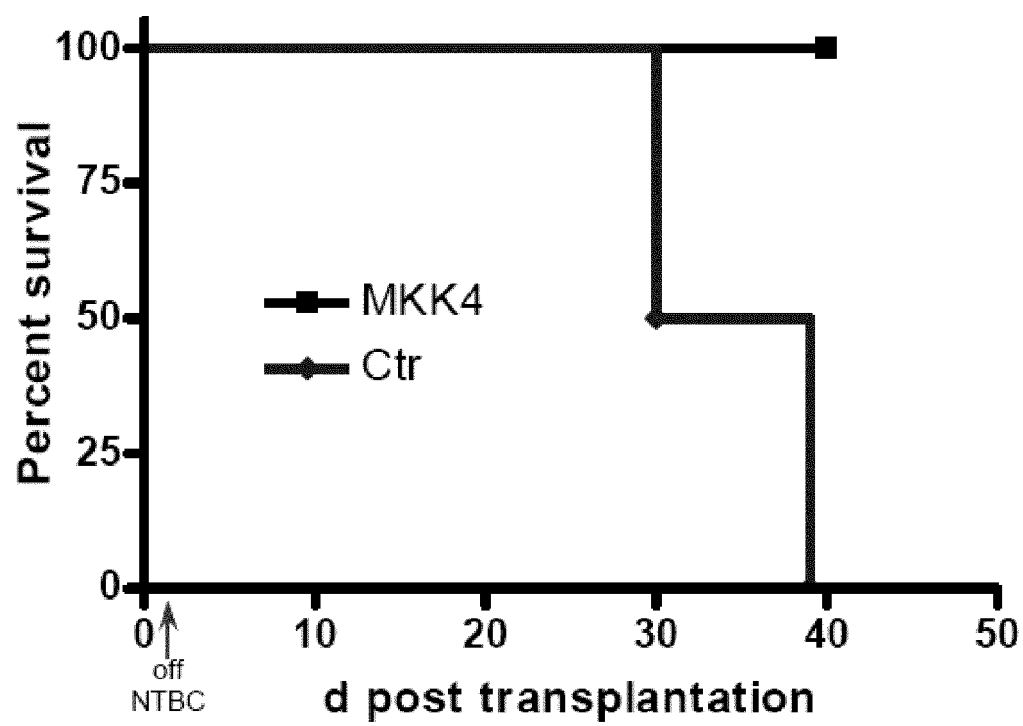
Figure 16:
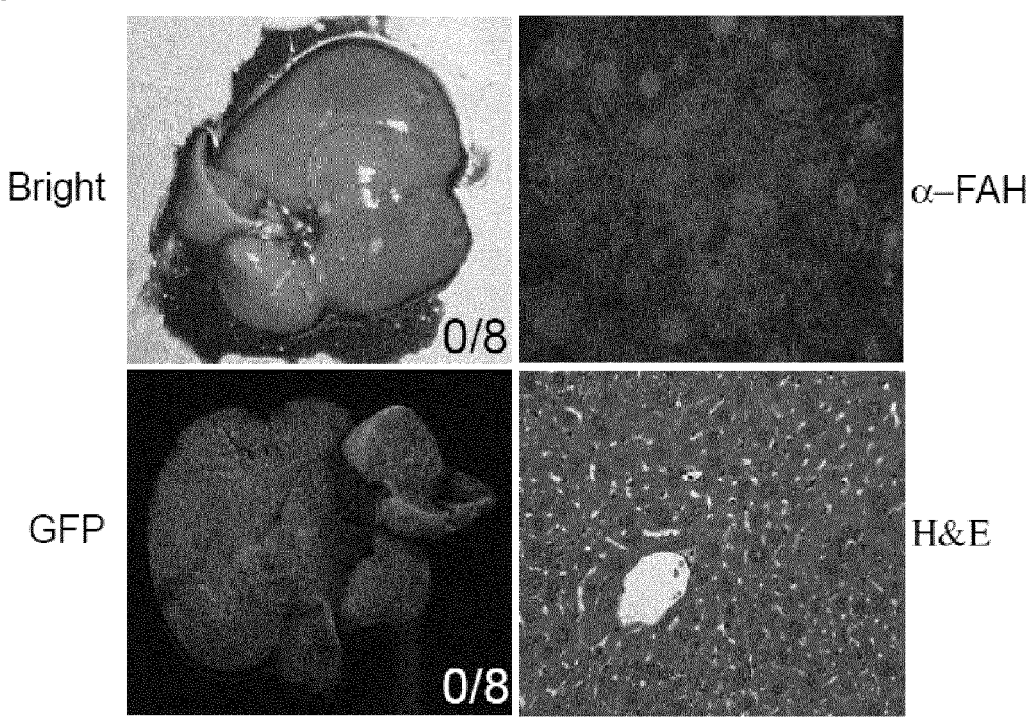
Figure 17:
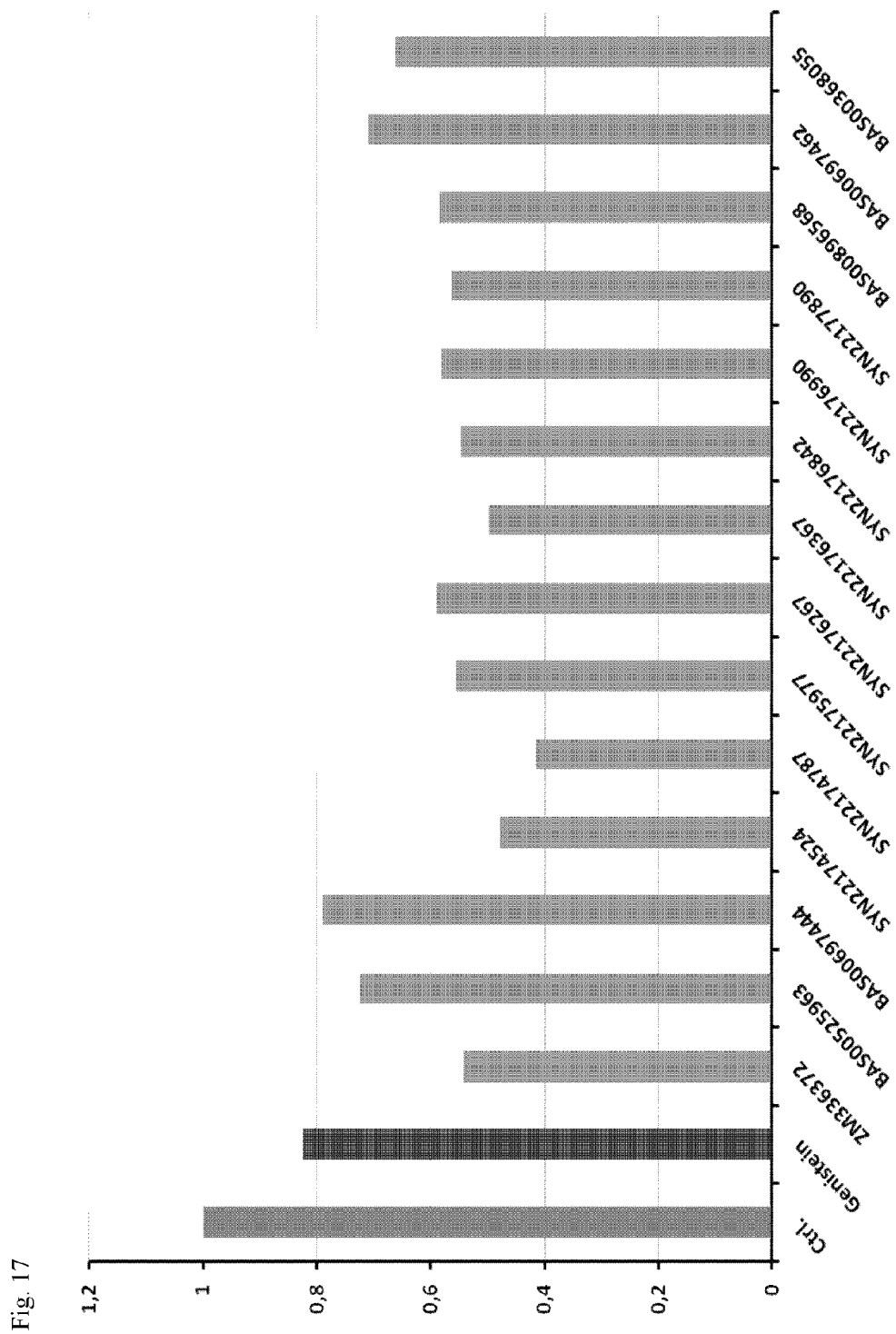

The invention is now described in greater detail by way of examples with reference to the figures, which show in FIG. 1 schematic representations of nucleic acid constructs for producing inhibitory RNA, FIG. 2 a schematic representation of a transposase mediated intrahepatic transfer of an expression cassette encoding an inhibitory RNA (micro RNA based shRNA) of the invention, FIG. 3 the time course of the body weight of mice after stable transposon mediated intrahepatic transfer of an expression cassette for inhibitory RNA and controls, whereas an increase in body weight correlates with an increase in liver repopulation with the construct, FIG. 4 GFP-imaging of explanted mouse livers in the process of repopulation by hepatocytes stably expressing shRNA specific for inactivating MKK4, FIG. 5 a Western blot specific for MKK4 of liver samples of mice stably transfected with an expression cassette encoding shRNA specific for inactivating MKK4, FIG. 6 immunofluorescence analysis of the livers of mice stably transfected with an expression cassette encoding shRNA specific for inactivating MKK4, FIG. 7 a Western blot for cyclin A and E of nuclear liver extracts of transfected mouse livers in the indicated time course after partial hepatectomy indicating earlier cell cycle entry of hepatocytes stably expressing shRNA specific for MKK4, FIG. 8 a Ki67 staining of mouse livers expressing shRNA specific for MKK4 or control shRNA at the indicated time points after partial hepatectomy, FIG. 9 a quantifying graph of Ki67 positive hepatocytes depicted in FIG. 8, FIG. 10 TUNEL (upper panel) and H&E staining (lower panel) on liver sections after induction of an acute/fulminant liver failure in control shRNA transfected hepatocytes in comparison to hepatocytes expressing an shRNA specific for RNA of MKK4, which are protected, FIG. 11 a quantifying graph of apoptotic hepatocytes according to TUNEL staining as depicted in FIG. 10, FIG. 12 a survival curve of mice expressing the shRNA inactivating MKK4 (shMKK4) compared to control mice (shCtr.) after induction of liver failure, FIG. 13 a quantifying graph of EdU incorporation into cultured murine hepatocytes with inactivated MKK4 activity (FAHIG-shMKK4) and control hepatocytes (FAHIG-shCtr) with an inset showing phase contrast micrographs of these hepatocytes, FIG. 14 phase contrast micrographs of cultured hepatocytes with inactivated MKK4 (shMKK4) at day 29 (d29) and of control hepatocytes (shCtr) at day 12 (d12), and at day 3 of hepatocytes replated at day 15 (replating), FIG. 15 a survival curve of FAH −/− mice after transplantation of hepatocytes kept one week in culture expressing shRNA specifically inactivating MKK4 or a control shRNA, FIG. 16 photographs, GFP-imaging, α-FAH immunostaining and H&E staining of liver of mice aged for 1 year following transplantation of hepatocytes stably expressing shRNA specifically inactivating MKK4, and in FIG. 17 an overview of the inhibitory effect of preferred small inhibitory compounds.

Using mice and murine liver tissue and hepatocytes as examples, especially representing human patients and human liver tissue and human hepatocytes, respectively, it was found that liver regeneration could be increased by inactivating MKK4 activity, both in vivo and in cultured hepatocytes. Mice harbouring livers with reduced MKK4 activity show increased regenerative capacity under conditions of liver failure, which also resulted in an increased survival. Inactivation of MKK4 activity could efficiently be achieved by inhibitory RNA present in hepatocytes, in vivo and in vitro, which inhibitory RNA could be generated by transcription from a stably or transiently transfected nucleic acid construct containing an expression cassette encoding at least one RNA which under physiological conditions hybridizes to the mRNA of MKK4.

Alternatively, the inhibitory RNA could be introduced, e.g. transfected into hepatocytes in vivo and in culture, e.g. in the form of an siRNA, shRNA or microRNA, preferably in a suitable formulation, e.g. formulated as a liposome preparation or a lipid nanoparticle preparation. In the alternative to the use of inhibitory RNA for use as a medicament for the treatment of liver and hepatocytes, SP600125, myricitine, Genistein, PD98059, 3-(Dimethylamino)-N-[3-[(4-hydroxybenzoyl)-amino]-4-methylphenyl]benzamide (ZM 336372), 2-hydroxy-1-methyl-4-oxo-N-pyridin-4-ylquinoline-3-carboxamide (BAS00525963), 2-(1H-indazol-5-yliminomethyl)-6-nitrophenolate (BAS00697444), 5-[2-(3,5-dimethyl-1H-pyrazol-4-yl)ethyl]-7-oxo-N-phenyl-1H-pyrazolo[1,5-a]pyrimidine-3-carboxamide (SYN22174524), 5-[2-(3,5-dimethyl-1H-pyrazol-4-yl)ethyl]-3-(4-fluorophenyl)-1H-pyrazolo[1,5-a]pyrimidin-7-one (SYN22174787), 5-[2-(3,5-dimethyl-1H-pyrazol-4-yl)ethyl]-3-(4-methylphenyl)-1H-pyrazolo[1,5-a]pyrimidin-7-one (SYN22175977), 3-(4-chlorophenyl)-5-[2-(3,5-dimethyl-1H-pyrazol-4-yl)ethyl]-2-(methoxymethyl)-1H-pyrazolo[1,5-a]pyrimidin-7-one (SYN22176267), -[2-(3,5-dimethyl-1H-pyrazol-4-yl)ethyl]-2-(methoxymethyl)-3-(4-methylphenyl)-1H-pyrazolo[1,5-a]pyrimidin-7-one (SYN22176367), 5-[2-(3,5-dimethyl-1H-pyrazol-4-yl)ethyl]-2-(3-methoxyphenyl)-3-methyl-pyrazolo[5,1-b]pyrimidin-7-ol (SYN22176842), 5-[2-(3,5-dimethyl-1H-pyrazol-4-yl)ethyl]-2-(2-methoxyphenyl)-3-methyl-pyrazolo[5,1-b]pyrimidin-7-ol (SYN22176990), 3-(4-chlorophenyl)-5-[2-(3,5-dimethyl-1H-pyrazol-4-yl)ethyl]-2-methyl-1H-pyrazolo[1,5-a]pyrimidin-7-one (SYN22177890), 5-amino-3-[(Z)-1-cyano-2-[3-[(4-methoxy-6-piperidin-1-yl-1,3,5-triazin-2-yl)oxy]phenyl]ethenyl]-1-(2-hydroxyethyl)pyrazole-4-carbonitrile (BAS00896568), 2-(1H-indazol-5-yliminomethyl)-6-methoxy-4-nitrophenolate (BAS00697462), 7-oxobenzo[e]perimidine-4-carboxylic acid (BAS00368055), the further compounds contained in Table 1 given herein, and combinations thereof could be used as medicaments, the presence of which inactivated MKK4 activity at least partially, also resulting in an increase of hepatocyte proliferation, protection against induced apoptosis, and restoration of liver function. These compounds having specific inhibitory activity against MKK4 are also collectively referred to as small inhibitory compounds. Accordingly, both the inhibitory RNA having specificity for the RNA encoding MKK4 and the small inhibitory compounds having specificity for MKK4 protein each inhibit MKK4 and are therefore used as medicaments in the treatment of liver failure and/or for the protection of hepatocytes against apoptosis and/or for the regeneration of hepatocytes. The small inhibitory compounds can be formulated in a pharmaceutically acceptable formulation, comprising e.g. buffer substance and carrier substance as well as formulation additives as known to the pharmacist, e.g. for i.v., i.m., intra-liver administration or oral administration.

During functional in vitro testing of hepatocytes containing nucleic acid constructs with stable expression of FAH, GFP and shRNA, hepatocytes were isolated from mouse livers and cultivated. It was found that only hepatocytes which were transfected with an expression cassette encoding an inhibitory RNA targeting, i.e. specifically hybridizing with, the mRNA encoding MKK4 could be cultivated for extended periods, e.g. for over 30 days. In addition, these hepatocytes could be trypsinized and replated according to standard methods. Transplantation of primary hepatocytes expressing the shRNA against MKK4 after 1 week in culture into FAH knock-out mice showed the capacity of the hepatocytes in which MKK4 was inactivated to repopulate the liver of these mice and allow survival. In contrast, this result could not be obtained by primary hepatocytes expressing the non-specific control shRNA. This result also indicates that primary hepatocytes expressing the shRNA against MKK4 do not undergo major dedifferentiation during the time of culture.

Example 1

Inactivation of MKK4 by Transcription of Inhibitory RNA from an Expression Cassette Integrated into Liver Tissue The introduction of inhibitory RNA into hepatocytes, i.e. into the liver of a patient, for inactivating MKK4 in vivo by expression of the inhibitory RNA from a nucleic acid construct encoding the inhibitory RNA in an expression cassette is shown on the example of mice (C57BL/6) using an expression cassette encoding the inhibitory RNA for production of the shRNA hybridizing to the mRNA encoding MKK4. The promoter controlling transcription of the inhibitory RNA was constitutive.

In short, homozygous FAH-negative mice (FAH −/−) were kept with constant administration of NTBC in order to block the 4-hydroxyphenylpyruvate dioxygenase which would otherwise lead to the accumulation of toxic metabolites in the liver. As inhibitory RNA, SEQ ID NO: 1 or, alternatively, SEQ ID NO: 2 was used, both of which hybridize with the mRNA encoding MKK4. Each inhibitory RNA was introduced by contacting the liver cells in vivo with nucleic acid constructs with transposase-specific inverted repeat sections (IR) on both termini, containing an expression cassette for FAH for complementation of the FAH −/− genotype upon expression, by hydrodynamic tail vein injection in combination with a second nucleic acid construct encoding transposase sleeping beauty 13 (SB 13) under the control of the PGK promoter.

The nucleic acid constructs are shown in FIG. 1. FIG. 2 schematically shows the steps of the genetic manipulation. A first control construct p/T-FAHIG contains the complementing FAH expression cassette and a green fluorescent protein (GFP) expression cassette comprising the GFP encoding sequence under the control of an IRES element, but encodes no inhibitory RNA. A sequence encoding an inhibitory RNA with no target as a control, which in addition to the GFP expression cassette in 3' to the GFP encoding sequence encodes a microRNA was contained in the construct p/T-FAHIG-shCtr. A sequence encoding an inhibitory RNA according to the invention was contained in construct p/T-FAHIG-shMKK4, which in addition to the GFP expression cassette in 3' to the GFP encoding sequence encodes a microRNA (depicted as a loop) comprising an shRNA as an example for an inhibitory RNA. In the example, SEQ ID NO: 1, alternatively SEQ ID NO: 2 was used as a preferred representative of inhibitory RNA sequences. Following introduction of the nucleic acid constructs, mice were kept in the absence of NTBC for selecting animals having complemented hepatocytes. In cotransfected cells, the transient expression of SB13 leads to the stable integration of the expression cassette in the genome.

Analyses of mice after introduction of the nucleic acid constructs confirmed stable transcription of the inhibitory RNA from the nucleic acid construct. In detail, analysis of body weight of mice of FIG. 3 shows that the animals having received the control construct p/T-FAHIG (5) as well as the animals having received the control construct p/T-FAHIG-shCtr. (1), which expresses a non-specific RNA could not reconstitute liver function effectively but died.

Animals of those groups having received a nucleic acid construct containing an expression cassette for an inhibitory RNA which is specific for SEQ ID NO: 1, namely p/T-FAHIG-shMKK4.A (2, 4) and p/T-FAHIG-shMKK4.B (3) could reconstitute liver function, as shown by the survival and restoration of body weights.

This result is further supported by FIG. 4 showing livers explanted at day 20 after administration of the nucleic acid construct, where livers are in the process of repopulation by hepatocytes which were co-transfected in vivo with a nucleic acid construct containing an expression cassette for FAH and GFP and including an expression cassette for inhibitory RNA specific for mRNA encoding MKK4 (p/T-FAHIG-shMKK4, both left-hand pictures), or including an expression cassette encoding a non-specific inhibitory RNA (p/T-FAHIG-shCtr, both right-hand pictures). The explanted livers of FIG. 4 show a faster increase of GFP fluorescence over time in vivo from animals co-transfected with the nucleic acid construct which includes the expression cassette encoding an inhibitory RNA specific for the mRNA encoding MKK4 compared to animals co-transfected with the nucleic acid construct which includes the expression cassette encoding an inhibitory RNA with no target.

The result from fluorescence is confirmed in this case in fully repopulated mouse livers by the immunospecific staining for MKK4 in the Western blot shown in FIG. 5 and by the immunofluorescence analyses for expression of MKK4 in the tissue samples of explanted mouse livers which are shown in FIG. 6.

In FIG. 5, shMKK4-224 denotes protein extracts from mouse livers repopulated with an expression cassette encoding an inhibitory RNA against MKK4 and shMKK4-3553 denotes protein extracts from mouse livers repopulated with an expression cassette encoding an independent inhibitory RNA against MKK4; tubulin served as a loading control and was detected by a specific antibody (α-tub), MKK4 was detected by an anti-MKK4 antibody (α-MKK4). In FIG. 6, FAHIG-shCtr denotes a nucleic acid construct containing the expression cassette for the complementing FAH and for GFP, including a non-specific inhibitory RNA (shCtr). shMKK4-A and shMKK4-B denote nucleic acid constructs containing expression cassettes for shRNA which specifically hybridize to the mRNA of MKK4.

Both analyses show that only the nucleic acid construct which includes an expression cassette encoding an inhibitory RNA specific for the mRNA encoding MKK4 results in a decrease of MKK4 expression in hepatocytes.

FIG. 7 shows Western blots for cyclin A and E of nuclear extracts from the mouse livers contacted with the nucleic acid construct expressing the shRNA hybridizing to MKK4 mRNA (shMKK4, +) and expressing the non-specific shRNA (shCtr, +), respectively, at 0, at 24 h, at 38 h, and at 48 h after partial hepatectomy, detected with α-cyclin A antibody (α-Cyc.A) and α-cyclin B antibody (α-Cyc.B). This analysis shows that inactivation of MKK4, which is e.g. obtained by the expression of an inhibitory RNA hybridizing to the mRNA encoding MKK4, leads to an earlier entry of the cell cycle after partial hepatectomy.

FIG. 8 shows a Ki67 stain of livers of the experimental animals having received the nucleic acid construct expressing the inhibitory RNA specific for MKK4 mRNA (shMKK4) and of animals having received the construct expressing the non-specific shRNA (shCtr), respectively, at 0 h, 38 h, and 48 h following partial hepatectomy. The analyses show that the inactivation of MKK4, which in the example is obtained by presence of the shRNA which is specific for MKK4 mRNA and is expressed from the nucleic acid construct introduced into the hepatocytes results in an increase of hepatocyte proliferation in vivo.

FIG. 9 shows a quantification of the Ki67-positive cells from the analyses of FIG. 8. The increase in hepatocyte proliferation for the hepatocytes containing the shRNA inhibiting expression of MKK4 (p/t-FAHIG-shMKK4) is significant in comparison to the non-specific shRNA control (p/t-FAHIG-shCtr).

FIG. 10 shows TUNEL staining for identification of apoptotic cells in liver tissue from mice transfected by an integrating nucleic acid construct containing an expression cassette for non-specific shRNA (shCtr.), or an expression cassette for shRNA which specifically hybridizes to mRNA of MKK4 (shMKK4.224 or shMKK4.355, each expressing a mouse-specific siRNA hybridizing to the RNA of MKK4). Apoptosis was induced in vivo at 9 h prior to the analysis experimentally by injection of Jo2 antibody, which interacts with CD95 to induce fulminant liver failure. TUNEL staining reveals less apoptotic hepatocytes in the liver tissue expressing the MKK4-specific shRNA (shMKK4.224, shMKK4.355) than in controls (shCtr.). The upper row of pictures shows fluorescence micrographs of TUNEL analyses, the lower row shows bright field micrographs of H&E stained tissue samples.

The quantification of TUNEL analysis following induction of liver failure is shown in FIG. 11, demonstrating a significantly lower number of apoptotic hepatocytes in those liver tissues containing the shRNA (shMKK4.224 and shMKK4.3553) that hybridizes to mRNA of MKK4 when compared to the control with non-specific shRNA (shCtr.).

FIG. 12 shows the survival rate according to Kaplan Meier of mice transfected with the nucleic acid construct expressing the shRNA hybridizing to mRNA of MKK4 (shMKK4.224 and shMKK4.3553) and of control mice (shCtr.) after the experimental induction of liver failure. The result demonstrates that inactivation of MKK4, which inactivation in the example is obtained by expression of an inhibitory RNA (shRNA) from an expression cassette of a nucleic acid construct, effectively protects hepatocytes in vivo against apoptosis.

Example 2

Inhibition of MKK4 In vivo by Transcription of Inhibitory RNA from an Expression Cassette Encoding shRNA For transient transfection of hepatocytes, a nucleic acid construct containing or consisting of an expression cassette encoding an inhibitory RNA which specifically hybridizes to the mRNA encoding MKK4, e.g. containing SEQ ID NO: 1 or SEQ ID NO: 2 (which are both specific for the human and the mouse mRNA of MKK4) was transiently introduced into hepatocytes. For transient transfection in vivo, the nucleic acid construct was formulated in liposomes and administered to the experimental animals. The liposome formulation contained the lipids 3-N-[(qmethoxypoly(ethylene glycol)2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar per cent ratio.

The effect of increasing proliferation of hepatocytes, protection against induction of apoptosis could be shown as laid out for the stable expression of the shRNA in Example 1, indicating that the effect was limited to the period in which the shRNA was present in the hepatocytes using the analytical methods as described in Example 1. This shows that MKK4 activity can effectively be inhibited or inactivated by transient expression of inhibitory RNA, e.g. shRNA or microRNA, from an expression cassette of a nucleic acid construct which does not integrate into the hepatocyte.

Example 3

Inhibition of MKK4 In vivo by Inhibitory RNA Transfected into Hepatocytes

Suitability of inhibitory RNA for use as a medicament could be shown by transfecting the inhibitory RNA which specifically hybridizes to mRNA of MKK4 into liver tissue in vivo. Inhibitory RNA could be shRNA or microRNA, preferably formulated as liposomes or lipid nanoparticles. Generally, reduction or elimination of MKK4 could be obtained in at least a fraction of the liver tissue contacted by the formulation of the inhibitory RNA using the analytical methods as described in Example 1. This shows that inhibitory RNA specific for mRNA of MKK4 can be used as a medicament, especially for the treatment of impaired liver function.

Example 4

Inhibition of MKK4 In vivo by SP600125, Myricitine, Genistein, or PD98059 in Hepatocytes In the alternative to inhibition of MKK4 activity in liver tissue by inhibitory RNA, SP600125, myricitine, Genistein, or PD98059 were used for inactivating MKK4 in the liver. Generally, SP600125, myricitine, Genistein, or PD98059 were administered to mice at a dosage efficient for in vivo inactivation of MKK4. Preferably, the dosage was efficient to inactivate at least 80%, more preferably at least 90 or 95% of mean in vivo MKK4 activity.

It could be found that the inactivation of MKK4 in the liver by administration of SP600125, myricitine, Genistein, or PD98059 as a medicament resulted in a significant increase in liver regeneration, an increase in proliferation, and in protection against induced apoptosis using the analytical methods as described in Example 1.

Example 5

Inhibition of MKK4 in Primary Hepatocytes Cultured In vitro by Stable or Transient Transcription of Inhibitory RNA from an Expression Cassette Encoding shRNA For in vitro transfection, cultured primary hepatocytes obtained from experimental animals were contacted by the nucleic acid construct as described in Example 1 or 2. Generally, the nucleic acid construct could be formulated as liposomes according to Example 2. Generally, stable or transient expression of the inhibitory RNA could be obtained in the cultured hepatocytes, and reduction or elimination of MKK4 could be detected using the analytical methods as described in Example 1.

For experimental purposes, in the alternative to in vitro transfection of primary hepatocytes originating from an experimental animal, stably transfected hepatocytes expressing shRNA specific for MKK4 mRNA were isolated from the experimental mice generated according to Example 1. Analysis of cultured hepatocytes was by quantification of the incorporation of EdU by primary hepatocytes by flow cytometry. The result of cultivated transfected hepatocytes after 3 days culture is shown in FIG. 13. The inset phase contrast micrographs and the relation of hepatocytes containing shRNA specific for mRNA of MKK4, generated by expression from the transfected expression cassette, show that cultured hepatocytes with inactivated MKK4 (FAHIG-shMKK4) show a drastically improved EdU incorporation as a marker for proliferation over controls (FAHIG-shCtr) without inhibition of MKK4 activity in culture.

Replating of the cultured hepatocytes in fresh culture medium shows the increased long-term survival of cultured hepatocytes in which MKK4 activity is essentially inhibited, e.g. by presence of inhibitory RNA (shMKK4) that specifically hybridizes to mRNA of MKK4, as shown in the micrographs of FIG. 14. Hepatocytes with inactivated MKK4 (shMKK4) can be cultured effectively at least to day 29 (d29), and can be cultured by trypsinizing and replating to fresh medium at day 15; right-hand micrographs show day 3 of cells replated after 15 days initial culture. In contrast, transfected cells with a non-specific shRNA (shCtr) show a lower long term survival in culture and no growth upon replating after 15 days initial culture. These results show that the inactivation of MKK4 activity drastically increases long term survival and replating efficiency of cultured hepatocytes.

Generally, the generally known Eagles medium was used for hepatocyte cultures.

Example 6

Cultured Hepatocytes with Inactivated MKK4 Activity for Use as a Medicament for Liver Regeneration Hepatocytes from a mouse representing a patient having a compatible or identical blood group, preferably hepatocytes that were immunologically compatible with a later recipient, e.g. a patient, preferably autologous hepatocytes, were cultured. MKK4 activity was inhibited as described in the above Examples, preferably by transfection of cultured hepatocytes with a nucleic acid construct containing an expression cassette for an inhibitory RNA hybridizing to the mRNA encoding MKK4, by transfection with an inhibitory RNA, preferably repeatedly, or by contacting with SP600125, myricitine, Genistein, or PD98059.

Cultured mouse hepatocytes which were stably transfected with a nucleic acid construct expressing the complementing FAH and GFP (FAHIG) and an inhibitory RNA specific for the mRNA encoding MKK4 or a non-specific shRNA (Ctrl), respectively, were harvested by trypsinizing. These hepatocytes were suspended in a pharmaceutically acceptable carrier and transplanted into the spleen or liver of FAH −/− mice, which subsequently were kept without NTBC. The Kaplan Meier analysis of survival after intrasplenic transplantation of the cultured hepatocytes is shown in FIG. 15. In comparison to mice having received hepatocytes containing the non-specific shRNA (shRNA.Ctrl) that die at day 37-38 (vertical line), mice having received hepatocytes containing shRNA Mkk4 specific for the mRNA of MKK4 by expression from the expression cassette encoding the shRNA have a drastically increased survival.

The experimental FAH −/− mice that had repopulated livers with hepatocytes with an expression cassette for GFP, including the shRNA specific for the mRNA encoding MKK4 (shRNA.MKK4) were kept for 12 months following repopulation. Analyses of explanted livers in bright field photography (Bright), with GFP imaging (GFP) (left-hand pictures of FIG. 16) and anti-FAH immunofluorescence and H&E staining of liver sections (right-hand pictures of FIG. 16) show no tumor development with stable intrahepatic expression of GFP and of the shRNA specifically inactivating MKK4. These data emphasize that MKK4 inhibition can be used to increase regeneration without triggering tumor growth.

Example 7

Cultivated Hepatocytes with Inactivated MKK4 Activity for Use as a Device for Extracorporal Blood Purification Cultured hepatocytes obtained as described above, preferably by cultivating primary hepatocytes which were stably transfected with a nucleic acid construct expressing an shRNA specific for the mRNA encoding MKK4 were grown on a carrier substrate, e.g. a polymer carrier. The cultured hepatocytes adhering to the carrier substrate were arranged in a container which was perfused with blood withdrawn from a patient, exemplified by a mouse or rat. Blood exiting the container could immediately be returned into the patient.

In initial experiments, it could be shown that hepatocytes which are genetically manipulated to stably express an shRNA inactivating the mRNA encoding MKK4 are stable when grown on a carrier substrate, and that these cultures hepatocytes could be used as a blood purification device.

Example 8

Inactivation of MKK4 in In vitro Analyses

The inhibitory effect of compounds against MKK4 was analysed in an in vitro assay using purified MKK4 protein, e.g. obtained from a cell line that was genetically manipulated to over-express MKK4 from an expression cassette containing the nucleotide sequence SEQ ID NO: 1204 as a coding sequence and affinity purification using e.g. an antibody directed against MKK4 protein.

In the assay, purified active MKK4 protein was incubated with its substrate JNK1a1 and $^{32}$P-labelled gATP (5 µCi, approx. 10 µM), without additional active compound, with the small inhibitory compound, or with Genistein as a positive control. For the assay, kinase assay buffer (20 mM HEPES pH 7.5; 10 mM $MgCl_2$; 1 mg/ml BSA; 1 mM $Na_3VO_4$; 1 mM DTT) was used. An inhibitory effect of the small inhibitory compound (final concentration 50 µM) was detected as a reduction of the phosphorylation activity of MKK4 protein on its substrate JNK1a1 by measuring the amount of radioactive ($^{32}$P) phosphate in JNK1a1. Phosphorylation of JNK1a1 was measured in the presence of 2 ml scintillation cocktail per sample by using a scintillation counter (Wallac, Liquid Scintillation Counter). In this assay, Genistein gave an inhibition to approx. 80% activity compared to the assay without additional active compound.

TABLE 1 small inhibitory compounds assayed for inhibitory activity against MKK4:

| name | Structure | Inhibition, relative activity of MKK4 compared to control (without additional compound) (%) |
|---|---|---|
| ZM 336372; 3-(Dimethylamino)-N-[3-[(4-hydroxybenzoyl)-amino]-4-methylphenyl] benzamide | 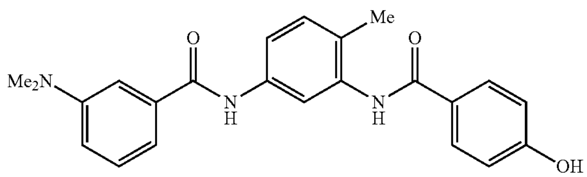 [SMILES: Cc1ccc(NC(=O)c2cccc(N(C)C)c2)cc1NC(=O)c1ccc(O)cc1] | 54.2 |
| BAS00525963; 2-hydroxy-1-methyl-4-oxo-N-pyridin-4-ylquinoline-3-carboxamide | 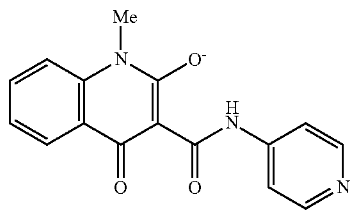 [SMILES: Cn1c([O-])c(C(=O)Nc2ccncc2)c(=O)c2ccccc21] | 72.6 |
| BAS00697444; 2-(1H-indazol-5-yliminomethyl)-6-nitrophenolate | 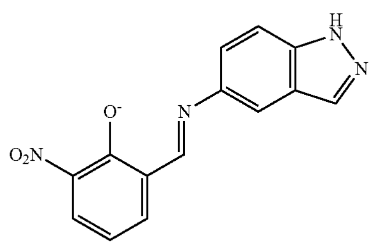 [SMILES: O=[N+]([O-])c1cccc(/C=N/c2ccc3[nH]ncc3c2)c1[O-]] | 79.0 |
| SYN22174524; 5-[2-(3,5-dimethyl-1H-pyrazol-4-yl)ethyl]-7-oxo-N-phenyl-1H-pyrazolo[1,5-a]pyrimidine-3-carboxamide | 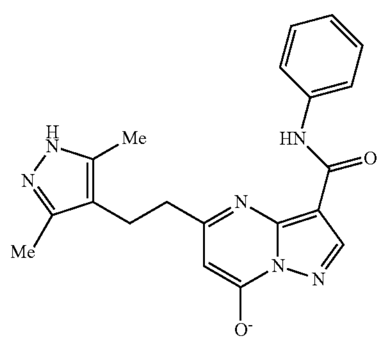 [SMILES: Cc1n[nH]c(C)c1CCc1cc([O-])n2ncc(C(=O)Nc3ccccc3)c2n1] | 47.8 |
| SYN22174787; 5-[2-(3,5-dimethyl-1H-pyrazol-4-yl)ethyl]-3-(4-fluorophenyl)-1H-pyrazolo[1,5-a]pyrimidin-7-one | 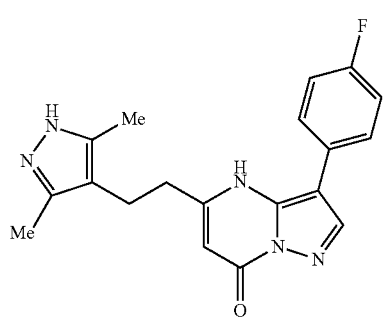 [SMILES: Cc1n[nH]c(C)c1CCc1cc(=O)n2ncc(-c3ccc(F)cc3)c2[nH]1] | 41.5 |

TABLE 1-continued small inhibitory compounds assayed for inhibitory activity against MKK4:

| name | Structure | Inhibition, relative activity of MKK4 compared to control (without additional compound) (%) |
|---|---|---|
| SYN22175977; 5-[2-(3,5-dimethyl-1H-pyrazol-4-yl)ethyl]-3-(4-methylphenyl)-1H-pyrazolo[1,5-a]pyrimidin-7-one | 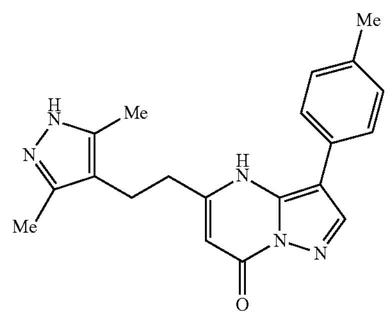 [SMILES: Cc1ccc(-c2cnn3c(=O)cc(CCc4c(C)n[nH]c4C)[nH]c23)cc1] | 55.5 |
| SYN22176267; 3-(4-chlorophenyl)-5-[2-(3,5-dimethyl-1H-pyrazol-4-yl)ethyl]-2-(methoxymethyl)-1H-pyrazolo[1,5-a]pyrimidin-7-one | 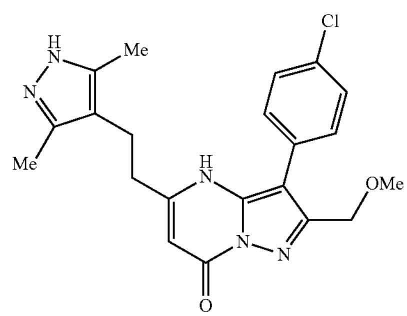 [SMILES: COCc1nn2c(=O)cc(CCc3c(C)n[nH]c3C)[nH]c2c1-c1ccc(Cl)cc1] | 59.1 |
| SYN22176367; 5-[2-(3,5-dimethyl-1H-pyrazol-4-yl)ethyl]-2-(methoxymethyl)-3-(4-methylphenyl)-1H-yrazolo[1,5-a]pyrimidin-7-one | 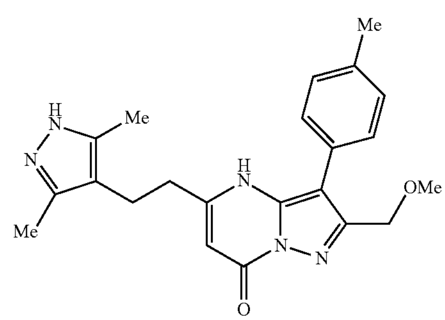 [SMILES: COCc1nn2c(=O)cc(CCc3c(C)n[nH]c3C)[nH]c2c1-c1ccc(C)cc1] | 49.9 |
| SYN22176842; 5-[2-(3,5-dimethyl-1H-pyrazol-4-yl)ethyl]-2-(3-methoxyphenyl)-3-methyl-pyrazolo[5,1-b]pyrimidin-7-ol | 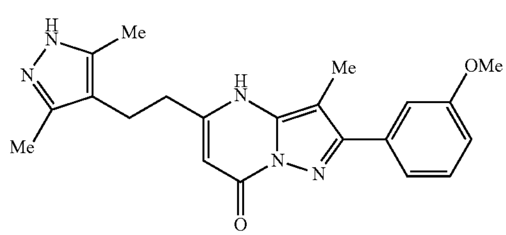 [SMILES: COc1cccc(-c2nn3c(=O)cc(CCc4c(C)n[nH]c4C)[nH]c3c2C)c1] | 54.9 |
| SYN22176990; 5-[2-(3,5-dimethyl-1H-pyrazol-4-yl)ethyl]-2-(2-methoxyphenyl)-3-methyl-pyrazolo[5,1-b]pyrimidin-7-ol | 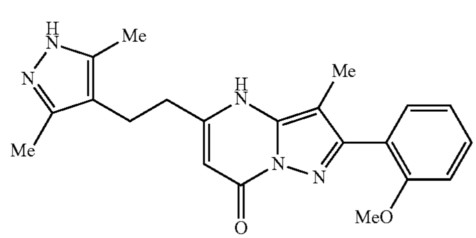 [SMILES: COc1ccccc1-c1nn2c(=O)cc(CCc3c(C)n[nH]c3C)[nH]c2c1C] | 58.2 |

TABLE 1-continued small inhibitory compounds assayed for inhibitory activity against MKK4:

| name | Structure | Inhibition, relative activity of MKK4 compared to control (without additional compound) (%) |
|---|---|---|
| SYN22177890; 3-(4-chlorophenyl)-5-[2-(3,5-dimethyl-1H-pyrazol-4-yl)ethyl]-2-methyl-1H-pyrazolo[1,5-a]pyrimidin-7-one | 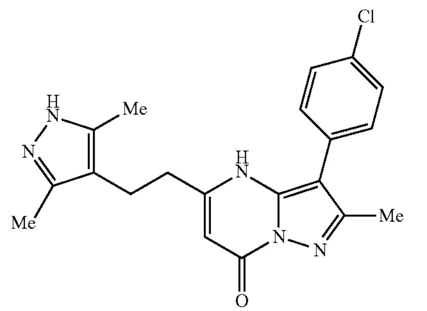 [SMILES: Cc1n[nH]c(C)c1CCc1cc(=O)n2nc(C)c(-c3ccc(Cl)cc3)c2[nH]1] | 56.3 |
| BAS00896568; 5-amino-3-[(Z)-1-cyano-2-[3-[(4-methoxy-6-piperidin-1-yl-1,3,5-triazin-2-yl)oxy]phenyl]ethenyl]-1-(2-hydroxyethyl)pyrazole-4-carbonitrile | 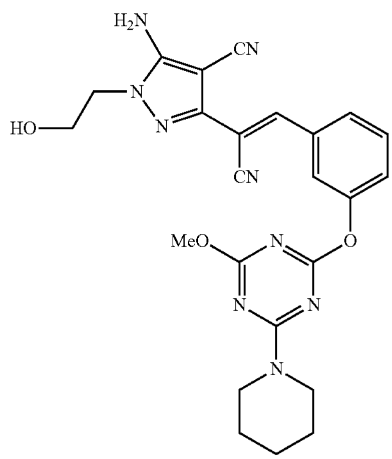 [SMILES: COc1nc(Oc2cccc(/C=C(\C#N)c3nn(CCO)c(N)c3C#N)c2)nc(N2CCCCC2)n1] | 58.4 |
| BAS00697462; 2-(1H-indazol-5-yliminomethyl)-6-methoxy-4-nitrophenolate | 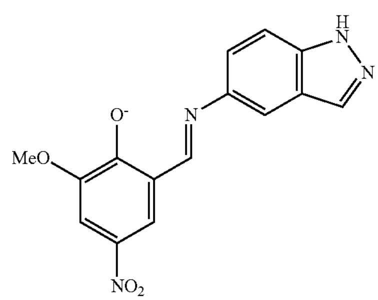 [SMILES: COc1cc([N+](=O)[O-])cc(/C=N/c2ccc3[nH]ncc3c2)c1[O-]] | 71.1 |
| BAS00368055; 7-oxobenzo[e]-perimidine-4-carboxylic acid | 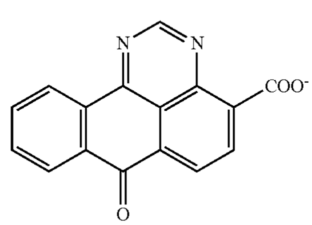 | 66.2 |

TABLE 1-continued small inhibitory compounds assayed for inhibitory activity against MKK4:

| name | Structure | Inhibition, relative activity of MKK4 compared to control (without additional compound) (%) |
| --- | --- | --- |
| IUPAC Name: 1-phenyl-2-[[4-phenyl-5-[(5-phenyltetrazol-2-yl)methyl]-1,2,4-triazol-3-yl]sulfanyl]ethanone | 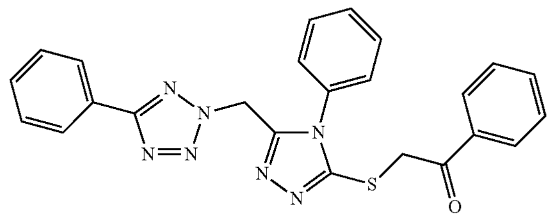 [SMILES: O=C(CSc1nnc(Cn2nnc(-c3ccccc3)n2)n1-c1ccccc1)c1ccccc1] | |
| IUPAC Name: 2-[[5-[(2,4-dimethylanilino)methyl]-4-(furan-2-ylmethyl)-1,2,4-triazol-3-yl]sulfanylmethyl]-1H-quinazolin-4-one | | |
| N-(2-furylmethyl)-N-[1-(isopentylcarbamoyl)ethyl]-5-(morpholinomethyl)-furan-2-carboxamide | 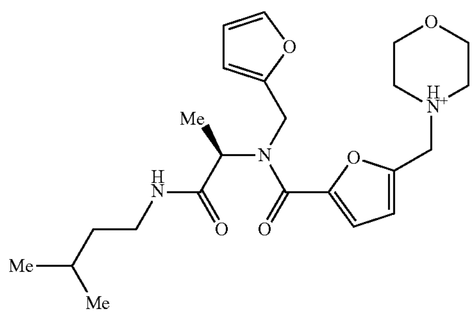 | |
| IUPAC Name: 4-N-benzyl-1-N-[2-(3,4-dimethoxyphenyl)-ethyl]-4-N-ethylbenzene-1,4-disulfonamide | 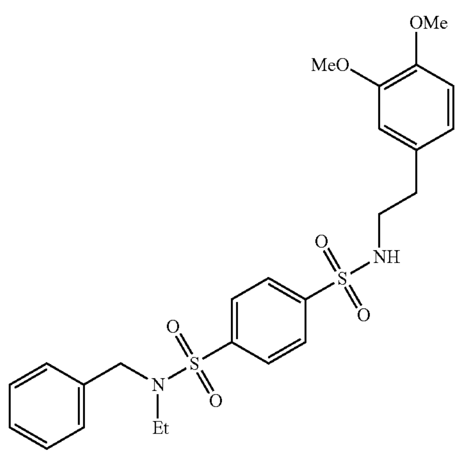 [SMILES: CCN(Cc1ccccc1)S(=O)(=O)c1ccc(S(=O)(=O)NCCc2ccc(OC)c(OC)c2)cc1] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 3-[2-(2,5-dimethoxyphenyl)-2-oxoethyl]sulfanyl-6-methyl-2H-1,2,4-triazin-5-one | 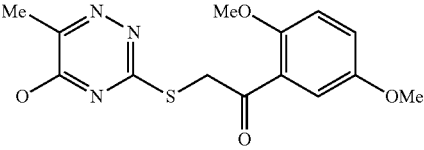 [SMILES: COc1ccc(OC)c(C(=O)CSc2nnc(C)c(O)n2)c1] | |
| IUPAC Name: 2-[4-(4-methylbenzoyl)-piperidin-1-yl]sulfonylbenzoate | 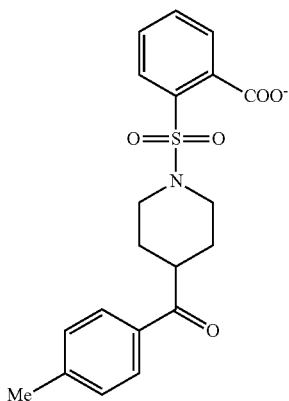 | |
| IUPAC Name: 2-[4-[(2,4-dioxo-1,3-thiazolidin-5-ylidene)methyl]-2-methoxyphenoxy]-acetic acid | 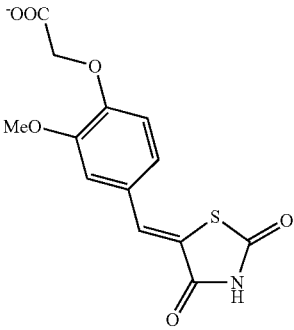 | |
| Popular Name: N-(6-ethoxy-1,3-benzothiazol-2-yl)-2-[[2-(p-tolyl)-9H-purin-6-yl]sulfanyl]acetamide | 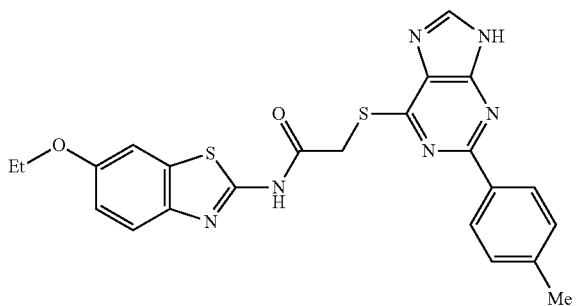 [SMILES: CCOc1ccc2nc(NC(=O)CSc3nc(-c4ccc(C)cc4)nc4[nH]cnc34)sc2c1] | |

TABLE 1-continued small inhibitory compounds assayed for inhibitory activity against MKK4:

| name | Structure | Inhibition, relative activity of MKK4 compared to control (without additional compound) (%) |
|---|---|---|
| 2-[4-(4-methoxy-phenyl)-piperazin-1-yl]-N-(3-morpholino-sulfonyl-phenyl)-acetamide | 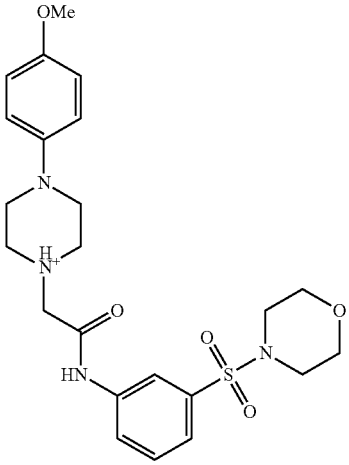 | |
| Popular Name: 5-[[4-[(2,4,6-trioxohexa-hydropyrimidin-5-ylidene)methyl]-phenoxy]methyl]-furan-2-carboxylic | 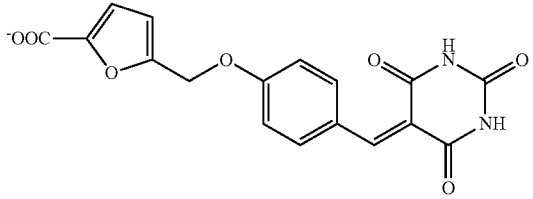 | |
| IUPAC Name: 3-(benzimidazol-1-yl)-N-[(2R)-1-[3-(3,4-difluorophenyl)-6-oxopyridazin-1-yl]butan-2-yl]propanamide | 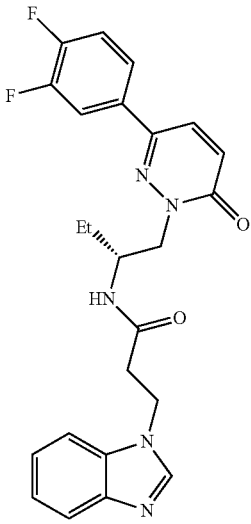 [SMILES: CC[C@H](Cn1nc(-c2ccc(F)c(F)c2)ccc1=O)NC(=O)CCn1cnc2ccccc21] | |
| IUPAC Name: 2-methyl-3-(pyridin-3-ylmethylamino)benzoate | 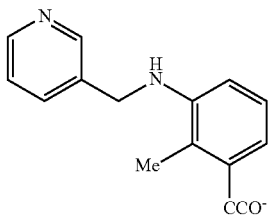 | |

TABLE 1-continued small inhibitory compounds assayed for inhibitory activity against MKK4:

| name | Structure | Inhibition, relative activity of MKK4 compared to control (without additional compound) (%) |
| --- | --- | --- |
| IUPAC Name: N-[2-[[4-amino-6-(dimethylamino)-1,3,5-triazin-2-yl]oxy]ethyl]-2-(4-chloro-2-methylphenoxy)acetamide | 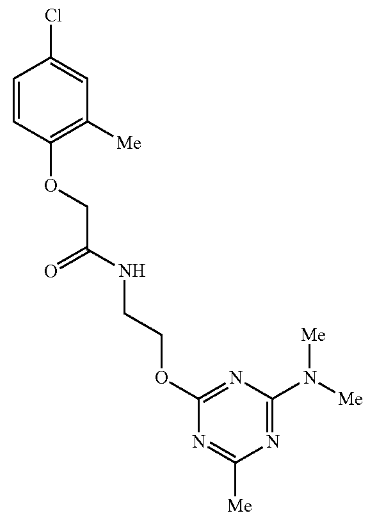 [SMILES: Cc1nc(OCCNC(=O)COc2ccc(Cl)cc2C)nc(N(C)C)n1] | |
| IUPAC Name: [3-ethoxy-4-(thiophen-2-ylmethoxy)phenyl]methyl-(2-morpholin-4-ium-4-ylethyl)azanium | 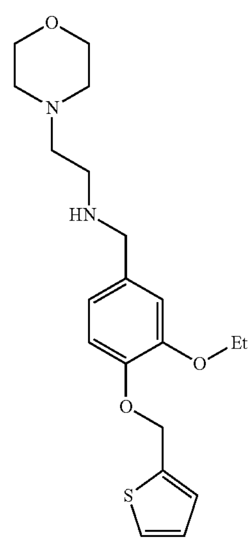 [SMILES: CCOc1cc(CNCCN2CCOCC2)ccc1OCc1cccs1] | |
| IUPAC Name: 2-[4-(2-hydroxyethyl)piperazin-1-yl]-N-(2-pyrrolidin-1-ylsulfonylethyl)pyridine-3-carboxamide | 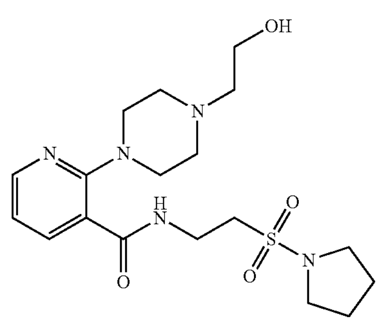 [SMILES: O=C(NCCS(=O)(=O)N1CCCC1)c1cccnc1N1CCN(CCO)CC1] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 1-[[2-(furan-2-yl)-1H-pyrrolo[2,3-b]pyridin-3-yl]methyl-methylamino]-3-(4-methoxyphenoxy)propan-2-ol | 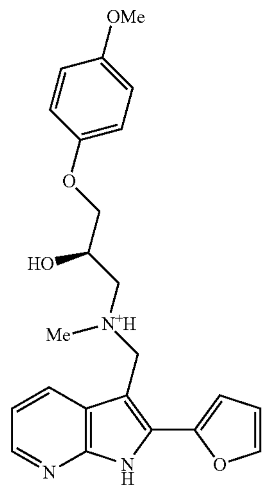 | |
| IUPAC Name: N-ethyl-3-[2-(4-methoxyphenoxy)ethoxy]-N-(pyrazolo[1,5-a]pyrimidin-3-ylmethyl)aniline | 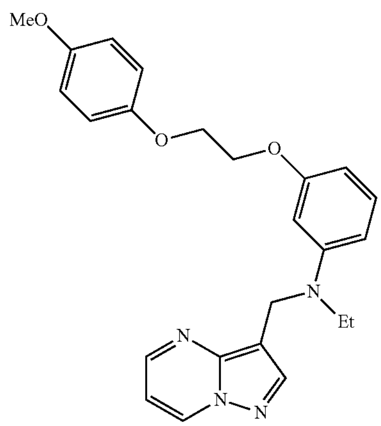 [SMILES: CCN(Cc1cnn2cccnc12)c1cccc(OCCOc2ccc(OC)cc2)c1] | |
| IUPAC Name: N-ethyl-3-[2-(4-fluorophenoxy)ethoxy]-N-[(2-methylpyrimidin-5-yl)methyl]aniline | 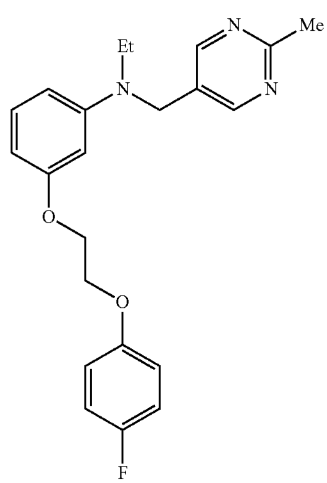 [SMILES: CCN(Cc1cnc(C)nc1)c1cccc(OCCOc2ccc(F)cc2)c1] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 2-methoxy-5-morpholin-4-ylbenzoate | 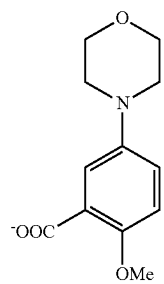 | |
| IUPAC Name: (1R,2S,3R)-3-(2-aminobenzoyl)-3-methyl-2-N-[(5-methyl-1,2,4-oxadiazol-3-yl)methyl]-1-N-(pyridin-4-ylmethyl) cyclopropane-1,2-dicarboxamide | 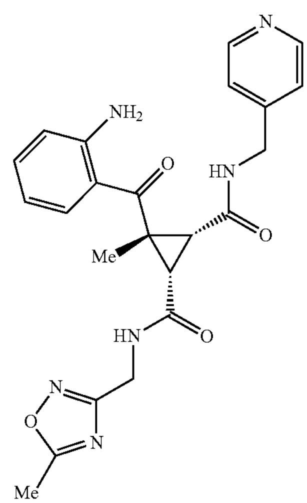 [SMILES: Cc1nc(CNC(=O)[C@H]2[C@@H](C(=O)NCc3ccncc3)[C@@]2(C)C(=O)c2ccccc2N)no1] | |
| IUPAC Name: (2S,3S)-2,3-bis(ethoxycarbonyl) butanedioate | 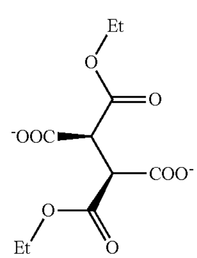 | |
| IUPAC Name: diethyl 2-[(1,4-diethoxy-1,4-dioxobut-2-en-2-yl)amino]but-2-enedioate | 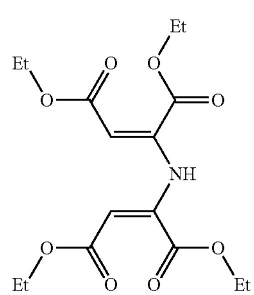 [SMILES: CCOC(=O)/C=C(/N/C(=C/C(=O)OCC)C(=O)OCC)C(=O)OCC] | |

TABLE 1-continued small inhibitory compounds assayed for inhibitory activity against MKK4:

| name | Structure | Inhibition, relative activity of MKK4 compared to control (without additional compound) (%) |
| --- | --- | --- |
| IUPAC Name: (2S,3S)-2,3-bis(ethoxycarbonyl)butanedioate | 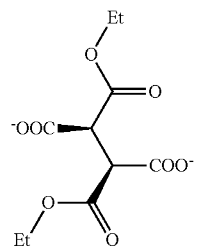 | |
| IUPAC Name: diethyl 2-[(1,4-diethoxy-1,4-dioxobut-2-en-2-yl)amino]but-2-enedioate | 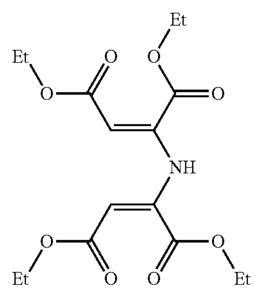 [SMILES: CCOC(=O)/C=C(/N/C(=C/C(=O)OCC)C(=O)OCC)C(=O)OCC] | |
| IUPAC Name: 1-ethyl-2-hydroxy-N-(4-hydroxyphenyl)-4-oxoquinoline-3-carboxamide | 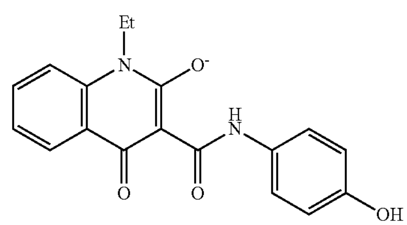 [SMILES: CCn1c([O-])c(C(=O)Nc2ccc(O)cc2)c(=O)c2ccccc21] | |
| IUPAC Name: 5-(phenylcarbamoyl-oxy)pentyl N-phenylcarbamate | 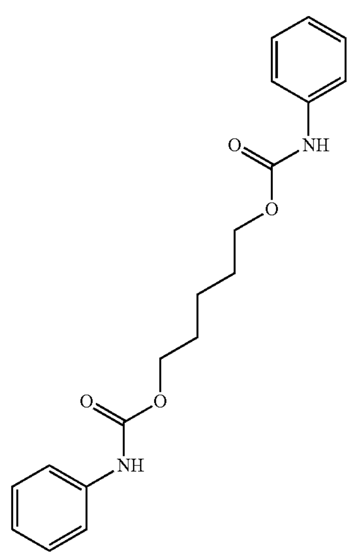 [SMILES: O=C(Nc1ccccc1)OCCCCCOC(=O)Nc1ccccc1] | |

TABLE 1-continued small inhibitory compounds assayed for inhibitory activity against MKK4:

| name | Structure | Inhibition, relative activity of MKK4 compared to control (without additional compound) (%) |
|---|---|---|
| Popular Name: N-[(5-acetamido-2-methoxy-phenyl)methyl]-2-morpholino-acetamide | 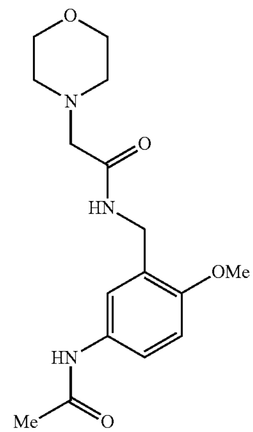 [SMILES: COc1ccc(NC(C)=O)cc1CNC(=O)CN1CCOCC1] | |
| IUPAC Name: 4-[4,6-bis(3-carboxypropyl)-1,3,5-trioxan-2-yl]butanoic acid | 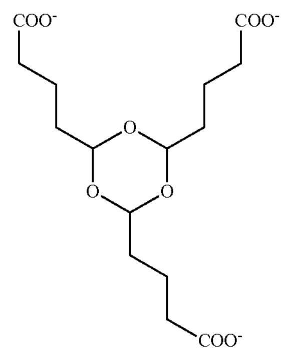 | |
| UPAC Name: methyl4-[(4-oxo-2-sulfanylidene-1,3-thiazolidin-5-ylidene)methyl]benzoate | 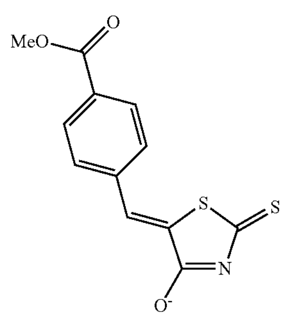 [SMILES: COC(=O)c1ccc(/C=C2\SC(=S)N=C2[O-])cc1] | |
| IUPAC Name: 2-(3-methylanilino)-N-[(3-nitrophenyl)methylideneamino]acetamide | 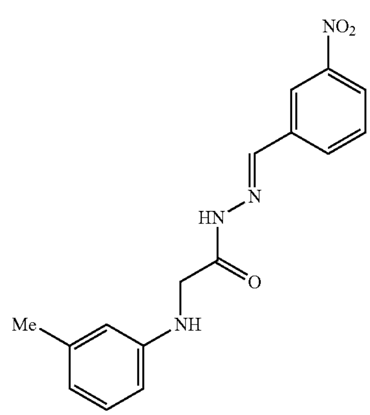 [SMILES: Cc1cccc(NCC(=O)N/N=C/c2cccc([N+](=O)[O-])c2)c1] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: [(2R)-2-[3-[bis[3-(dimethylazaniumyl)propyl]amino]propanoyloxy]-3-(dimethylamino)propyl]-dimethylazaium | 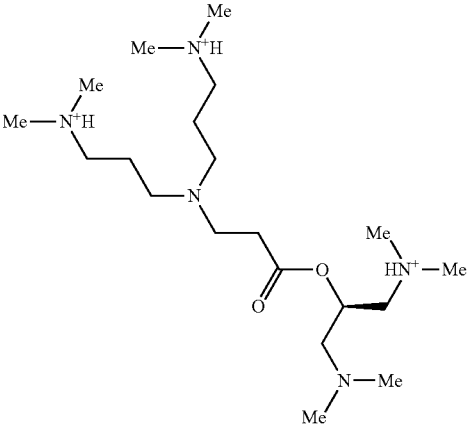 | |
| IUPAC Name: 2-hydroxy-4-oxo-N-pyridin-4-yl-1H-quinoline-3-carboxamide | 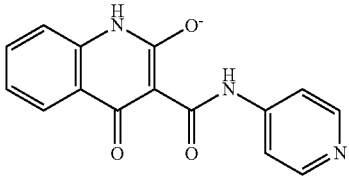 [SMILES: O=C(Nc1ccncc1)c1c([O-])[nH]c2ccccc2c1=O] | |
| IUPAC Name: 1-ethyl-2-hydroxy-4-oxo-N-pyridin-4-ylquinoline-3-carboxamide | 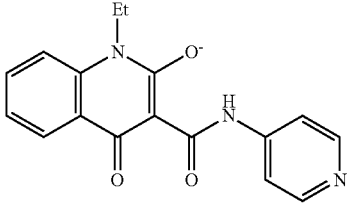 [SMILES: CCn1c([O-])c(C(=O)Nc2ccncc2)c(=O)c2ccccc21] | |
| UPAC Name: 2,3-bis[2-(2-nitrophenoxy)ethoxy]-1,4-dioxane | 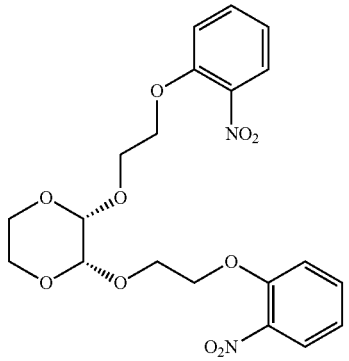 [SMILES: O=[N+]([O-])c1ccccc1OCCO[C@@H]1OCCO[C@@H]1OCCOc1ccccc1[N+](=O)[O-]] | |
| 4-hydroxy-2-oxo-N-(4-pyridinylmethyl)-1,2-dihydro-3-quinoline carboxamide | 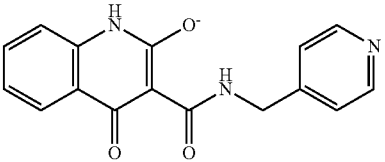 [SMILES: O=C(NCc1ccncc1)c1c([O-])[nH]c2ccccc2c1=O] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 7-oxobenzo[e]perimidine-4-carboxylic acid | 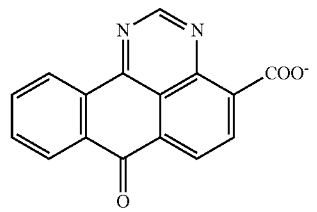 | |
| IUPAC Name: 1,3-dioxobenzo[de]isoquinoline-6-carboxylic acid | 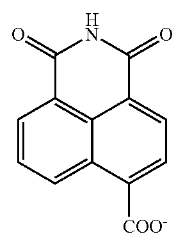 | |
| IUPAC Name: diethyl(2S)-2-[[3-[[(2S)-1,5-diethoxy-1,5-dioxopentan-2-yl]amino]-3-oxopropanoyl]amino]pentanedioate | 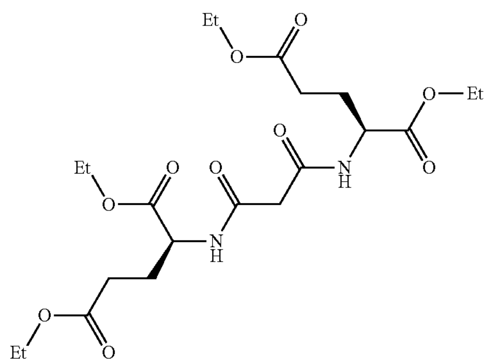 [SMILES: CCOC(=O)CC[C@H](NC(=O)CC(=O)N[C@@H](CCC(=O)OCC)C(=O)OCC)C(=O)OCC] | |
| IUPAC Name: diethyl2-[[2-acetamido-3-(4-phenylmethoxyphenyl)propanoyl]amino]pentanedioate | 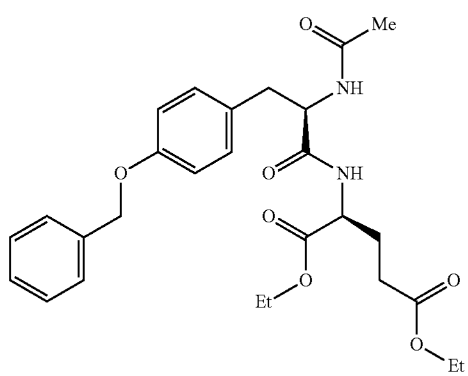 [SMILES: CCOC(=O)CC[C@H](NC(=O)[C@@H](Cc1ccc(OCc2ccccc2)cc1)NC(C)=O)C(=O)OCC] | |
| IUPAC Name: 3-nitro-N-[(E)-[3-[(E)-[(3-nitrophenyl)hydrazinylidene]methyl]phenyl]methylideneamino]aniline | | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: (4-methoxyphenyl)methyl N-[[4-[2-(3,4-dimethoxy-phenyl)ethylamino]-4-oxobutan-2-ylidene]amino]carbamate | 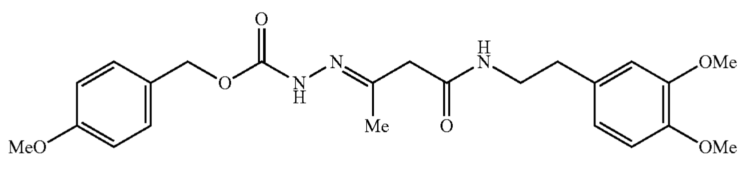 [SMILES: COc1ccc(COC(=O)N/N=C(\C)CC(=O)NCCc2ccc(OC)c(OC)c2)cc1] | |
| IUPAC Name: 3-amino-1,5-dihydropyrimido[5,4-b]indole-2,4-dione | 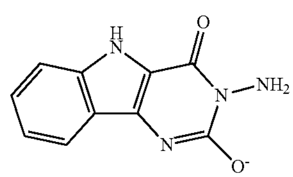 [SMILES: Nn1c([O-])nc2c([nH]c3ccccc32)c1=O] | |
| IUPAC Name: 1-[2-(2-fluorophenoxy)ethyl]-3-[6-[2-(2-fluorophenoxy)ethylcarbamoylamino]hexyl]urea | 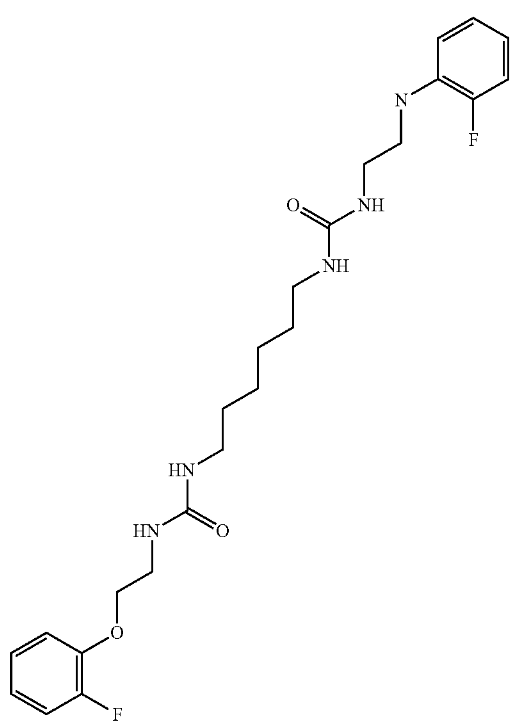 [SMILES: O=C(NCCCCCCNC(=O)NCCOc1ccccc1F)NCCNc1ccccc1F] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: methyl 4-[[[2-[2-[2-[[4-[hydroxy(methoxy)methyl]phenyl]methylidene]hydrazinyl]-2-oxoethoxy]acetyl]hydrazinylidene]methyl]benzoate | 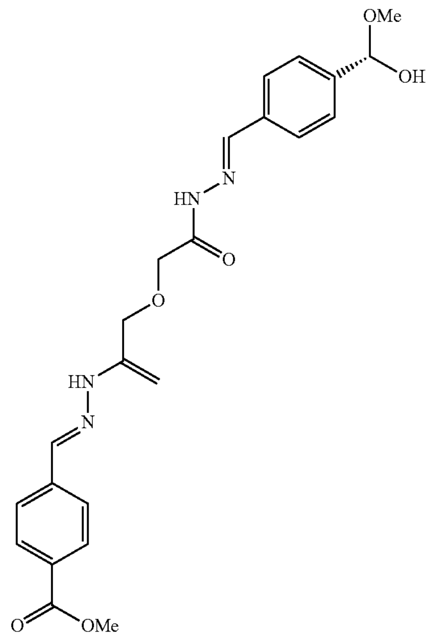 [SMILES: C=C(COCC(=O)N/N=C/c1ccc([C@@H](O)OC)cc1)N/N=C/c1ccc(C(=O)OC)cc1] | |
| IUPAC Name: N-[2-(3,4-dimethoxyphenyl)ethyl]-2-quinolin-8-ylsulfanylacetamide | 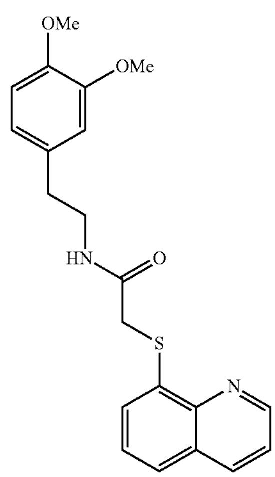 [SMILES: COc1ccc(CCNC(=O)CSc2cccc3cccnc23)cc1OC] | |
| IUPAC Name: (2S,3S)-2,3-bis(4-butoxyphenoxy)-1,4-dioxane | 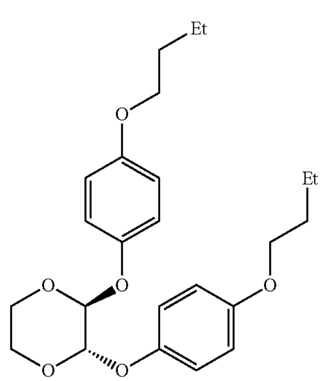 [SMILES: CCCCOc1ccc(O[C@@H]2OCCO[C@H]2Oc2ccc(OCCCC)cc2)cc1] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 2-hydroxy-1-methyl-4-oxo-N-pyridin-4-ylquinoline-3-carboxamide | 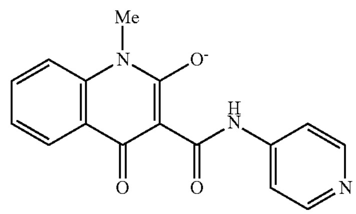 [SMILES: Cn1c([O-])c(C(=O)Nc2ccncc2)c(=O)c2ccccc21] | |
| IUPAC Name: quinoline-2,4-dicarboxylic acid | 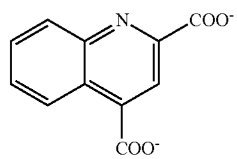 | |
| IUPAC Name: 2-[(5Z)-5-[(3-hydroxyphenyl)methylidene]-4-oxo-2-sulfanylidene-1,3-thiazolidin-3-yl]propanoic acid | 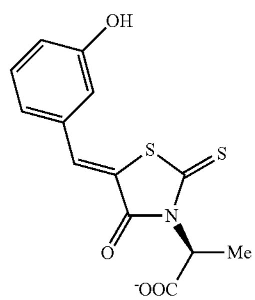 | |
| IUPAC Name: diethyl 2-acetamido-2-[[5-amino-2-(2-ethoxy-2-oxoethyl)phenyl]methyl]propanedioate | 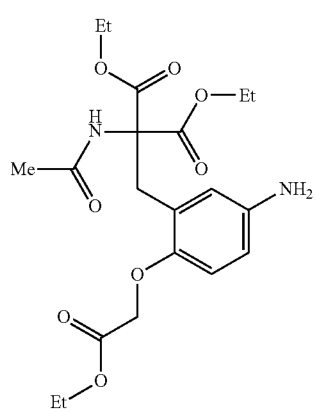 [SMILES: CCOC(=O)COc1ccc(N)cc1CC(NC(C)=O)(C(=O)OCC)C(=O)OCC] | |
| IUPAC Name: 4-[2-[2-[2-[(4-amino-1,2,5-oxadiazol-3-yl)oxy]ethoxy]ethoxy]ethoxy]-1,2,5-oxadiazol-3-amine | 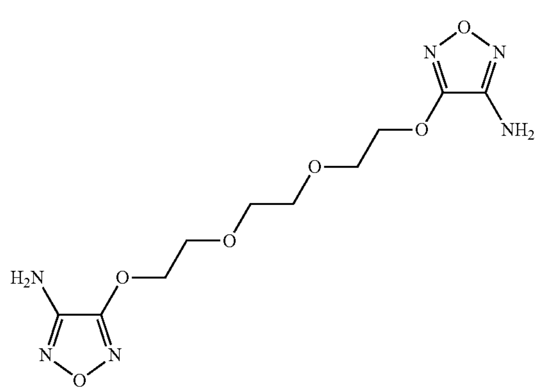 [SMILES: Nc1nonc1OCCOCCOCCOc1nonc1N] | |

TABLE 1-continued small inhibitory compounds assayed for inhibitory activity against MKK4:

| name | Structure | Inhibition, relative activity of MKK4 compared to control (without additional compound) (%) |
| --- | --- | --- |
| IUPAC Name: (1R,2S,3S,4S)-2-(thiophen-2-ylmethylcarbamoyl)bicyclo[2.2.1]hept-5-ene-3-carboxylate | 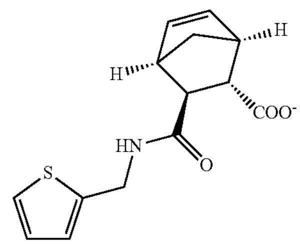 | |
| IUPAC Name: 3-[4-[2-[(4,4-dimethyl-2,6-dioxocyclohexylidene)methylamino]ethyl]piperazin-1-yl]-1-phenylpyrrolidine-2,5-dione | | |
| IUPAC Name: methyl 4-[N-[2-(N-(4-methoxy-4-oxobutanoyl)anilino)ethyl]anilino]-4-oxobutanoate | 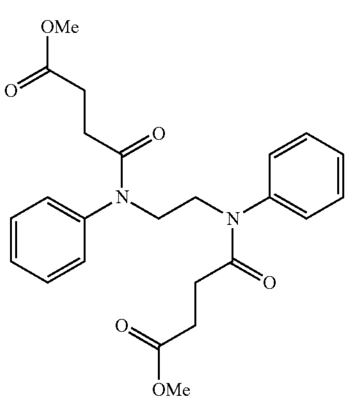 [SMILES: COC(=O)CCC(=O)N(CCN(C(=O)CCC(=O)OC)c1ccccc1)c1ccccc1] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 7-propan-2-ylidene-2-(pyridin-3-ylmethylcarbamoyl)bicyclo[2.2.1]hept-5-ene-3-carboxylic acid | | |
| 1-[4-[2-hydroxy-3-(2-pyridylmethylamino)propoxy]phenoxy]-3-(2-pyridylmethylamino)propan-2-ol | 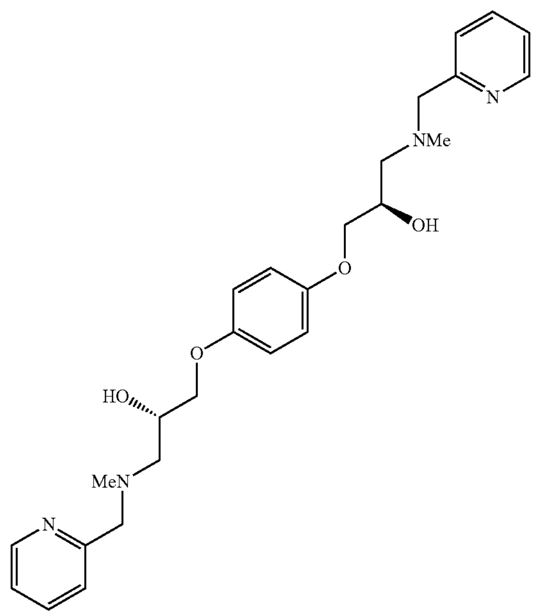 [SMILES: CN(Cc1ccccn1)C[C@H](O)COc1ccc(OC[C@H](O)CN(C)Cc2ccccn2)cc1] | |
| IUPAC Name: 3-[5-[(4-hydroxyphenyl)methylidene]-4-oxo-2-sulfanylidene-1,3-thiazolidin-3-yl]propanoic acid | 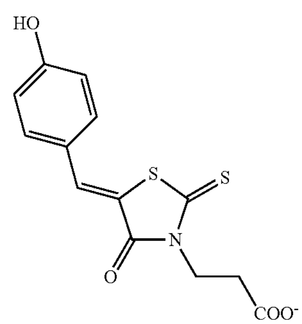 | |
| 2-(1-benzothiazol-2-ylaminoiminoethyl-azo)benzoic | 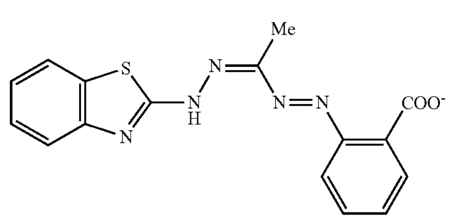 | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 2-[(3-acetylphenyl)-carbamoyl]bicycle-[2.2.1]hept-5-ene-3-carboxylate | 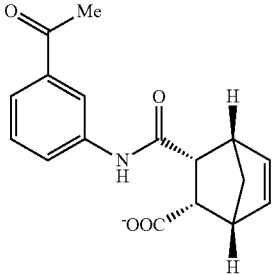 | |
| IUPAC Name: 2-(1H-indazol-5-yliminomethyl)-6-nitrophenolate | 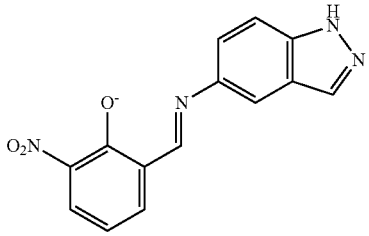 [SMILES: O=[N+]([O-])c1cccc(/C=N/c2ccc3[nH]ncc3c2)c1[O-]] | |
| IUPAC Name: 2-bromo-6-[(1H-indazol-5-ylamino)-methylidene]-4-nitrocyclohexa-2,4-dien-1-one | 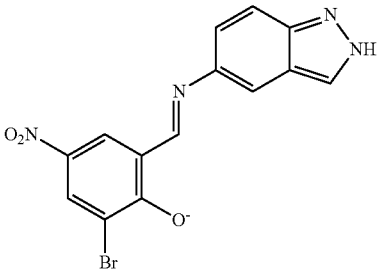 [SMILES: O=[N+]([O-])c1cc(Br)c([O-])c(/C=N/c2ccc3n[nH]cc3c2)c1] | |
| IUPAC Name: 2-(1H-indazol-5-yliminomethyl)-6-methoxy-4-nitrophenolate | 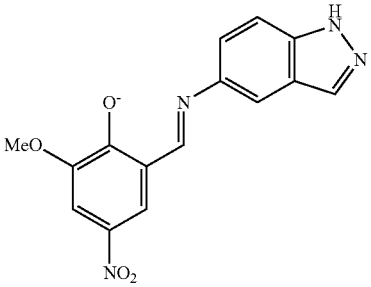 [SMILES: COc1cc([N+](=O)[O-])cc(/C=N/c2ccc3[nH]ncc3c2)c1[O-]] | |

TABLE 1-continued small inhibitory compounds assayed for inhibitory activity against MKK4:

| name | Structure | Inhibition, relative activity of MKK4 compared to control (without additional compound) (%) |
| --- | --- | --- |
| N-{2-[2-(1-methyl-4-piperidinylidene)-hydrazino]-2-oxoethyl}-N-(3-nitrophenyl)benzene sulfonamido (non-preferred name) | 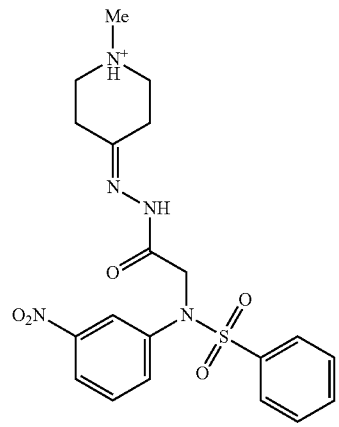 | |
| IUPAC Name: 4-[5-(naphthalen-1-ylmethylidene)-4-oxo-2-sulfanylidene-1,3-thiazolidin-3-yl]butanoate | 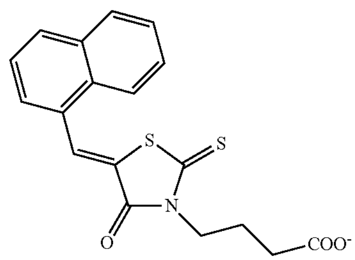 | |
| IUPAC Name: 5-amino-3-[(Z)-1-cyano-2-[3-[(4-methoxy-6-piperidin-1-yl-1,3,5-triazin-2-yl)oxy]phenyl]ethenyl]-1-(2-hydroxyethyl)pyrazole-4-carbonitrile | 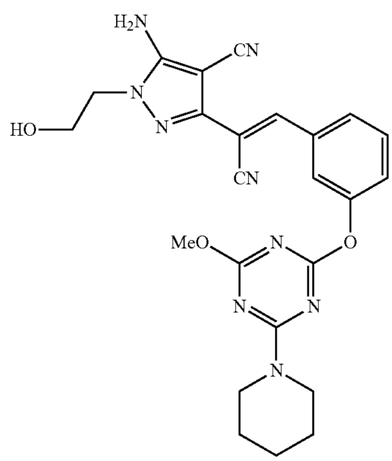 [SMILES: COc1nc(Oc2cccc(/C=C(\C#N)c3nn(CCO)c(N)c3C#N)c2)nc(N2CCCCC2)n1] | |
| IUPAC Name: 8-[2-methoxy-4-[(1-oxo-[1,3]thiazolo[3,2-a]benzimidazol-2-ylidene)methyl]phenoxy]-1,3,7-trimethylpurine-2,6-dione | 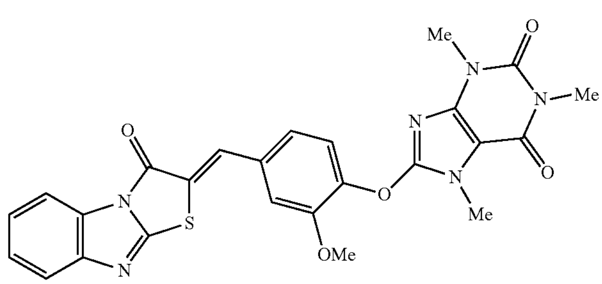 [SMILES: COc1cc(/C=c2\sc3nc4ccccc4n3c2=O)ccc1Oc1nc2c(c(=O)n(C)c(=O)n2C)n1C] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 2-[2-[2-(4-methylphenyl)sulfonylethoxy]ethoxy]ethyl 4-methylbenzene-sulfonate | 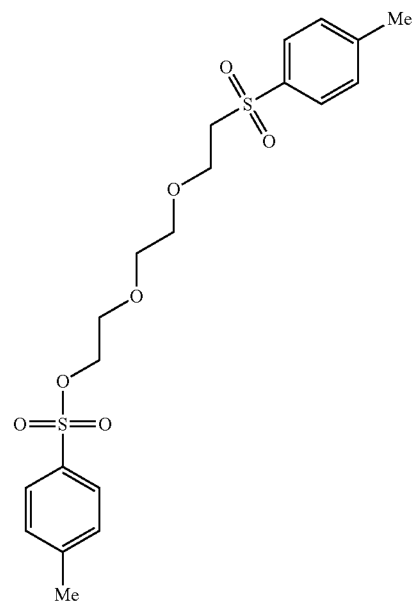 [SMILES: Cc1ccc(S(=O)(=O)CCOCCOCCOS(=O)(=O)c2ccc(C)cc2)cc1] | |
| IUPAC Name: (2S)-3-acetyl-4-hydroxy-1-(4-hydroxyphenyl)-2-phenyl-2H-pyrrol-5-one | 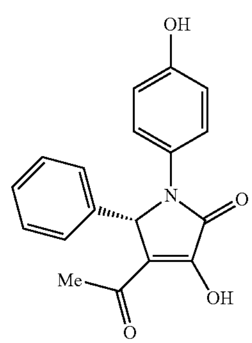 [SMILES: CC(=O)C1=C(O)C(=O)N(c2ccc(O)cc2)[C@H]1c1ccccc1] | |
| IUPAC Name: bis[2-(3,4-dimethylphenyl)-2-oxoethyl] cyclohexane-1,2-dicarboxylate | 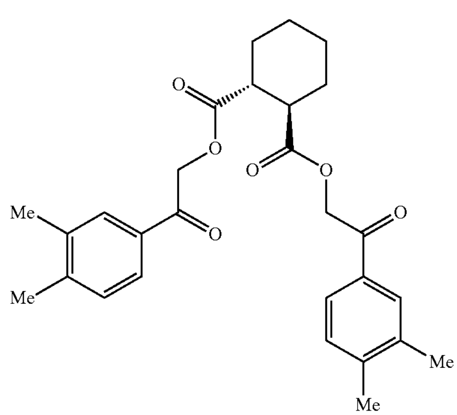 [SMILES: Cc1ccc(C(=O)COC(=O)[C@@H]2CCCC[C@H]2C(=O)OCC(=O)c2ccc(C)c(C)c2)cc1C] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 8-(butoxymethyl)-3-[2-[[5-(2-chlorophenyl)-1H-1,2,4-triazol-3-yl]sulfanyl]acetyl]-3-methyl-2,7-dioxaspiro[4.4]nonane-1,6-dione | 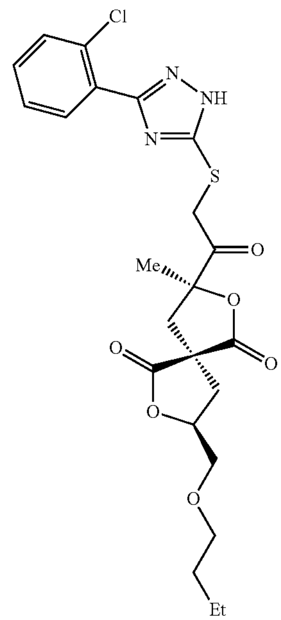 | |
| IUPAC Name: 2-(naphthalen-2-ylsulfonylamino)butanoic acid | 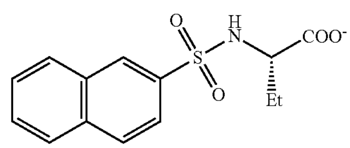 | |
| 1-(3,5-dimethoxyphenyl)-N-[(2-nitrophenyl)methyl]methanamine | 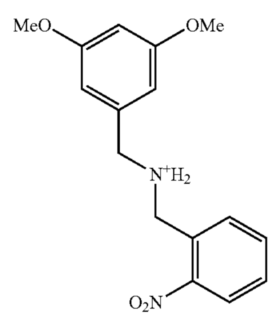 | |

TABLE 1-continued small inhibitory compounds assayed for inhibitory activity against MKK4:

| name | Structure | Inhibition, relative activity of MKK4 compared to control (without additional compound) (%) |
| --- | --- | --- |
| IUPAC Name: 5-[(2-carboxylatophenyl)sulfamoyl]-2-(3-carboxylatopropyl-amino)benzoate | 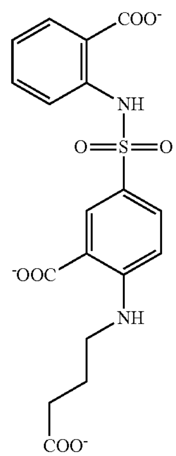 | |
| IUPAC Name: 2-(7H-purin-6-ylazaniumyl)acetate | 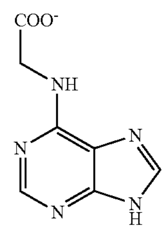 | |
| IUPAC Name: [2-(4-bromophenyl)-2-oxoethyl]6-(5-methyl-2-oxo-1,3-dihydroimidazol-4-yl)-6-oxohexanoate | 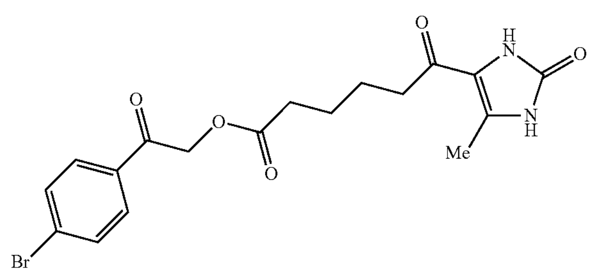 [SMILES: Cc1[nH]c(=O)[nH]c1C(=O)CCCCC(=O)OCC(=O)c1ccc(Br)cc1] | |
| 3-(2,3-dihydro-1H-indol-1-ylcarbonyl)-1,2,2-trimethylcyclopentanecarboxylic acid | | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: benzyl-N-[2-[2-[(4-methoxy-3-nitrophenyl)-methylidene]-hydrazinyl]-2-oxoethyl]-N-methylcarbamate | 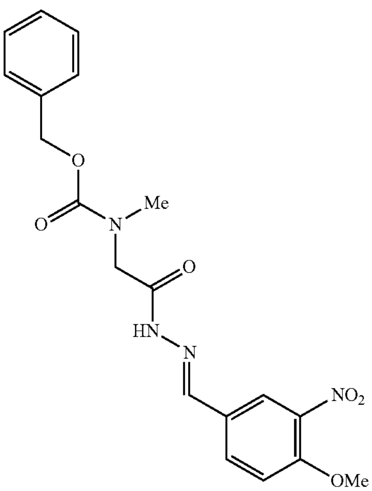 [SMILES: COc1ccc(/C=N/NC(=O)CN(C)C(=O)OCc2ccccc2)cc1[N+](=O)[O-]] | |
| IUPAC Name: methyl4-[[2-[2-[2-[(4-methoxy-4-oxobutyl)amino]-2-oxoethoxy]phenoxy]acetyl]amino]butanoate | 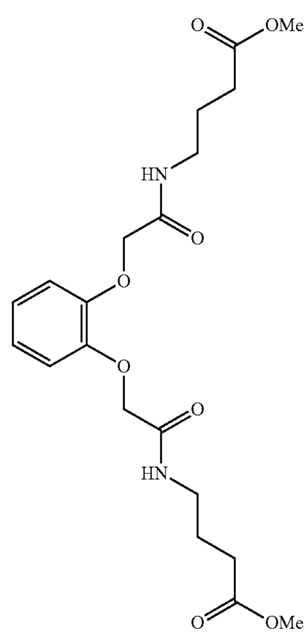 [SMILES: COC(=O)CCCNC(=O)COc1ccccc1OCC(=O)NCCCC(=O)OC] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: [2-acetyloxy-4-[2-[5-(ethoxymethyl)-4-imino-2-methylpyrimidin-1-yl]acetyl]phenyl] acetate | 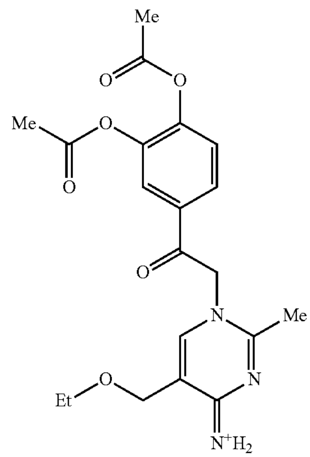 | |
| IUPAC Name: (4-chloro-2-methylphenyl)methyl N-[2-[[4-(dimethylamino)-6-[methoxy(methyl) amino]-1,3,5-triazin-2-yl]oxy] ethyl]carbamate | 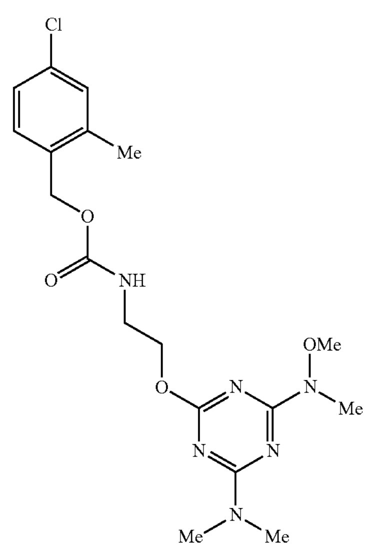 [SMILES: CON(C)c1nc(OCCNC(=O)OCc2ccc(Cl)cc2C)nc(N(C)C)n1] | |

TABLE 1-continued small inhibitory compounds assayed for inhibitory activity against MKK4:

| name | Structure | Inhibition, relative activity of MKK4 compared to control (without additional compound) (%) |
| --- | --- | --- |
| 1-[4-[2-hydroxy-3-(2-nitrophenoxy)-propyl]piperazin-1-yl]-3-(2-nitrophenoxy)-propan-2-ol | 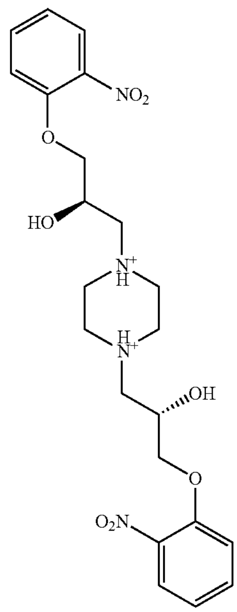 | |
| IUPAC Name: 2-[(5R)-3-(4-hydroxyphenyl)-2,4-dioxo-1,3-thiazolidin-5-yl]acetate | 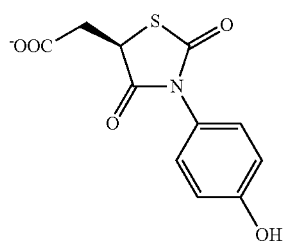 | |
| IUPAC Name: 2-[2-(2,4-dihydroxyphenyl)-2-oxoethyl]sulfanyl-4-hydroxy-1H-pyrimidin-6-one | 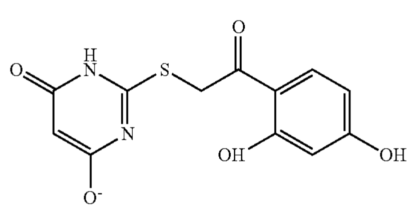 [SMILES: O=C(CSc1nc([O-])cc(=O)[nH]1)c1ccc(O)cc1O] | |
| IUPAC Name: 4-hydroxy-2-[2-(1H-indol-3-yl)-2-oxoethyl]sulfanyl-1H-pyrimidin-6-one | 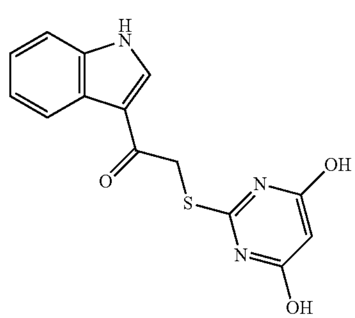 [SMILES: O=C(CSc1nc(O)cc(O)n1)c1c[nH]c2ccccc12] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 3-(3-anilino-2-hydroxypropyl)-1-[[3-(3-anilino-2-hydroxypropyl)-5,5-dimethyl-2,4-dioxoimidazolidin-1-yl]methyl]-5,5-dimethylimidazolidine-2,4-dione | 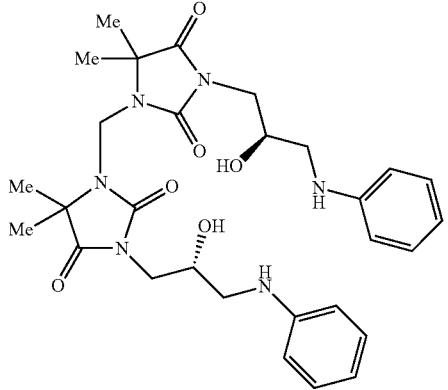 [SMILES: CC1(C)C(=O)N(C[C@H](O)CNc2ccccc2)C(=O)N1CN1C(=O)N(C[C@H](O)CNc2ccccc2)C(=O)C1(C)C] | |
| 1-(2-furylmethyl)-4-(3-nitrobenzyl)-piperazine | 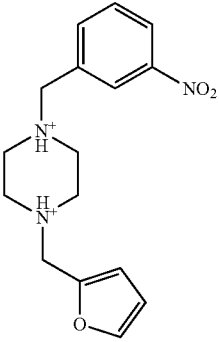 | |
| IUPAC Name: 2-nitro-6-[(5-pyridin-4-yl-1,3,4-thiadiazol-2-yl)carbamoyl] benzoic acid | 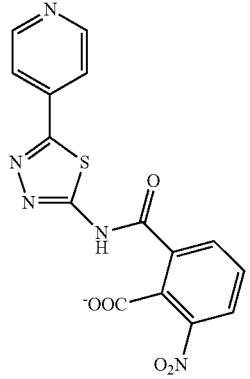 | |

TABLE 1-continued small inhibitory compounds assayed for inhibitory activity against MKK4:

| name | Structure | Inhibition, relative activity of MKK4 compared to control (without additional compound) (%) |
| --- | --- | --- |
| IUPAC Name: [2-[[[2-(4-phenylphenoxy)acetyl]hydrazinylidene]methyl]phenyl] acetate | 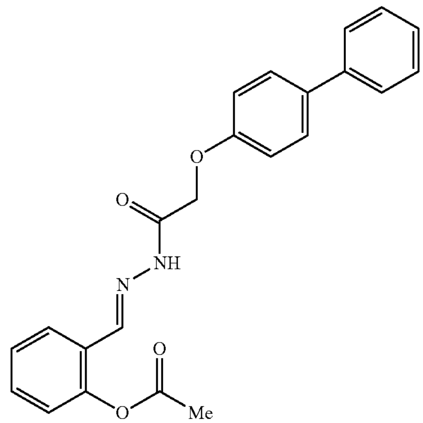 [SMILES: CC(=O)Oc1ccccc1/C=N/NC(=O)COc1ccc(-c2ccccc2)cc1] | |
| 2-((4'-HYDROXY-NAPHTHYL)-AZO)BENZOIC ACID | 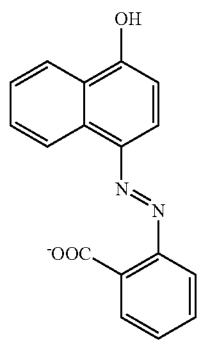 | |
| 8-hydroxy-5,6-dihydro-4H-11-oxa-6a-azabenzo[de]anthracene-7,10-dione | 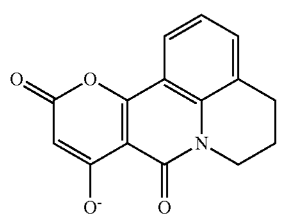 [SMILES: O=c1cc([O-])c2c(=O)n3c4c(cccc4c2o1)CCC3] | |
| IUPAC Name: 2-(pyridin-3-ylmethylcarbamoyl)bicyclo[2.2.1]hept-5-ene-3-carboxylate | 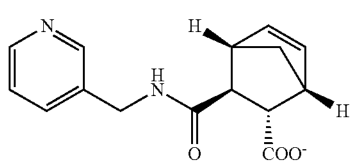 | |
| 4-Ethyl-5-(4-hydroxyphenyl)-4H-[1,2,4]triazol-3-ylsulfanyl]-acetic acid | 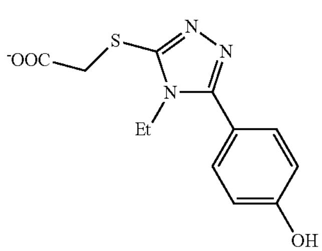 | |

TABLE 1-continued small inhibitory compounds assayed for inhibitory activity against MKK4:

| name | Structure | Inhibition, relative activity of MKK4 compared to control (without additional compound) (%) |
| --- | --- | --- |
| IUPAC Name: 5-[[4-(benzylamino)-3-nitrophenyl]sulfonylamino]benzene-1,3-dicarboxylate | 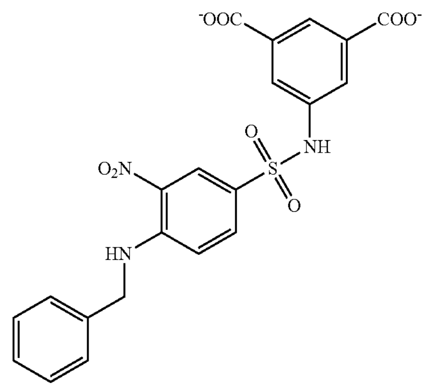 | |
| IUPAC Name: 4-[4-(4-carboxylato-phenoxy)phenyl]-sulfonylphthalate | 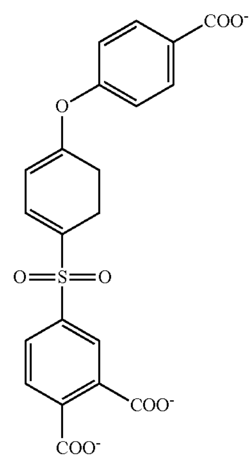 | |
| N-[(2,4-dihydroxyphenyl)-methyleneamino]-2-[(8-methoxy-2-methyl-4-quinolyl)-sulfanyl]acetamide | 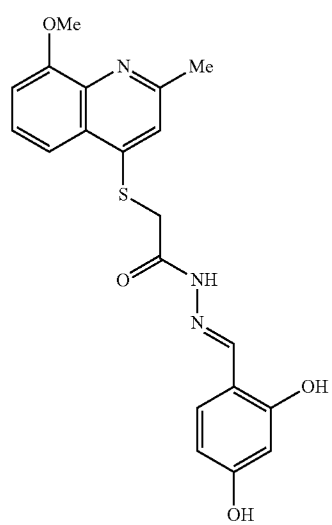 [SMILES: COc1cccc2c(SCC(=O)N/N=C/c3ccc(O)cc3O)cc(C)nc12] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 1-[2-[2-[2-[2-(2-acetyl-phenoxy)ethoxy]-ethoxy]ethoxy]-phenyl]ethanone | 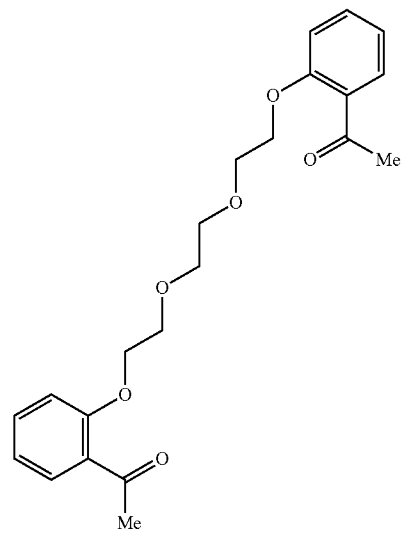 [SMILES: CC(=O)c1ccccc1OCCOCCOCCOc1ccccc1C(C)=O] | |
| IUPAC Name: [2-[4-(4-chloro-2-nitro-phenoxy)phenyl]-2-oxoethyl] 2-benzamidoacetate | 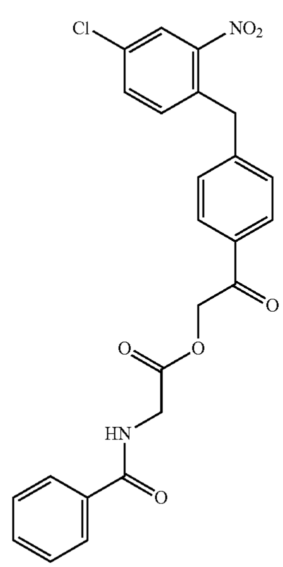 [SMILES: O=C(CNC(=O)c1ccccc1)OCC(=O)c1ccc(Cc2ccc(Cl)cc2[N+](=O)[O-])cc1] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: phenacyl 3-[phenacyl-(phenacylamino)-amino]benzoate | 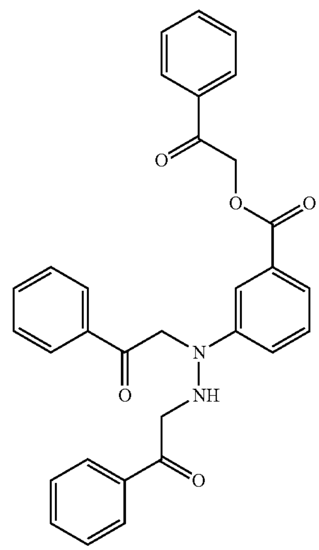 [SMILES: O=C(CNN(CC(=O)c1ccccc1)c1cccc(C(=O)OCC(=O)c2ccccc2)c1)c1ccccc1] | |
| IUPAC Name: 1-(4-amino-1,2,5-oxadiazol-3-yl)-5-(1H-benzimidazol-2-ylsulfanylmethyl)-N-[1-(5-nitrofuran-2-yl)ethylideneamino]-triazole-4-carboxamide | 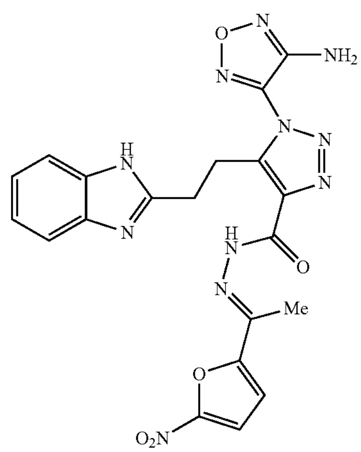 [SMILES: C/C(=N\NC(=O)c1nnn(-c2nonc2N)c1CCc1nc2ccccc2[nH]1)c1ccc([N+](=O)[O-])o1] | |
| IUPAC Name: 2-benzamido-N-[1-(furan-2-ylmethylamino)-1-oxopropan-2-yl]benzamide | 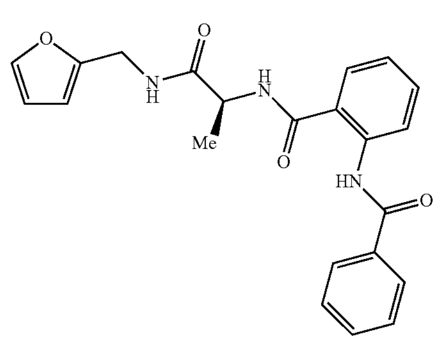 [SMILES: C[C@H](NC(=O)c1ccccc1NC(=O)c1ccccc1)C(=O)NCc1ccco1] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 2-benzamido-N-[1-(3-imidazol-1-ylpropylamino)-1-oxo-3-phenylpropan-2-yl]benzamide | 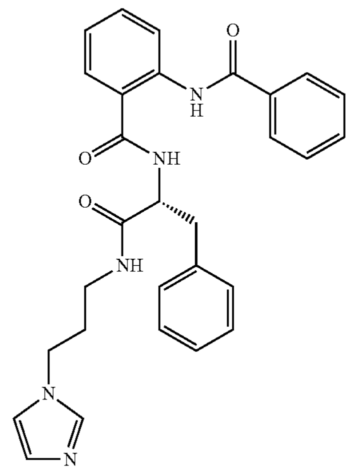 [SMILES: O=C(Nc1ccccc1C(=O)N[C@H](Cc1ccccc1)C(=O)NCCCn1ccnc1)c1ccccc1] | |
| IUPAC Name: ethyl2-[[2-[2-(2,3-dioxoindol-1-yl)acetyl]oxyacetyl]-amino]-4-methyl-1,3-thiazole-5-carboxylate | 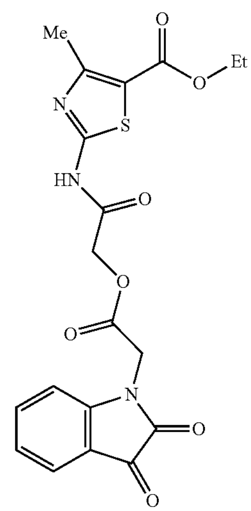 [SMILES: CCOC(=O)c1sc(NC(=O)COC(=O)CN2C(=O)C(=O)c3ccccc32)nc1C] | |
| IUPAC Name: ethyl5-[[5-ethoxycarbonyl-3-(2-methoxy-2-oxoethyl)-4-methyl-1H-pyrrol-2-yl]methyl]-4-(3-methoxy-3-oxopropyl)-3-methyl-1H-pyrrole-2-carboxylate | 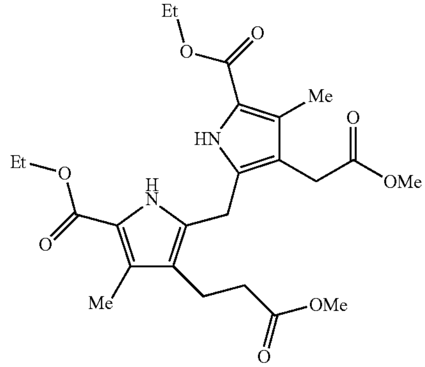 [SMILES: CCOC(=O)c1[nH]c(Cc2[nH]c(C(=O)OCC)c(C)c2CC(=O)OC)c(CCC(=O)OC)c1C] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: ethyl2-[[2-(1H-benzimidazol-2-ylsulfanyl)acetyl]-amino]-6-methyl-5,7-dihydro-4H-thieno[2,3-c]pyridine-3-carboxylate | 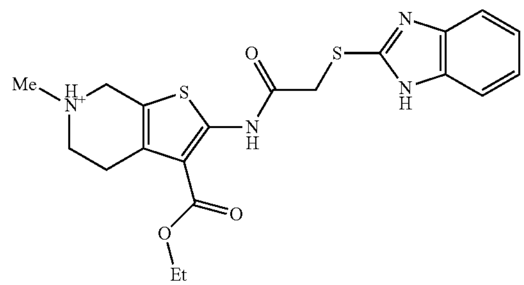 | |
| keto(3-pyridyl-methylcarbamoyl)-BLAHolate | 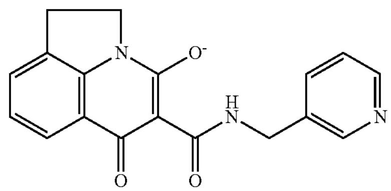 [SMILES: O=C(NCc1cccnc1)c1c([O-])n2c3c(cccc3c1=O)CC2] | |
| keto(4-pyridylmethyl-carbamoyl)BLAH-olate | 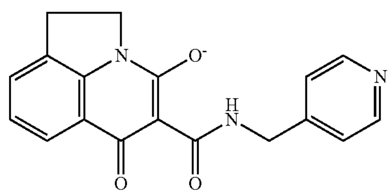 [SMILES: O=C(NCc1ccncc1)c1c([O-])n2c3c(cccc3c1=O)CC2] | |
| hydroxy-oxo-N-(4-pyridyl)BLAH-carboxamide | 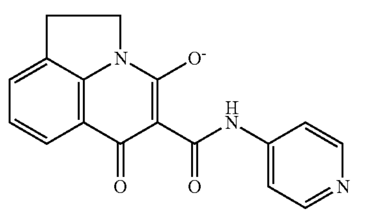 [SMILES: O=C(Nc1ccncc1)c1c([O-])n2c3c(cccc3c1=O)CC2] | |
| IUPAC Name: 3-[[(5R)-2,4-dioxo-1,3-thiazolidin-5-yl]amino]benzoate | 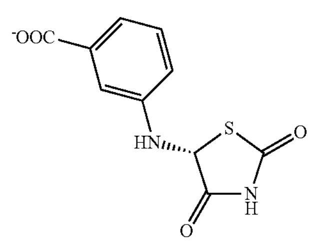 | |
| methyl N-acetyl-5-(1,3-dioxo-1,3-dihydro-2H-isoindol-2-yl)-2-(2H-tetrazol-5-yl)norvalinate | 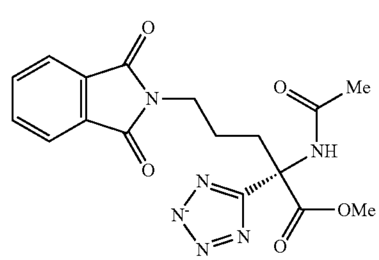 [SMILES: COC(=O)[C@@](CCCN1C(=O)c2ccccc2C1=O)(NC(C)=O)c1nn[n-]n1] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 3-[(2,3-dioxo-1,4-dihydroquinoxalin-6-yl)sulfonyl]propanoate | 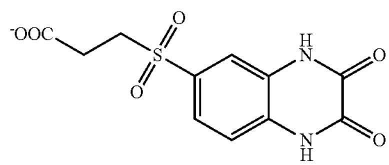 | |
| IUPAC Name: N-[2-(3,4-dimethoxyphenyl)ethyl]-2-[[5-[(4,6-dimethylpyrimidin-2-yl)sulfanylmethyl]-1,3,4-oxadiazol-2-yl]-sulfanyl]acetamide | | |
| IUPAC Name: (2S)-1-(2,1,3-benzothiadiazol-4-ylsulfonyl)piperidine-2-carboxylic acid | 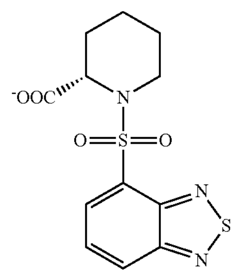 | |
| benzyl(veratryl)-BLAH | 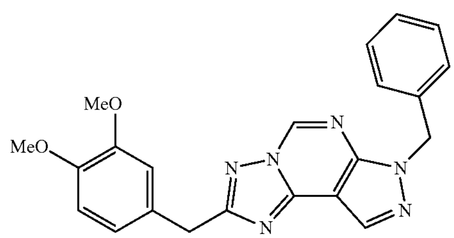 [SMILES: COc1ccc(Cc2nc3c4cnn(Cc5ccccc5)c4ncn3n2)cc1OC] | |
| IUPAC Name: 2-[1-(1,3-benzodioxol-5-yl)-2,5-dioxopyrrolidin-3-yl]sulfanylpyridine-3-carboxylate | 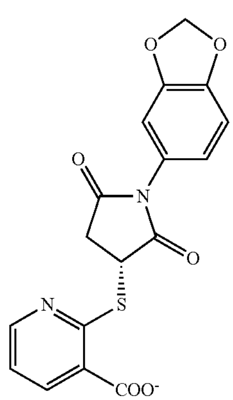 | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 2-[4-(5-acetyl-1-hydroxy-4-methylimidazol-2-yl)-2-ethoxy-phenoxy]-N-(3-methylphenyl)-acetamide | 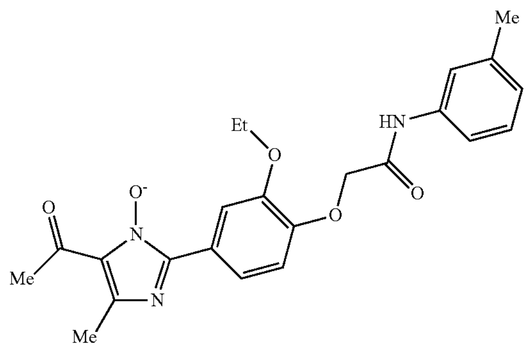 [SMILES: CCOc1cc(-c2nc(C)c(C(C)=O)n2[O-])ccc1OCC(=O)Nc1cccc(C)c1] | |
| (3-chlorophenyl)-keto-BLAH-carboxylate | 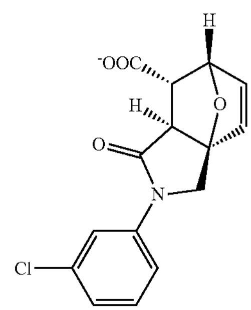 | |
| 1-naphthyl-oxo-BLAHcarboxylic acid | 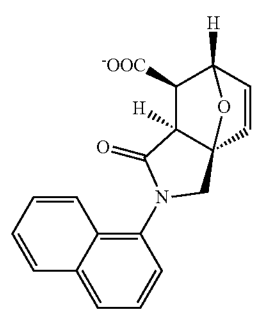 | |
| IUPAC Name: 2-(3,4-dimethoxyphenyl)-1-[4-(2-fluorophenyl)-piperazin-1-yl]ethanone | 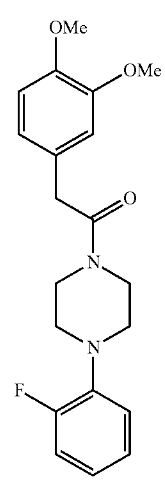 [SMILES: COc1ccc(CC(=O)N2CCN(c3ccccc3F)CC2)cc1OC] | |

TABLE 1-continued small inhibitory compounds assayed for inhibitory activity against MKK4:

| name | Structure | Inhibition, relative activity of MKK4 compared to control (without additional compound) (%) |
| --- | --- | --- |
| IUPAC Name: 4-(4-ethoxyphenyl)-5-pyridin-4-yl-1,2,4-triazole-3-thiolate | 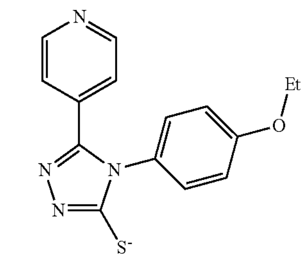 [SMILES: CCOc1ccc(-n2c([S-])nnc2-c2ccncc2)cc1] | |
| IUPAC Name: 4-(3-methylphenyl)-5-pyridin-4-yl-1,2,4-triazole-3-thiolate | 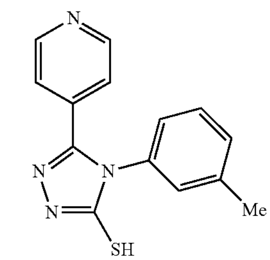 [SMILES: Cc1cccc(-n2c(S)nnc2-c2ccncc2)c1] | |
| IUPAC Name: ethyl 2-(2-benzyl-sulfonylbenzimidazol-1-yl)acetate | | |
| IUPAC Name: 2-[(3S)-1-(1,3-benzodioxol-5-yl)-2,5-dioxopyrrolidin-3-yl]sulfanyl-benzoate | 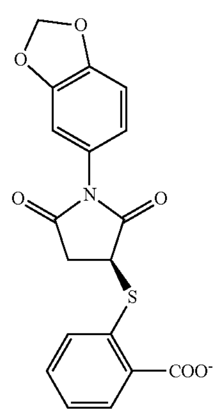 | |

TABLE 1-continued small inhibitory compounds assayed for inhibitory activity against MKK4:

| name | Structure | Inhibition, relative activity of MKK4 compared to control (without additional compound) (%) |
|---|---|---|
| Popular Name: 1-[3-(3-methoxyphenoxy)propyl]-4-[(4-methylphenyl)-sulfonyl]piperazine | | |
| IUPAC Name: 3-(pyridin-3-ylmethyl-amino)benzoic acid | 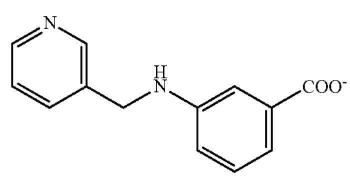 | |
| 2-(4-hydroxyphenyl)quinoline-4-carboxylic acid | | |
| IUPAC Name: 6-(2-pyridin-4-ylethylcarbamoyl)cyclohex-3-ene-1-carboxylate | 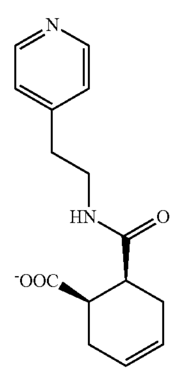 | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 2-[(3S)-1-(4-hydroxyphenyl)-2,5-dioxopyrrolidin-3-yl]sulfanylbenzoate | 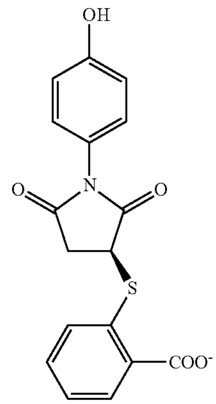 | |
| IUPAC Name: 4-(4-methoxyphenyl)-5-pyridin-4-yl-1,2,4-triazole-3-thiolate | 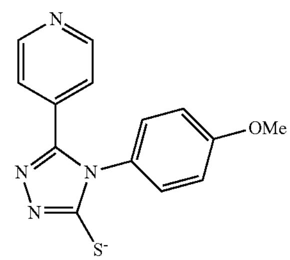 [SMILES: COc1ccc(-n2c([S-])nnc2-c2ccncc2)cc1] | |
| IUPAC Name: ethyl 5-[(2R)-3-(3,5-dimethylpyrazol-1-yl)-2-hydroxy-propoxy]-1,2-dimethylindole-3-carboxylate | 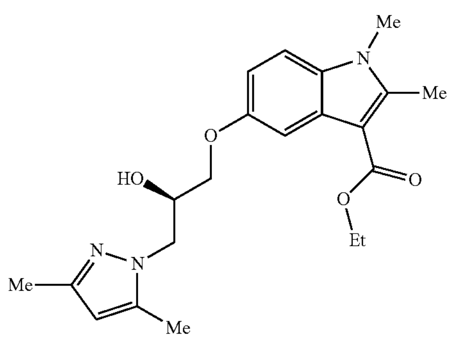 [SMILES: CCOC(=O)c1c(C)n(C)c2ccc(OC[C@H](O)Cn3nc(C)cc3C)cc12] | |
| IUPAC Name: 1-naphthalen-2-yl-sulfonylpyrrolidine-2-carboxylic acid | 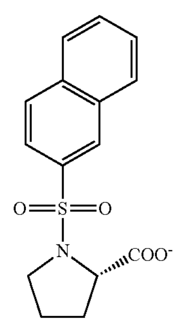 | |
| IUPAC Name: (2S)-2-[(2,3-dioxo-1,4-dihydroquinoxalin-6-yl)sulfonyl-amino]propanoate | 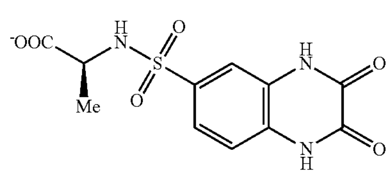 | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: (2R)-3-acetyl-4-hydroxy-1-[2-(1H-indol-3-yl)ethyl]-2-pyridin-2-yl-2H-pyrrol-5-one | 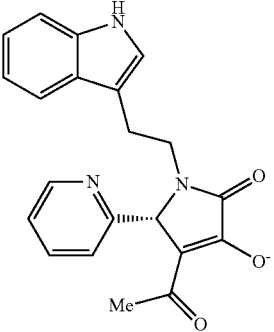 [SMILES: CC(=O)C1=C([O-])C(=O)N(CCc2c[nH]c3ccccc23)[C@H]1c1ccccn1] | |
| .2.1.0%1,5&]dec-8-ene-6-carboxylic acid | 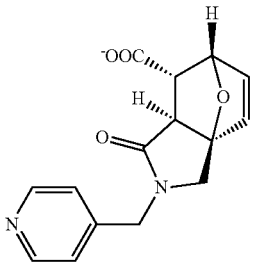 | |
| IUPAC Name: (3S)-3-(1H-indol-3-yl)-3-pyridin-4-ylpropanoic acid | 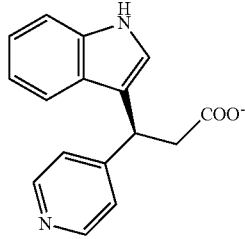 | |
| IUPAC Name: 5-methyl-2-pyridin-4-yl-1H-[1,2,4]triazolo[1,5-a]pyrimidin-7-one | 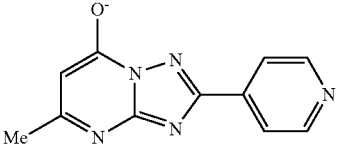 [SMILES: Cc1cc([O-])n2nc(-c3ccncc3)nc2n1] | |
| IUPAC Name: (2S)-1-(1-methyl-2-oxobenzo[cd]indol-6-yl)sulfonyl-pyrrolidine-2-carboxylic acid | 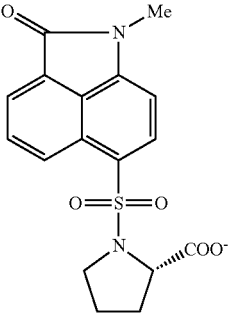 | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: [2-[4-(furan-2-carbonyloxy)phenyl]-2-oxoethyl] 1-(furan-2-ylmethyl)-5-oxopyrrolidine-3-carboxylate | 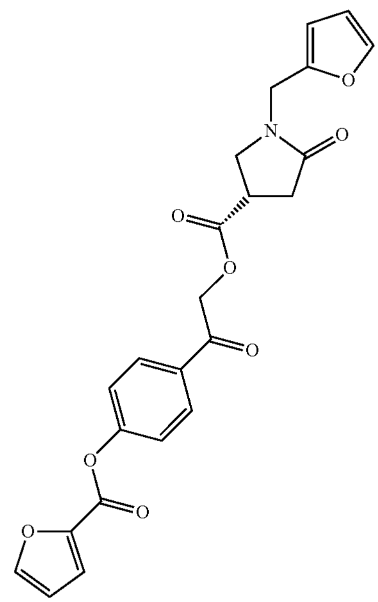 | |
| IUPAC Name: 4-[2-[5-(4-methoxyphenyl)-1H-pyrazol-4-yl]ethenyl]-6-(trifluoromethyl)-1H-pyrimidin-2-one | 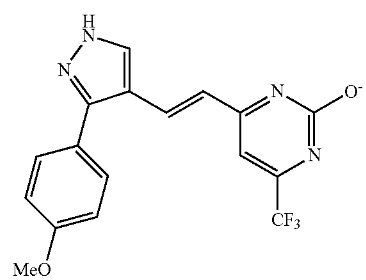 [SMILES: COc1ccc(-c2n[nH]cc2/C=C/c2cc(C(F)(F)F)nc([O-])n2)cc1] | |
| IUPAC Name: 2-hydroxy-5-[[(E)-(3-methyl-5-oxo-1H-pyrazol-4-ylidene)-methyl]amino]-benzoate | 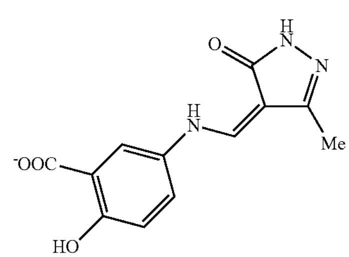 | |
| IUPAC Name: 3-oxo-2-(pyridin-4-ylmethyl)-1H-isoindole-4-carboxylate acid | 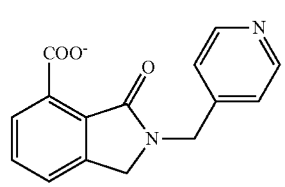 | |
| 8-hydroxy-[1]benzofuran[3,2-b]quinoline-11-carboxylic acid | 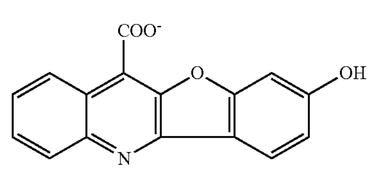 | |

TABLE 1-continued
small inhibitory compounds assayed for inhibitory activity against MKK4:
| name | Structure | Inhibition, relative activity of MKK4 compared to control (without additional compound) (%) |
|---|---|---|
| IUPAC Name: 5-[[3-methoxy-4-(thiophen-2-ylmethoxy)phenyl]methylamino]-2-morpholin-4-ylbenzoate | 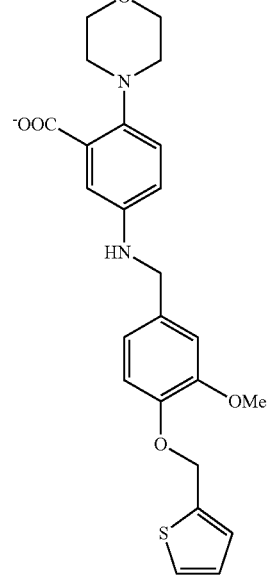 | |
| oxylic acid | 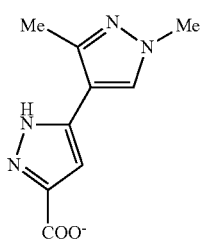 | |
| (3R)-4-keto-3-morpholin-4-ium-4-yl-4-(2-phenoxy-ethoxy)butyrate | 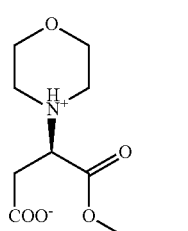 | |

TABLE 1-continued small inhibitory compounds assayed for inhibitory activity against MKK4:

| name | Structure | Inhibition, relative activity of MKK4 compared to control (without additional compound) (%) |
|---|---|---|
| (3R)-4-keto-3-morpholin-4-ium-4-yl-4-[[(2S)-tetrahydrofuran-2-yl]methoxy]butyrate | 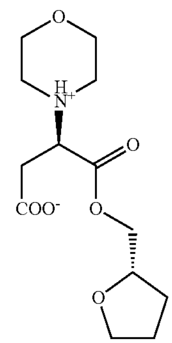 | |
| 4-oxo-4-[2-[4-(p-tolylsulfonyl)-piperazin-1-yl]ethoxy]butanoic acid | 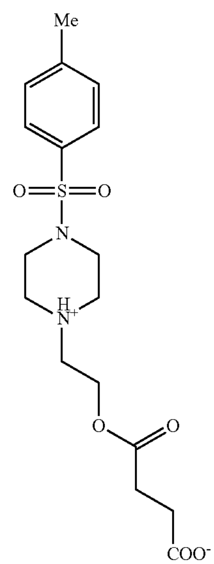 | |
| IUPAC Name: 4-(3-chloro-4-fluorophenyl)-3-pyridin-4-yl-1H-1,2,4-triazole-5-thione | 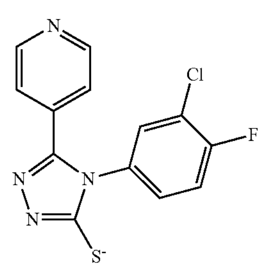 [SMILES: Fc1ccc(-n2c([S-])nnc2-c2ccncc2)cc1Cl] | |
| 3-[3-(4-pyridyl)-5-thioxo-1H-1,2,4-triazol-4-yl]benzoic | 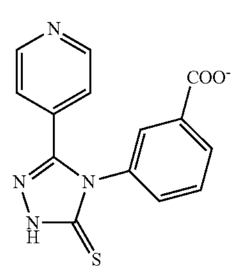 | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 1-(3-phenyl-adamantane-1-carbonyl)pyrrolidine-2-carboxylic acid | 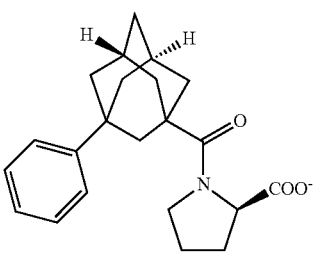 | |
| IUPAC Name: 4-(2,3-dihydro-1,4-benzodioxin-6-yl)-3-(3-hydroxyphenyl)-1H-1,2,4-triazole-5-thione | 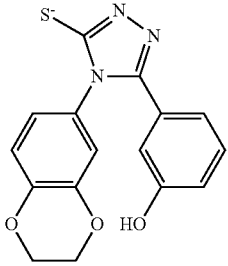 [SMILES: Oc1cccc(-c2nnc([S-])n2-c2ccc3c(c2)OCCO3)c1] | |
| (dimethylBLAHyl)-methyl | 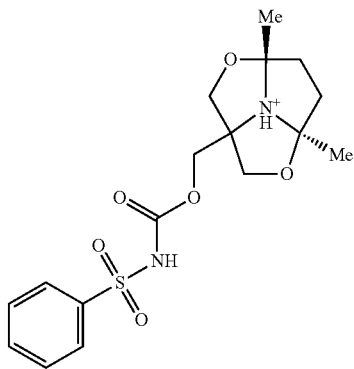 | |
| IUPAC Name: N-[1-(3-imidazol-1-ylpropylamino)-3-methyl-1-oxobutan-2-yl]-2-[(4-methoxy-benzoyl)amino]benzamide | 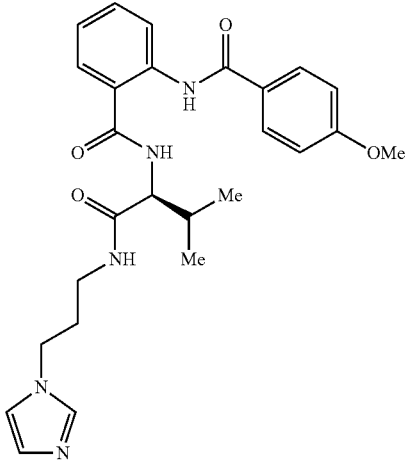 [SMILES: CC[C@H](NC(=O)c1ccccc1NC(=O)c1ccc(OC)cc1)C(=O)NCCCn1ccnc1 ; "Me"] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 1-ethyl-3-methyl-2-oxoquinoxaline-6-carboxylate | 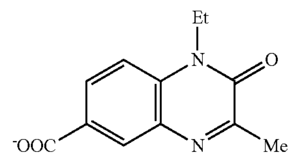 | |
| IUPAC Name: 3-(4-oxo-2H-pyrazolo[3,4-d]pyrimidin-1-yl)propanoate | 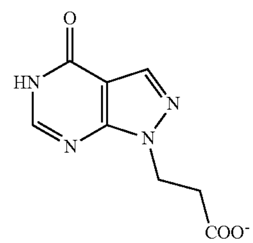 | |
| 3-(benzotriazol-1-yl)-1-[(3R)-3-[4-(3-methylisoxazol-5-yl)-2H-pyrazol-3-yl]-1-piperidyl]-propan-1-one | 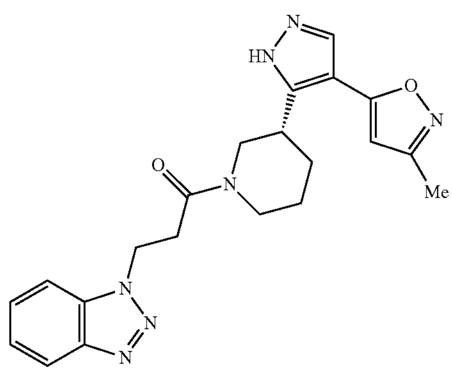 [SMILES: Cc1cc(-c2cn[nH]c2[C@@H]2CCCN(C(=O)CCn3nnc4ccccc43)C2)on1] | |
| IUPAC Name: N-[2-(5-oxo-4-phenyltetrazol-1-yl)ethyl]-2-(4-oxo-3H-phthalazin-1-yl)acetamide | 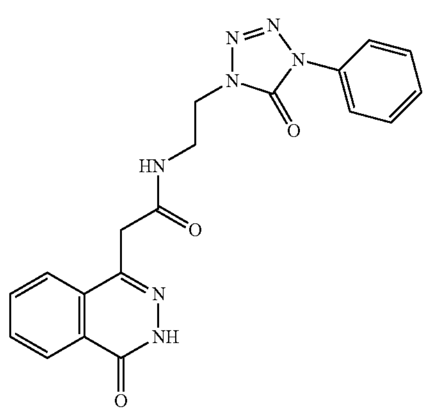 [SMILES: O=C(Cc1n[nH]c(=O)c2ccccc12)NCCn1nnn(-c2ccccc2)c1=O] | |
| IUPAC Name: ethyl4-[[4-(7-amino-2-methyl-pyrazolo[1,5-a]pyrimidin-5-yl)piperidin-1-yl]methyl]-3,5-dimethyl-1H-pyrrole-2-carboxylate | 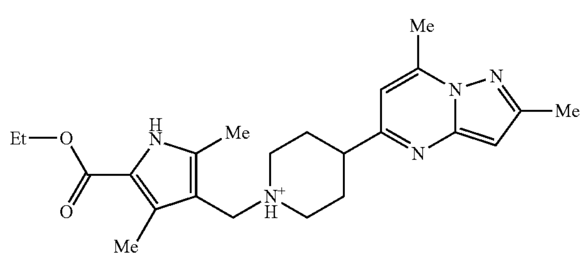 | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: [4-(4-methyl-5-pyrimidin-4-yl-1,3-thiazol-2-yl)piperidin-1-yl]-(1H-1,2,4-triazol-5-yl)methanone | 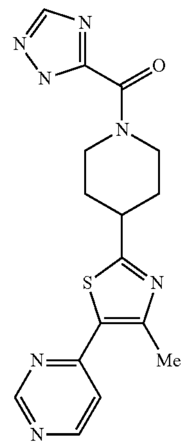 [SMILES: Cc1nc(C2CCN(C(=O)c3ncn[nH]3)CC2)sc1-c1ccncn1] | |
| IUPAC Name: 3-methyl-1-phenyl-5-[(2-pyrrolidin-1-ylsulfonylethylamino)methyl]-2H-pyrazolo[3,4-b]pyridin-6-one | 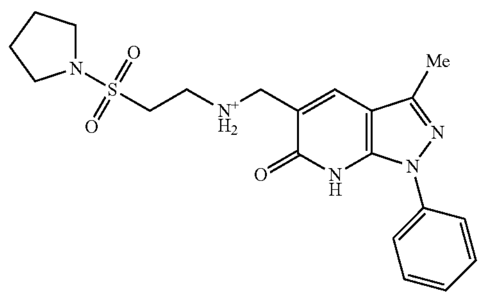 | |
| 1-[2-(4-methoxyphenyl)pyrimidin-5-yl]-N-methyl-N-(4,5,6,7-tetrahydro-1H-indazol-3-ylmethyl)methanamine | | |
| IUPAC Name: N-[[2-(4-methoxyphenyl)pyrimidin-5-yl]methyl]-N-methyl-1-pyridin-2-ylpropan-2-amine | 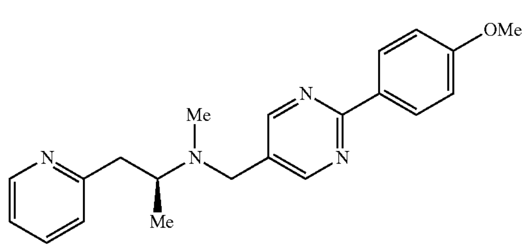 [SMILES: COc1ccc(-c2ncc(CN(C)[C@@H](C)Cc3ccccn3)cn2)cc1] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: N-methyl-N-(2-phenoxyethyl)-2-quinazolin-4-yloxyacetamide | 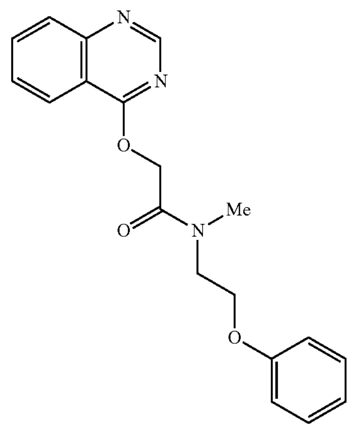 [SMILES: CN(CCOc1ccccc1)C(=O)COc1ncnc2ccccc12] | |
| IUPAC Name: N-[2-[4-(4-fluorophenyl)-4-hydroxypiperidin-1-yl]ethyl]-2-[(5-methyl-1,3,4-oxadiazol-2-yl)sulfanyl]-acetamide | 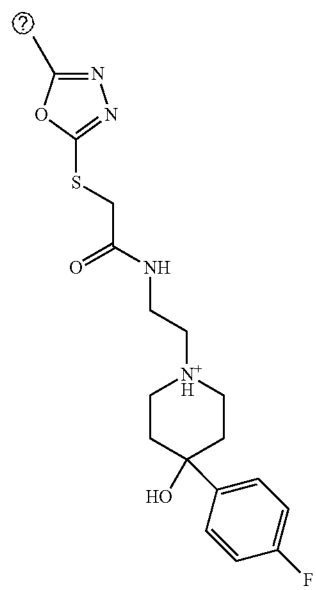 | |
| IUPAC Name: 5-(2-ethoxypyridin-3-yl)-3-[2-(2-propan-2-ylpyrrolo[2,3-b]pyridin-1-yl)ethyl]-1,2,4-oxadiazole | 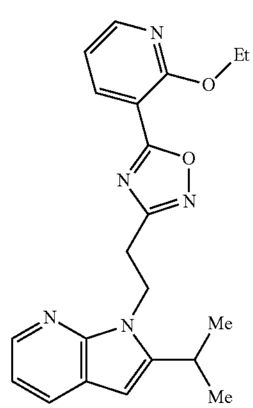 [SMILES: CCOc1ncccc1-c1nc(CCn2c(C(C)C)cc3cccnc32)no1] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: N-[1-(3,4-dihydro-2H-1,5-benzodioxepin-7-yl)-2-methylpropyl]-6-(2-hydroxyethyl)-pyrazolo[1,5-a]pyrimidine-3-carboxamide | 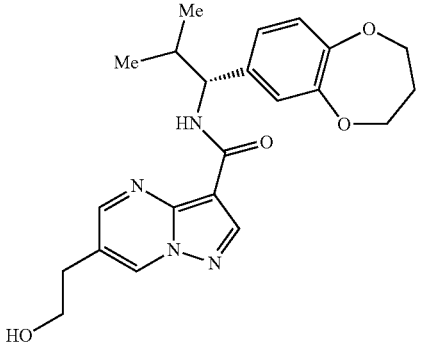 [SMILES: CC(C)[C@@H](NC(=O)c1cnn2cc(CCO)cnc12)c1ccc2c(c1)OCCCO2] | |
| IUPAC Name: N-[2-(1-methyl-benzimidazol-2-yl)ethyl]-2-[2-(3-methyl-1,2,4-oxadiazol-5-yl)phenoxy]-acetamide | 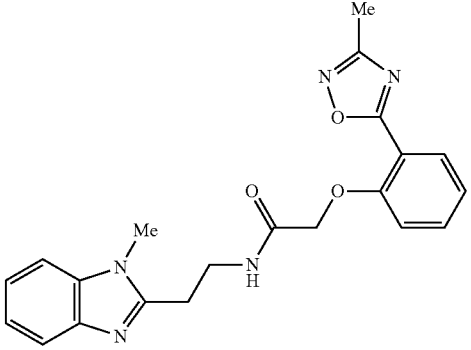 [SMILES: Cc1noc(-c2ccccc2OCC(=O)NCCc2nc3ccccc3n2C)n1] | |
| 2-amino-5-[2-[4-[3-(2,3-dimethyl-phenoxy)propyl]-piperazin-1-yl]-2-oxo-ethyl]-6-methyl-3H-pyrimidin-4- | 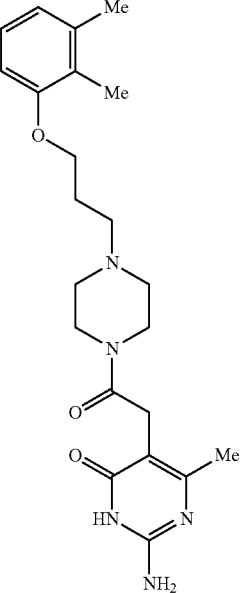 [SMILES: Cc1cccc(OCCCN2CCN(C(=O)Cc3c(C)nc(N)[nH]c3=O)CC2)c1C] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: N-[1-(3,5-dimethyl-pyrazol-1-yl)propan-2-yl]-1-(1,5-dimethylpyrazol-4-yl)sulfonylpiperidine-4-carboxamide | 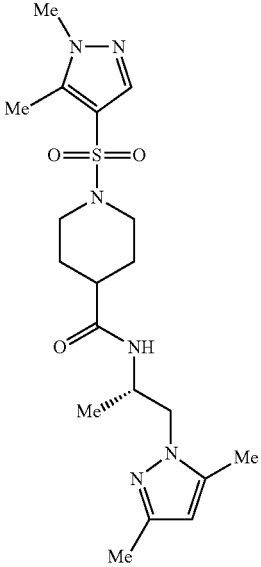 [SMILES: Cc1cc(C)n(CCNC(=O)C2CCN(S(=O)(=O)c3cnn(C)c3C)CC2)n1 ; "Me"] | |
| IUPAC Name: 4-[(3,5-dimethyl-pyrazol-1-yl)methyl]-N-[2-(4-fluorophenoxy)-phenyl]-5-methyl-1,2-oxazole-3-carboxamide | 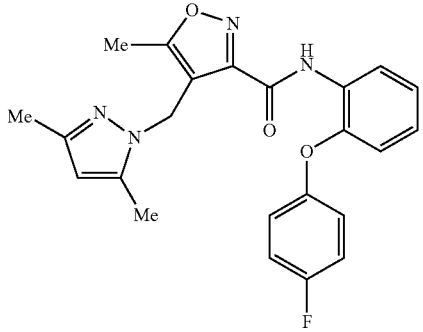 [SMILES: Cc1cc(C)n(Cc2c(C(=O)Nc3ccccc3Oc3ccc(F)cc3)noc2C)n1] | |
| IUPAC Name: 2-(3-methyl-2,6-dioxopurin-7-yl)-N-[1-(7-methyl-1H-indol-3-yl)propan-2-yl]acetamide | 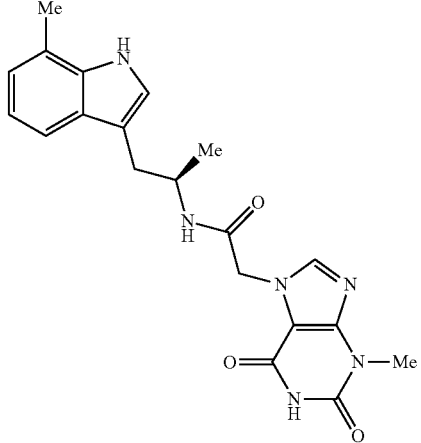 [SMILES: Cc1cccc2c(C[C@@H](C)NC(=O)Cn3cnc4c3c(=O)[nH]c(=O)n4C)c[nH]c12] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 7-bicyclo[4.1.0]-heptanyl-[4-[3-(2-methoxyphenoxy)-propyl]piperazin-1-yl]methanone | 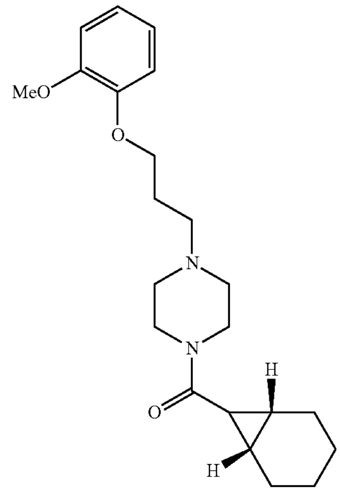 [SMILES: COc1ccccc1OCCCN1CCN(C(=O)C2[C@H]3CCCC[C@@H]23)CC1] | |
| IUPAC Name: 5-[2-(3,5-dimethyl-1H-pyrazol-4-yl)ethyl]-7-oxo-N-phenyl-1H-pyrazolo[1,5-a]pyrimidine-3-carboxamide | 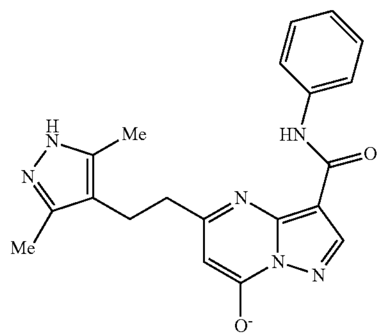 [SMILES: Cc1n[nH]c(C)c1CCc1cc([O-])n2ncc(C(=O)Nc3ccccc3)c2n1] | |
| IUPAC Name: 5-[2-(3,5-dimethyl-1H-pyrazol-4-yl)-ethyl]-3-(4-fluoro-phenyl)-1H-pyrazolo-[1,5-a]pyrimidin-7-one | 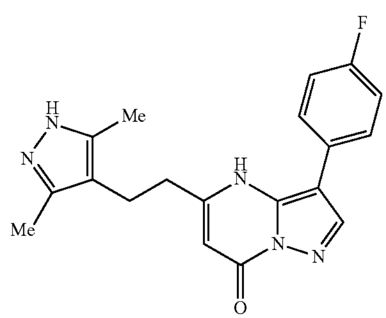 [SMILES: Cc1n[nH]c(C)c1CCc1cc(=O)n2ncc(-c3ccc(F)cc3)c2[nH]1] | |
| IUPAC Name: 5-[2-(3,5-dimethyl-1H-pyrazol-4-yl)ethyl]-3-(4-methylphenyl)-1H-pyrazolo[1,5-a]pyrimidin-7-one | 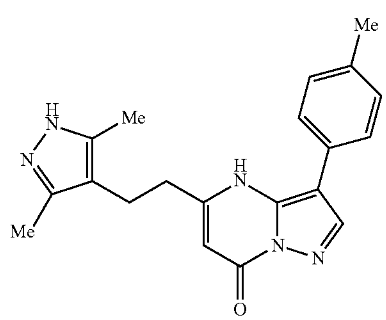 [SMILES: Cc1ccc(-c2cnn3c(=O)cc(CCc4c(C)n[nH]c4C)[nH]c23)cc1] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 5-[2-(3,5-dimethyl-1H-pyrazol-4-yl)-ethyl]-2-(methoxymethyl)-3-phenyl-1H-pyrazolo[1,5-a]pyrimidin-7-one | | |
| IUPAC Name: 3-(4-chlorophenyl)-5-[2-(3,5-dimethyl-1H-pyrazol-4-yl)ethyl]-2-(methoxymethyl)-1H-pyrazolo[1,5-a]pyrimidin-7-one | 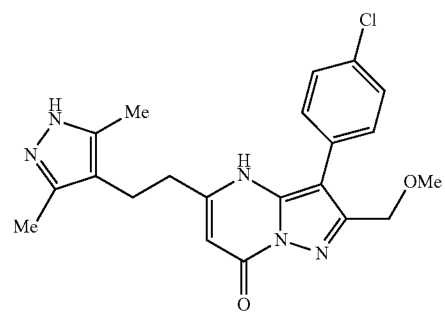 [SMILES: COCc1nn2c(=O)cc(CCc3c(C)n[nH]c3C)[nH]c2c1-c1ccc(Cl)cc1] | |
| IUPAC Name: 5-[2-(3,5-dimethyl-1H-pyrazol-4-yl)ethyl]-2-(methoxymethyl)-3-(4-methylphenyl)-1H-pyrazolo[1,5-a]pyrimidin-7-one | 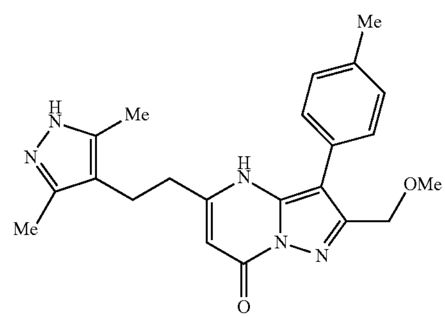 [SMILES: COCc1nn2c(=O)cc(CCc3c(C)n[nH]c3C)[nH]c2c1-c1ccc(C)cc1] | |
| 2-(3,4-dimethoxyphenyl)-5-[2-(3,5-dimethyl-1H-pyrazol-4-yl)ethyl]pyrazolo[5,1-b]pyrimidin-7-ol | | |
| 5-[2-(3,5-dimethyl-1H-pyrazol-4-yl)ethyl]-2-(3-methoxyphenyl)-3-methyl-pyrazolo[5,1-b]pyrimidin-7-ol | 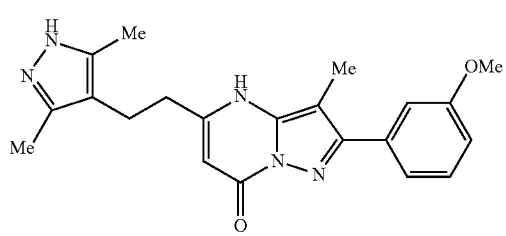 [SMILES: COc1cccc(-c2nn3c(=O)cc(CCc4c(C)n[nH]c4C)[nH]c3c2C)c1] | |

TABLE 1-continued small inhibitory compounds assayed for inhibitory activity against MKK4:

| name | Structure | Inhibition, relative activity of MKK4 compared to control (without additional compound) (%) |
|---|---|---|
| 5-[2-(3,5-dimethyl-1H-pyrazol-4-yl)ethyl]-2-(2-methoxyphenyl)-3-methyl-pyrazolo[5,1-b]pyrimidin-7-ol | 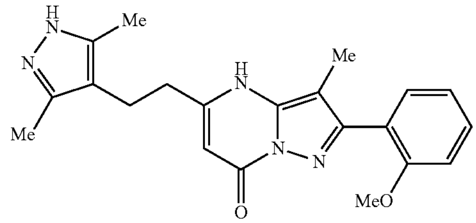 [SMILES: COc1ccccc1-c1nn2c(=O)cc(CCc3c(C)n[nH]c3C)[nH]c2c1C] | |
| 5-[2-(3,5-dimethyl-1H-pyrazol-4-yl)ethyl]-3-methyl-2-(2-thienyl)pyrazolo[5,1-b]pyrimidin-7-ol | 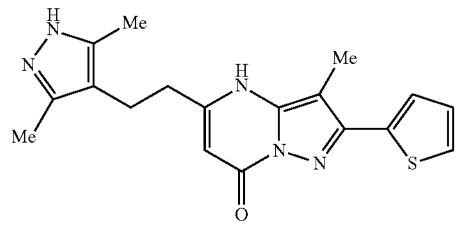 [SMILES: Cc1n[nH]c(C)c1CCc1cc(=O)n2nc(-c3cccs3)c(C)c2[nH]1] | |
| IUPAC Name: 3-(4-chlorophenyl)-5-[2-(3,5-dimethyl-1H-pyrazol-4-yl)-ethyl]-2-methyl-1H-pyrazolo[1,5-a]-pyrimidin-7-one | 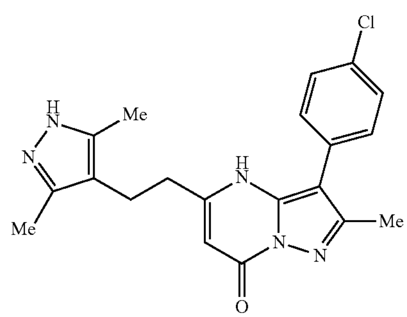 [SMILES: Cc1n[nH]c(C)c1CCc1cc(=O)n2nc(C)c(-c3ccc(Cl)cc3)c2[nH]1] | |
| IUPAC Name: 5-[2-(3,5-dimethyl-1H-pyrazol-4-yl)-ethyl]-2-methyl-3-phenyl-1H-pyrazolo[1,5-a]-pyrimidin-7-one | 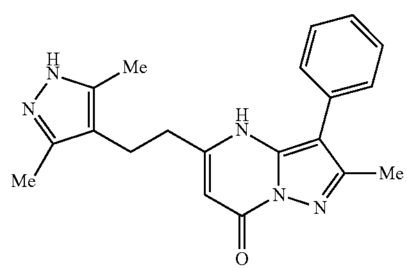 [SMILES: Cc1n[nH]c(C)c1CCc1cc(=O)n2nc(C)c(-c3ccccc3)c2[nH]1] | |
| 5-[2-(3,5-dimethyl-1H-pyrazol-4-yl)ethyl]-2-(4-fluorophenyl)-pyrazolo[5,1-b]pyrimidin-7-o | 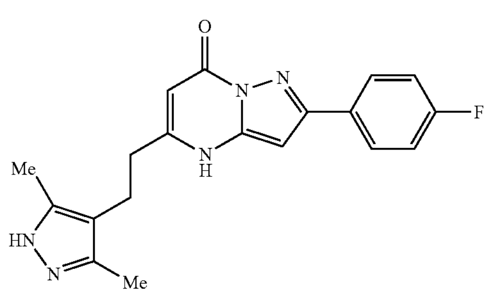 [SMILES: Cc1n[nH]c(C)c1CCc1cc(=O)n2nc(-c3ccc(F)cc3)cc2[nH]1] | |

TABLE 1-continued small inhibitory compounds assayed for inhibitory activity against MKK4:

| name | Structure | Inhibition, relative activity of MKK4 compared to control (without additional compound) (%) |
|---|---|---|
| IUPAC Name: 3-(4-chlorophenyl)-5-[2-(3,5-dimethyl-1H-pyrazol-4-yl)-ethyl]-1H-pyrazolo-[1,5-a]pyrimidin-7-one | 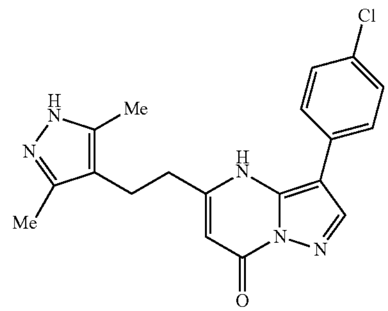 [SMILES: Cc1n[nH]c(C)c1CCc1cc(=O)n2ncc(-c3ccc(Cl)cc3)c2[nH]1] | |

Compounds of Table 1 can be found on http:\\zinc.docking.org.

FIG. 17 gives an overview of the inhibitory effects of these small inhibitory compounds on MKK4 protein in relation to the inhibition by Genistein.

In vitro testing according to Example 4 and in vivo testing according to Example 6 could show that these small inhibitory compounds are suitable for use as a medicament for the treatment of liver failure and/or for the protection of hepatocytes against apoptosis and/or for the regeneration of hepatocytes.

The invention claimed is:

1. A method of treating liver failure in a subject in need thereof, comprising administering to the subject an effective amount of a compound, wherein the compound is an inhibitor of the activity of MKK4, wherein MKK4 is encoded by mRNA with SEQ ID NO: 1204, and wherein the compound is selected from the group consisting of:

| Compound | Structural formula |
|---|---|
| SYN22174524; 5-[2-(3,5-dimethyl-1H-pyrazol-4-yl)ethyl]-7-oxo-N-phenyl-1H-pyrazolo-[1,5-a]-pyrimidine-3-carboxamide | |
| SYN22174787; 5-[2-(3,5-dimethyl-1H-pyrazol-4-yl)ethyl]-3-(4-fluorophenyl)-1H-pyrazolo-[1,5-a]-pyrimidin-7-one | |
| SYN22175977; 5-[2-(3,5-dimethyl-1H-pyrazol-4-yl)ethyl]-3-(4-methylphenyl)-1H-pyrazolo-[1,5-a]-pyrimidin-7-one | |
| SYN22176267; 3-(4-chlorophenyl)-5-[2-(3,5-dimethyl-1H-pyrazol-4-yl)ethyl]-2-(methoxymethyl)-1H-pyrazolo-[1,5-a]-pyrimidin-7-one | |
| SYN22176367; 5-[2-(3,5-dimethyl-1H-pyrazol-4-yl)ethyl]-2-(methoxymethyl)-3-(4-methylphenyl)-1H-pyrazolo-[1,5-a]-pyrimidin-7-one | |
| SYN22176842; 5-[2-(3,5-dimethyl-1H-pyrazol-4-yl)ethyl]-2-(3-methoxyphenyl)-3-methyl-pyrazolo-[5,1-b]-pyrimidin-7-ol | |
| SYN22136990; 5-[2-(3,5-dimethyl-1H-pyrazol-4-yl)ethyl]-2-(2-methoxyphenyl)-3-methyl-pyrazolo-[5,1-b]-pyrimidin-7-ol | |
| SYN22177890; 3-(4-chlorophenyl)-5-[2-(3,5-dimethyl-1H-pyrazol-4-yl)ethyl]-2-methyl-1H-pyrazolo-[1,5-a]-pyrimidin-7-one | |
| IUPAC Name; 5-[2-(3,5-dimethyl-1H-pyrazol-4-yl)ethyl]-7-oxo-N-phenyl-1H-pyrazolo-[1,5-a]-pyrimidin-3-carboxamide | |

| Compound | Structural formula |
|---|---|
| IUPAC Name;<br>5-[2-(3,5-dimethyl-1H-pyrazol-4-yl)ethyl)-3-(4-methylphenyl)-1H-pyrazolo-[1,5-a]-pyrimidin-7-one | |
| IUPAC Name;<br>5-[2-(3,5-dimethyl-1H-pyrazol-4-yl)ethyl)-2-(methoxymethyl)-3-phenyl-1H-pyrazolo-[1,5-a]-pyrimidin-7-one | |
| IUPAC Name;<br>3-(4-chlorophenyl)-5-[2-(3,5-dimethyl-1H-pyrazol-4-yl)ethyl)-2-(methoxymethyl)-1H-pyrazolo-[1,5-a]-pyrimidin-7-one | |
| IUPAC Name;<br>5-[2-(3,5-dimethyl-1H-pyrazol-4-yl)ethyl]-2-(methoxymethyl)-3-(4-methylphenyl)-1H-pyrazolo-[1,5-a]-pyrimidin-7-one | |
| 2-(3,4-dimethoxyphenyl)-5-[2-(3,5-dimethyl-1H-pyrazol-4-yl)ethyl]-pyrazolo-[5,1-b]-pyrimidin-7-ol | |
| 5-[2-(3,5-dimethyl-1H-pyrazol-4-yl)ethyl]-2-(3-methoxyphenyl)-3-methyl-pyrazolo-[5,1-b]-pyrimidin-7-ol | |
| 5-[2-(3,5-dimethyl-1H-pyrazol-4-yl)ethyl]-2-(2-methoxyphenyl)-3-methyl-pyrazolo-[5,1-b]-pyrimidin-7-ol | |
| 5-[2-(3,5-dimethyl-1H-pyrazol-4-yl)ethyl]-3-methyl-2-(2-thionyl)-pyrazolo-[5,1-b]-pyrimidin-7-ol | |
| IUPAC Name;<br>5-[2-(3,5-dimethyl-1H-pyrazol-4-yl)ethyl]-2-methyl-3-phenyl-1H-pyrazolo-[1,5-a]-pyrimidin-7-one | |
| 5-[2-(3,5-dimethyl-1H-pyrazol-4-yl)ethyl]-2-(4-fluorophenyl)-pyrazolo-[5,1-b]-pyrimidin-7-one | | and

| | |
|---|---|
| IUPAC Name;<br>3-(4-chlorophenyl)-5-[2-(3,5-dimethyl-1H-pyrazol-4-yl)ethyl]-1H-pyrazolo-[1,5-a]-pyrimidin-7-one | |

2. A method according to claim 1, wherein the compound comprises a liposome or lipid nanoparticle formulation.

3. A method according to claim 1, wherein the compound is formulation as a composition comprising at least one pharmaceutically acceptable excipient.

* * * * *

```
                          SEQUENCE LISTING

<160> NUMBER OF SEQ ID NOS: 1204

<210> SEQ ID NO 1
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1
uuugugaaca cuauacaccc u                                              21

<210> SEQ ID NO 2
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 2
uuuauuacaa cugaccugca g                                              21
```

```
-continued

<210> SEQ ID NO 3
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 3
uuaaacagca ccauucuccc u                                              21

<210> SEQ ID NO 4
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 4
uugugaacac uauacacccu u                                              21

<210> SEQ ID NO 5
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 5
uagagucuga uguagcagcg a                                              21

<210> SEQ ID NO 6
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 6
uucacuguca uacaaagccu a                                              21
```

```
<210> SEQ ID NO 7
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 7
uaaucuauga uuaauacacu a                                        21

<210> SEQ ID NO 8
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 8
auacauugua auaaacuccu u                                        21

<210> SEQ ID NO 9
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 9
uacauuguaa uaaacuccuu g                                        21

<210> SEQ ID NO 10
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 10
uucuggaaua acaucaucua a                                        21
```

```
<210> SEQ ID NO 11
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 11
acagucaaca acuugaucgu a                                              21

<210> SEQ ID NO 12
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 12
uucaacuuca gugcuuugcg u                                              21

<210> SEQ ID NO 13
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 13
uaucaaucga cauacauggg a                                              21

<210> SEQ ID NO 14
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 14
```
uaauuuaaca ugauauuuca a                                     21

<210> SEQ ID NO 15
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 15
uuugacagua uuuaugacug u                                     21

<210> SEQ ID NO 16
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 16
aauauuucca cuucugucca g                                     21

<210> SEQ ID NO 17
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 17
uacauaaaca cuucgauucc a                                     21

<210> SEQ ID NO 18
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 18
uuauaguuua uaauaaucua u 21

<210> SEQ ID NO 19
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 19
uaguuuauaa uaaucuauga u 21

<210> SEQ ID NO 20
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 20
uuccaguagc ugcaucucca g 21

<210> SEQ ID NO 21
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 21
ugugacuuua aacagcacca u 21

<210> SEQ ID NO 22
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

```
<400> SEQUENCE: 22
uuggauaagg aaaucggccu g                                              21

<210> SEQ ID NO 23
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 23
uagaaaucuu uaucuaauca a                                              21

<210> SEQ ID NO 24
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 24
uagagcaaug ucuccuuuca g                                              21

<210> SEQ ID NO 25
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 25
uauccuuguc gugaugcgcu u                                              21

<210> SEQ ID NO 26
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"
```

```
<400> SEQUENCE: 26
uaaucuauug cacuugguga a                                              21

<210> SEQ ID NO 27
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 27
uuuaucaccu accacaucgg c                                              21

<210> SEQ ID NO 28
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 28
ucaacuguaa cuguaaagca a                                              21

<210> SEQ ID NO 29
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 29
uaaacuuugc cuucuguacu g                                              21

<210> SEQ ID NO 30
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
```

<223> OTHER INFORMATION: /ncRNA_class="siRNA"

<400> SEQUENCE: 30
uugggauuca gaguaaaccu u                                                     21

<210> SEQ ID NO 31
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 31
uacagaucca acagucaccc u                                                     21

<210> SEQ ID NO 32
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 32
uacacuauau acauauuugu a                                                     21

<210> SEQ ID NO 33
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 33
uuuauaguuu auaauaaucu a                                                     21

<210> SEQ ID NO 34
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA

```
<222> LOCATION: 1..21
<223> OTHER INFORMATION: /ncRNA_class="siRNA"

<400> SEQUENCE: 34
uaaagcaaca gaauaucaca u                                              21

<210> SEQ ID NO 35
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 35
ucuuguaaca gugcugaggg u                                              21

<210> SEQ ID NO 36
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 36
uaaacagcac cauucucccu u                                              21

<210> SEQ ID NO 37
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 37
augaguucca uacagaucca a                                              21

<210> SEQ ID NO 38
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
```

```
<221> NAME/KEY: ncRNA
<222> LOCATION: 1..21
<223> OTHER INFORMATION: /ncRNA_class="siRNA"

<400> SEQUENCE: 38
uuauugcaca uggugucugg g                                              21

<210> SEQ ID NO 39
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 39
uugaucaaau acacuauucc a                                              21

<210> SEQ ID NO 40
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 40
uaauauuucc acuucugucc a                                              21

<210> SEQ ID NO 41
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 41
uucuagcagg ugaugaacgu a                                              21

<210> SEQ ID NO 42
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
```

```
<220> FEATURE:
<221> NAME/KEY: ncRNA
<222> LOCATION: 1..21
<223> OTHER INFORMATION: /ncRNA_class="siRNA"

<400> SEQUENCE: 42
uuccucagaa uuacucagcu g                                              21

<210> SEQ ID NO 43
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 43
uuaguugauc aaauacacua u                                              21

<210> SEQ ID NO 44
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 44
agauuuauua caacugaccu g                                              21

<210> SEQ ID NO 45
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 45
uaacaucauc uaauacacua u                                              21

<210> SEQ ID NO 46
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
```

```
                /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 46
uaagauguga ucuaaucaca g                                              21

<210> SEQ ID NO 47
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
                /note="siRNA specific for mRNA encoding MKK4"
                /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 47
uuguugggag ugaagagccg a                                              21

<210> SEQ ID NO 48
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
                /note="siRNA specific for mRNA encoding MKK4"
                /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 48
uauauaucuu aaauagagga g                                              21

<210> SEQ ID NO 49
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
                /note="siRNA specific for mRNA encoding MKK4"
                /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 49
uugcuguaga uuugaaaggu g                                              21

<210> SEQ ID NO 50
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
```

```
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 50
uuucuucugg aauaacauca u                                            21

<210> SEQ ID NO 51
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 51
ucauccacac aauagaacgg u                                            21

<210> SEQ ID NO 52
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 52
uuguaauaaa cuccuugccc u                                            21

<210> SEQ ID NO 53
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 53
uaacaugaua uuucaaacag g                                            21

<210> SEQ ID NO 54
<211> LENGTH: 21
<212> TYPE: RNA
<213> ORGANISM: Artificial Sequence
<220> FEATURE:
<221> NAME/KEY: source
<222> LOCATION: 1..21
```

```
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 54
uuuaucuaau caaucaaggc a                                              21

<210> SEQ ID NO 55
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 55
uagauuuauu acaacugacc u                                              21

<210> SEQ ID NO 56
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 56
uaauacacua uauacauauu u                                              21

<210> SEQ ID NO 57
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 57
uaucacauca guaaucuauu g                                              21

<210> SEQ ID NO 58
<211> LENGTH: 21
<212> TYPE: RNA
<213> ORGANISM: Artificial Sequence
<220> FEATURE:
<221> NAME/KEY: source
```

```
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 58
uuacgucuug cuuccucuca g                                              21

<210> SEQ ID NO 59
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 59
ucaacaacuu gaucguacug a                                              21

<210> SEQ ID NO 60
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 60
aaucuuuauc uaaucaauca a                                              21

<210> SEQ ID NO 61
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 61
uuaacaugau auuucaaaca g                                              21

<210> SEQ ID NO 62
<211> LENGTH: 21
<212> TYPE: RNA
<213> ORGANISM: Artificial Sequence
<220> FEATURE:
```

```
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 62
uaaaguuuag gauaccgugg g                                              21

<210> SEQ ID NO 63
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 63
uuaagcgcaa gucacauagc g                                              21

<210> SEQ ID NO 64
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 64
uuagugcuuu cacaguugcu a                                              21

<210> SEQ ID NO 65
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 65
ucuaaucaca gucaacaacu u                                              21

<210> SEQ ID NO 66
<211> LENGTH: 21
<212> TYPE: RNA
<213> ORGANISM: Artificial Sequence
```

```
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 66
uucagaguaa accuugcugu a                                              21

<210> SEQ ID NO 67
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 67
acaaaguuga ugaaacucgg g                                              21

<210> SEQ ID NO 68
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 68
uuuagugcuu ucacaguugc u                                              21

<210> SEQ ID NO 69
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 69
uccuugguaa ggaacauccc u                                              21

<210> SEQ ID NO 70
<211> LENGTH: 21
<212> TYPE: RNA
```

```
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 70
uguagcagcg auaucaaucg a                                              21

<210> SEQ ID NO 71
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 71
augugaucua aucacaguca a                                              21

<210> SEQ ID NO 72
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 72
uugcacaugg ugucugggcg a                                              21

<210> SEQ ID NO 73
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 73
uagaaaugaa uuuaagaugu g                                              21

<210> SEQ ID NO 74
<211> LENGTH: 21
```

```
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 74
uuggaagguu ugauaucucu g                                              21

<210> SEQ ID NO 75
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 75
uucauucuaa uuuaacauga u                                              21

<210> SEQ ID NO 76
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 76
uugcacuugg ugaagaaagu a                                              21

<210> SEQ ID NO 77
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 77
auaucaaucg acauacaugg g                                              21

<210> SEQ ID NO 78
```

```
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 78
aucaguaauc uauugcacuu g                                              21

<210> SEQ ID NO 79
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 79
ucuuauugca cauggugucu g                                              21

<210> SEQ ID NO 80
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 80
ucaacuucag ugcuuugcgu u                                              21

<210> SEQ ID NO 81
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 81
ucaccuacca caucggcugg g                                              21
```

```
<210> SEQ ID NO 82
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 82
uugacagaac cauaagcucc u                                              21

<210> SEQ ID NO 83
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 83
uuuauuguuu gacaguauuu a                                              21

<210> SEQ ID NO 84
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 84
auaacaucau cuaauacacu a                                              21

<210> SEQ ID NO 85
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 85
uuguuugaca guauuuauga c                                              21
```

```
<210> SEQ ID NO 86
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 86
uugguaagga caucccugc u                                               21

<210> SEQ ID NO 87
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 87
uaaacacuuc gauuccaugu a                                              21

<210> SEQ ID NO 88
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 88
uaguugauca aauacacuau u                                              21

<210> SEQ ID NO 89
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 89
uuuacgucuu gcuuccucuc a                                              21
```

```
<210> SEQ ID NO 90
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 90
uauuacauaa acacuucgau u                                              21

<210> SEQ ID NO 91
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 91
uagaacuauu acauaaacac u                                              21

<210> SEQ ID NO 92
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 92
uaucaccuac cacaucggcu g                                              21

<210> SEQ ID NO 93
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 93
```
ucuccuuuca gaacaguggg a                                              21

<210> SEQ ID NO 94
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 94
ugcuacuagc uacuucuccc u                                              21

<210> SEQ ID NO 95
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 95
uugacaguau uuaugacugu c                                              21

<210> SEQ ID NO 96
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 96
uaaaccuugc uguagauuug a                                              21

<210> SEQ ID NO 97
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 97
uaagcgcaag ucacauagcg a                                              21

<210> SEQ ID NO 98
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 98
aaucacaguc aacaacuuga u                                              21

<210> SEQ ID NO 99
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 99
ucaaauacac uauuccacuu u                                              21

<210> SEQ ID NO 100
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 100
uuucagaagc ucuuuauacu u                                              21

<210> SEQ ID NO 101
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

```
<400> SEQUENCE: 101
aacuauuaca uaaacacuuc g                                              21

<210> SEQ ID NO 102
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 102
auggaaacga acaccaaucu u                                              21

<210> SEQ ID NO 103
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 103
uguaacugua aagcaacaga a                                              21

<210> SEQ ID NO 104
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 104
aacaacugag auuuggucuu u                                              21

<210> SEQ ID NO 105
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"
```

-continued

<400> SEQUENCE: 105
uauuccagug ugcuugaacc a                                              21

<210> SEQ ID NO 106
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 106
augacuguca cucugagagg a                                              21

<210> SEQ ID NO 107
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 107
uauuuaugac ugucacucug a                                              21

<210> SEQ ID NO 108
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 108
uguaauaaac uccuugcccu u                                              21

<210> SEQ ID NO 109
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21

<223> OTHER INFORMATION: /ncRNA_class="siRNA"

<400> SEQUENCE: 109
uuucuauguu cagacauagu a                                              21

<210> SEQ ID NO 110
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 110
uucuuuacgu cuugcuuccu c                                              21

<210> SEQ ID NO 111
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 111
uagauuugaa agguggauuu g                                              21

<210> SEQ ID NO 112
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 112
uugggucuau ucuuucaggu g                                              21

<210> SEQ ID NO 113
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA

```
<222> LOCATION: 1..21
<223> OTHER INFORMATION: /ncRNA_class="siRNA"

<400> SEQUENCE: 113
uuaucaccua ccacaucggc u                                              21

<210> SEQ ID NO 114
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 114
agaacuauua cauaaacacu u                                              21

<210> SEQ ID NO 115
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 115
ucuucuuuca guccuggugg u                                              21

<210> SEQ ID NO 116
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 116
ugacagaacc auaagcuccu c                                              21

<210> SEQ ID NO 117
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
```

```
<221> NAME/KEY: ncRNA
<222> LOCATION: 1..21
<223> OTHER INFORMATION: /ncRNA_class="siRNA"

<400> SEQUENCE: 117
uuuauaauaa ucuaugauua a                                              21

<210> SEQ ID NO 118
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 118
uacgagaggu ucuagcaggu g                                              21

<210> SEQ ID NO 119
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 119
uuuaugacug ucacucugag a                                              21

<210> SEQ ID NO 120
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 120
auucuuuacg ucuugcuucc u                                              21

<210> SEQ ID NO 121
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
```

```
<220> FEATURE:
<221> NAME/KEY: ncRNA
<222> LOCATION: 1..21
<223> OTHER INFORMATION: /ncRNA_class="siRNA"

<400> SEQUENCE: 121
auauauagcu gcuacaaguu g                                                  21

<210> SEQ ID NO 122
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 122
uucuaauuua acaugauauu u                                                  21

<210> SEQ ID NO 123
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 123
aaccauaagc uccucgucca a                                                  21

<210> SEQ ID NO 124
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 124
ucuuaggauc agcaccuucu u                                                  21

<210> SEQ ID NO 125
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
```

```
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 125
uuccaaagcu ccaagaagca g                                              21

<210> SEQ ID NO 126
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 126
uauaucuuaa auagaggagg a                                              21

<210> SEQ ID NO 127
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 127
uuuaagaugu gaucuaauca c                                              21

<210> SEQ ID NO 128
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 128
uagaguccac aagcugucca c                                              21

<210> SEQ ID NO 129
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
```

```
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 129
ucuaaaguuu aggauaccgu g                                              21

<210> SEQ ID NO 130
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 130
uauauagcug cuacaaguug u                                              21

<210> SEQ ID NO 131
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 131
uuucacaguu gcuaaaguga u                                              21

<210> SEQ ID NO 132
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 132
uagaggagga auucaaacaa g                                              21

<210> SEQ ID NO 133
<211> LENGTH: 21
<212> TYPE: RNA
<213> ORGANISM: Artificial Sequence
<220> FEATURE:
<221> NAME/KEY: source
<222> LOCATION: 1..21
```

```
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 133
uuaucuaauc aaucaaggca c                                              21

<210> SEQ ID NO 134
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 134
ucgaaggcag acauagagca a                                              21

<210> SEQ ID NO 135
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 135
uuacaacuga ccugcaggca a                                              21

<210> SEQ ID NO 136
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 136
acacauucug uccugucucu a                                              21

<210> SEQ ID NO 137
<211> LENGTH: 21
<212> TYPE: RNA
<213> ORGANISM: Artificial Sequence
<220> FEATURE:
<221> NAME/KEY: source
```

```
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 137
uugaucguac ugacuuccac a                                              21

<210> SEQ ID NO 138
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 138
auaucuuaaa uagaggagga a                                              21

<210> SEQ ID NO 139
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 139
uucuucugga auaacaucau c                                              21

<210> SEQ ID NO 140
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 140
auaaccagag cucacaaugu a                                              21

<210> SEQ ID NO 141
<211> LENGTH: 21
<212> TYPE: RNA
<213> ORGANISM: Artificial Sequence
<220> FEATURE:
```

```
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 141
uauuccacuu uggauaagga a                                              21

<210> SEQ ID NO 142
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 142
uuaaauagag gaggaauuca a                                              21

<210> SEQ ID NO 143
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 143
auuuaugacu gucacucuga g                                              21

<210> SEQ ID NO 144
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 144
ucuugcuucc ucucagcccu u                                              21

<210> SEQ ID NO 145
<211> LENGTH: 21
<212> TYPE: RNA
<213> ORGANISM: Artificial Sequence
```

-continued

```
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 145
uugacaaagu ugaugaaacu c                                             21

<210> SEQ ID NO 146
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 146
uagcaugcga ccucaacggc a                                             21

<210> SEQ ID NO 147
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 147
uauguuacug agcuccauuu u                                             21

<210> SEQ ID NO 148
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 148
auccuugucg ugaugcgcuu g                                             21

<210> SEQ ID NO 149
<211> LENGTH: 21
<212> TYPE: RNA
```

```
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 149
uuauuguuug acaguauuua u                                              21

<210> SEQ ID NO 150
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 150
uaucccugca cauuagcuuu u                                              21

<210> SEQ ID NO 151
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 151
uauuguuuga caguauuuau g                                              21

<210> SEQ ID NO 152
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 152
ucagcugcgg aggaucuccu u                                              21

<210> SEQ ID NO 153
<211> LENGTH: 21
```

-continued

```
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 153
uacuccgcau uacuacaucc a                                              21

<210> SEQ ID NO 154
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 154
cugaccagca cuaacacugu g                                              21

<210> SEQ ID NO 155
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 155
uaagugaaga agcacaagau a                                              21

<210> SEQ ID NO 156
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 156
uucagaagcu cuuuauacuu u                                              21

<210> SEQ ID NO 157
```

```
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 157
ugaauuuaag augugaucua a                                              21

<210> SEQ ID NO 158
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 158
ucacauagcg acaauagacc a                                              21

<210> SEQ ID NO 159
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 159
uccuuugucu cccagcucca g                                              21

<210> SEQ ID NO 160
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 160
aauuucucca aggucuuuca a                                              21
```

```
<210> SEQ ID NO 161
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 161
auagaguccc caagcugucc a                                      21

<210> SEQ ID NO 162
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 162
uccuagauuu auuacaacug a                                      21

<210> SEQ ID NO 163
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 163
ucgacauaca ugggagagcu g                                      21

<210> SEQ ID NO 164
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 164
ucaaucaggu auuacaagga u                                      21
```

<210> SEQ ID NO 165
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 165
cuaaucacag ucaacaacuu g                                             21

<210> SEQ ID NO 166
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 166
aucaaauaca cuauuccacu u                                             21

<210> SEQ ID NO 167
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 167
auucggaaac ugaagaccug g                                             21

<210> SEQ ID NO 168
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 168
auguucaccu cuuugaacgc a                                             21

<210> SEQ ID NO 169
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 169
uacuagcuac uucucccugu u                                              21

<210> SEQ ID NO 170
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 170
aacaccaauc uuauugcaca u                                              21

<210> SEQ ID NO 171
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 171
ucggauccuc aucuggucca a                                              21

<210> SEQ ID NO 172
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 172
auacacuaua uacauauuug u                                21

<210> SEQ ID NO 173
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 173
aaacuccaga caucagagcg g                                21

<210> SEQ ID NO 174
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 174
aaacaacuga gauuuggucu u                                21

<210> SEQ ID NO 175
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 175
uugcguuuac ccugcaugcu g                                21

<210> SEQ ID NO 176
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 176

```
uaaucacagu caacaacuug a                                              21

<210> SEQ ID NO 177
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 177
acuauuacau aaacacuucg a                                              21

<210> SEQ ID NO 178
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 178
ugucauacaa agccuaaggu u                                              21

<210> SEQ ID NO 179
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 179
uauguucaga cauaguacau u                                              21

<210> SEQ ID NO 180
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"
```

```
<400> SEQUENCE: 180
acaacuugau cguacugacu u                                              21

<210> SEQ ID NO 181
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 181
uuaggaucag caccuucuuu g                                              21

<210> SEQ ID NO 182
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 182
ugaucguacu gacuuccaca u                                              21

<210> SEQ ID NO 183
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 183
auuguuggga gugaagagcc g                                              21

<210> SEQ ID NO 184
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"
```

<400> SEQUENCE: 184
uauagcugcu acaaguuguu c							21

<210> SEQ ID NO 185
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 185
uuugaacgca acaugguuuu u							21

<210> SEQ ID NO 186
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 186
uccaguagaa uuccaaugcc a							21

<210> SEQ ID NO 187
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 187
aagcugucca cugaugccga a							21

<210> SEQ ID NO 188
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21

<223> OTHER INFORMATION: /ncRNA_class="siRNA"

<400> SEQUENCE: 188
uagugcuuuc acaguugcua a                                                     21

<210> SEQ ID NO 189
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 189
uuaucaaacg agguagacau g                                                     21

<210> SEQ ID NO 190
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 190
ugguaaggaa caucccugcu a                                                     21

<210> SEQ ID NO 191
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 191
uuugauaucu cugugaauaa u                                                     21

<210> SEQ ID NO 192
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA -continued
<222> LOCATION: 1..21
<223> OTHER INFORMATION: /ncRNA_class="siRNA"

<400> SEQUENCE: 192
uagcugcuac aaguuguucc a                                              21

<210> SEQ ID NO 193
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 193
aaacuuugcc uucuguacug u                                              21

<210> SEQ ID NO 194
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 194
ugaucuaauc acagucaaca a                                              21

<210> SEQ ID NO 195
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 195
aucuguaaac uuugccuucu g                                              21

<210> SEQ ID NO 196
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:

```
<221> NAME/KEY: ncRNA
<222> LOCATION: 1..21
<223> OTHER INFORMATION: /ncRNA_class="siRNA"

<400> SEQUENCE: 196
acauaguaca uucaucacug u                                              21

<210> SEQ ID NO 197
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 197
uuuggauaag gaaaucggcc u                                              21

<210> SEQ ID NO 198
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 198
uucggauccu caucuggucc a                                              21

<210> SEQ ID NO 199
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 199
uacaaacaua gcaugcgacc u                                              21

<210> SEQ ID NO 200
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
```

```
<220> FEATURE:
<221> NAME/KEY: ncRNA
<222> LOCATION: 1..21
<223> OTHER INFORMATION: /ncRNA_class="siRNA"

<400> SEQUENCE: 200
augaauuuaa gaugugaucu a                                              21

<210> SEQ ID NO 201
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 201
auuacaacug accugcaggc a                                              21

<210> SEQ ID NO 202
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 202
ucucugacca gcacuaacac u                                              21

<210> SEQ ID NO 203
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 203
auucaaacaa gaauacagga u                                              21

<210> SEQ ID NO 204
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
```

```
            /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 204
agcaacagaa uaucacauca g                                              21

<210> SEQ ID NO 205
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 205
aauuccuccu uugucuccca g                                              21

<210> SEQ ID NO 206
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 206
aucaccuacc acaucggcug g                                              21

<210> SEQ ID NO 207
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 207
ucuguccaga agaauauugg a                                              21

<210> SEQ ID NO 208
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
```

```
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 208
aaaguugaug aaacucgggg a                                             21

<210> SEQ ID NO 209
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 209
auacacuauu ccacuuugga u                                             21

<210> SEQ ID NO 210
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 210
uaugacuguc acucugagag g                                             21

<210> SEQ ID NO 211
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 211
aauucugcaa uuuacaggga u                                             21

<210> SEQ ID NO 212
<211> LENGTH: 21
<212> TYPE: RNA
<213> ORGANISM: Artificial Sequence
<220> FEATURE:
<221> NAME/KEY: source
<222> LOCATION: 1..21
```

```
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 212
auuacaagga ugcacguucu a                                              21

<210> SEQ ID NO 213
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 213
uuaugugguc auccacacaa u                                              21

<210> SEQ ID NO 214
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 214
ucacucugag aggagacaca g                                              21

<210> SEQ ID NO 215
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 215
ucuuugaacg caacaugguu u                                              21

<210> SEQ ID NO 216
<211> LENGTH: 21
<212> TYPE: RNA
<213> ORGANISM: Artificial Sequence
<220> FEATURE:
<221> NAME/KEY: source
```

```
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 216
uccaauuucu ccaaggucuu u                                             21

<210> SEQ ID NO 217
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 217
uaacuguaaa gcaacagaau a                                             21

<210> SEQ ID NO 218
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 218
aaaguuuagg auaccguggg g                                             21

<210> SEQ ID NO 219
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 219
uucagaacag ugggaagucu a                                             21

<210> SEQ ID NO 220
<211> LENGTH: 21
<212> TYPE: RNA
<213> ORGANISM: Artificial Sequence
<220> FEATURE:
```

```
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 220
ugcugcuuca cugucauaca a                                              21

<210> SEQ ID NO 221
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 221
uccucugcag ugaaauccca g                                              21

<210> SEQ ID NO 222
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 222
uuaugacugu cacucugaga g                                              21

<210> SEQ ID NO 223
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 223
aauaucacau caguaaucua u                                              21

<210> SEQ ID NO 224
<211> LENGTH: 21
<212> TYPE: RNA
<213> ORGANISM: Artificial Sequence
```

```
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 224
aucaccugca ucucaggcca u                                               21

<210> SEQ ID NO 225
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 225
ugugcuugaa ccacucacag u                                               21

<210> SEQ ID NO 226
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 226
aauaacauca ucuaauacac u                                               21

<210> SEQ ID NO 227
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 227
auugcuacua gcuacuucuc c                                               21

<210> SEQ ID NO 228
<211> LENGTH: 21
<212> TYPE: RNA
```

```
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 228
uucggaaacu gaagaccugg a                                              21

<210> SEQ ID NO 229
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 229
auuuauuaca acugaccugc a                                              21

<210> SEQ ID NO 230
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 230
uugacagcag agaaacagau u                                              21

<210> SEQ ID NO 231
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 231
ugaucaaaua cacuauucca c                                              21

<210> SEQ ID NO 232
<211> LENGTH: 21
```

```
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 232
uauaguuuau aauaaucuau g                                              21

<210> SEQ ID NO 233
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 233
ugguuuagug cuuucacagu u                                              21

<210> SEQ ID NO 234
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 234
uucaugaaua uguucaucac a                                              21

<210> SEQ ID NO 235
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 235
ucacaguuug ugaacacuau a                                              21

<210> SEQ ID NO 236
```

```
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 236
aauucaaaca agaauacagg a                                              21

<210> SEQ ID NO 237
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 237
uacaguucuu acacuauuuu c                                              21

<210> SEQ ID NO 238
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 238
agcugcuaca aguuguucca g                                              21

<210> SEQ ID NO 239
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 239
ucagaguaaa ccuugcugua g                                              21
```

```
<210> SEQ ID NO 240
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 240
uuucaagucc ucugcaguga a                                              21

<210> SEQ ID NO 241
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 241
uagcgacaau agaccacagg g                                              21

<210> SEQ ID NO 242
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 242
aacuccagac aucagagcgg a                                              21

<210> SEQ ID NO 243
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 243
auagcgacaa uagaccacag g                                              21
```

```
<210> SEQ ID NO 244
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 244
uaucaaacga gguagacaug a                                              21

<210> SEQ ID NO 245
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 245
ugaauucugc aauuuacagg g                                              21

<210> SEQ ID NO 246
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 246
uaggugacag gaguauacag a                                              21

<210> SEQ ID NO 247
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 247
ucugaccagc acuaacacug u                                              21
```

-continued

```
<210> SEQ ID NO 248
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 248
aguuauguua cugagcucca u                                              21

<210> SEQ ID NO 249
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 249
uaaggcaaua ucccugcaca u                                              21

<210> SEQ ID NO 250
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 250
uuacaaggau gcacguucua g                                              21

<210> SEQ ID NO 251
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 251
```
uguucucagu cucucuaugu g                                              21

<210> SEQ ID NO 252
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 252
aacacauucu guccugucuc u                                              21

<210> SEQ ID NO 253
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 253
uucauccuuc guaaggcaca a                                              21

<210> SEQ ID NO 254
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 254
aaguugacag cagagaaaca g                                              21

<210> SEQ ID NO 255
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 255
ucuguaaacu uugccuucug u                                          21

<210> SEQ ID NO 256
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 256
uuaagaugug aucuaaucac a                                          21

<210> SEQ ID NO 257
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 257
augaacguaa aggcugccgu u                                          21

<210> SEQ ID NO 258
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 258
uuagcuccug gacagucaga a                                          21

<210> SEQ ID NO 259
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

```
<400> SEQUENCE: 259
auucagagua aaccuugcug u                                              21

<210> SEQ ID NO 260
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 260
ugaaauccca guguuguuca g                                              21

<210> SEQ ID NO 261
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 261
uauuacaacu gaccugcagg c                                              21

<210> SEQ ID NO 262
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 262
uugcuacuag cuacuucucc c                                              21

<210> SEQ ID NO 263
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"
```

```
<400> SEQUENCE: 263
uuugcguuua cccugcaugc u                                              21

<210> SEQ ID NO 264
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 264
auguauauau cuuaaauaga g                                              21

<210> SEQ ID NO 265
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 265
aaauacacua uuccacuuug g                                              21

<210> SEQ ID NO 266
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 266
aaacacuucg auuccaugua u                                              21

<210> SEQ ID NO 267
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
```

<223> OTHER INFORMATION: /ncRNA_class="siRNA"

<400> SEQUENCE: 267
acauagagca augucuccuu u                                           21

<210> SEQ ID NO 268
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 268
ugggcaauca cuacuccgca u                                           21

<210> SEQ ID NO 269
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 269
aucuaauaca cuauauacau a                                           21

<210> SEQ ID NO 270
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 270
uucuguccug ucucuauauu u                                           21

<210> SEQ ID NO 271
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA

```
<222> LOCATION: 1..21
<223> OTHER INFORMATION: /ncRNA_class="siRNA"

<400> SEQUENCE: 271
ugaagaagca caagauacuu a                                              21

<210> SEQ ID NO 272
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 272
uggaagguuu gauaucucug u                                              21

<210> SEQ ID NO 273
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 273
uuccacuucu guccagaaga a                                              21

<210> SEQ ID NO 274
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 274
auauagcugc uacaaguugu u                                              21

<210> SEQ ID NO 275
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
```

```
<221> NAME/KEY: ncRNA
<222> LOCATION: 1..21
<223> OTHER INFORMATION: /ncRNA_class="siRNA"

<400> SEQUENCE: 275
aacaacuuga ucguacugac u                                              21

<210> SEQ ID NO 276
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 276
ucacagucaa caacuugauc g                                              21

<210> SEQ ID NO 277
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 277
guauuuauga cugucacucu g                                              21

<210> SEQ ID NO 278
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 278
ucuaauacac uauauacaua u                                              21

<210> SEQ ID NO 279
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
```

```
<220> FEATURE:
<221> NAME/KEY: ncRNA
<222> LOCATION: 1..21
<223> OTHER INFORMATION: /ncRNA_class="siRNA"

<400> SEQUENCE: 279
ucgauuccau guauauaucu u                                              21

<210> SEQ ID NO 280
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 280
ugggagugaa gagccgagcg g                                              21

<210> SEQ ID NO 281
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 281
uuauuacaac ugaccugcag g                                              21

<210> SEQ ID NO 282
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 282
uuccaggauu uggaagucug a                                              21

<210> SEQ ID NO 283
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
```

```
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 283
auccucaucu gguccaaugu g                                              21

<210> SEQ ID NO 284
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 284
uuccauacag auccaacagu c                                              21

<210> SEQ ID NO 285
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 285 uuucagoccu ggugguuugu g                                              21

<210> SEQ ID NO 286
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 286
auaguuuaua auaaucuaug a                                              21

<210> SEQ ID NO 287
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
```

```
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 287
uuacauaaac acuucgauuc c                                              21

<210> SEQ ID NO 288
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 288
acaagcuguc cacugaugcc g                                              21

<210> SEQ ID NO 289
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 289
aaacauagca ugcgaccuca a                                              21

<210> SEQ ID NO 290
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 290
uagacaugag uuccauacag a                                              21

<210> SEQ ID NO 291
<211> LENGTH: 21
<212> TYPE: RNA
<213> ORGANISM: Artificial Sequence
<220> FEATURE:
<221> NAME/KEY: source
<222> LOCATION: 1..21
```

```
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 291
aacaucaucu aauacacuau a                                              21

<210> SEQ ID NO 292
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 292
uauuucaaac aggaaauuug g                                              21

<210> SEQ ID NO 293
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 293
uggacaguca gaauugcuuu u                                              21

<210> SEQ ID NO 294
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 294
aacucauaca augugauccc c                                              21

<210> SEQ ID NO 295
<211> LENGTH: 21
<212> TYPE: RNA
<213> ORGANISM: Artificial Sequence
<220> FEATURE:
<221> NAME/KEY: source
```

```
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 295
uaugugguca uccacacaau a                                              21

<210> SEQ ID NO 296
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 296
aauaucccug cacauuagcu u                                              21

<210> SEQ ID NO 297
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 297
ucacaucagu aaucuauugc a                                              21

<210> SEQ ID NO 298
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 298
ucuuucaagu ccucugcagu g                                              21

<210> SEQ ID NO 299
<211> LENGTH: 21
<212> TYPE: RNA
<213> ORGANISM: Artificial Sequence
<220> FEATURE:
```

```
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 299
aacaguggga agucuaaagu u                                              21

<210> SEQ ID NO 300
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 300
ugacugucac ucugagagga g                                              21

<210> SEQ ID NO 301
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 301
ucacagagcu uaauauuucc a                                              21

<210> SEQ ID NO 302
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 302
ugaaccacuc acagugcugc u                                              21

<210> SEQ ID NO 303
<211> LENGTH: 21
<212> TYPE: RNA
<213> ORGANISM: Artificial Sequence
```

```
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 303
ucugagagga gacacagcaa u                                                 21

<210> SEQ ID NO 304
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 304
acgaacacca aucuuauugc a                                                 21

<210> SEQ ID NO 305
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 305
uacuacaucc aaauccauaa g                                                 21

<210> SEQ ID NO 306
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 306
uagaacgguc agauuagcuc c                                                 21

<210> SEQ ID NO 307
<211> LENGTH: 21
<212> TYPE: RNA
```

-continued

```
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 307
aagcaaacaa cugagauuug g                                              21

<210> SEQ ID NO 308
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 308
uccacuguug accgaauucu u                                              21

<210> SEQ ID NO 309
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 309
uugaaccacu cacagugcug c                                              21

<210> SEQ ID NO 310
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 310
uccuucguaa ggcacaaguu g                                              21

<210> SEQ ID NO 311
<211> LENGTH: 21
```

```
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 311
uacacuauuc cacuuuggau a                                              21

<210> SEQ ID NO 312
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 312
acaaauaagg caauaucccu g                                              21

<210> SEQ ID NO 313
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 313
auucauucua auuuaacaug a                                              21

<210> SEQ ID NO 314
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 314
aaucaaggca cauugcuacu a                                              21

<210> SEQ ID NO 315
```

```
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 315
uccaaggucu uucaaguccu c                                              21

<210> SEQ ID NO 316
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 316
gucaacaacu ugaucguacu g                                              21

<210> SEQ ID NO 317
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 317
aaauucauuc uaauuuaaca u                                              21

<210> SEQ ID NO 318
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 318
uauuugccca cuugguuugu g                                              21
```

```
<210> SEQ ID NO 319
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 319
uccaacaguc acccucucug a                                        21

<210> SEQ ID NO 320
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 320
ugccucuuua ucaccuacca c                                        21

<210> SEQ ID NO 321
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 321
uucgauucca uguauauauc u                                        21

<210> SEQ ID NO 322
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 322
cauaguacau ucaucacugu g                                        21
```

```
<210> SEQ ID NO 323
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 323
ucucccuuua uuguuugaca g                                              21

<210> SEQ ID NO 324
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 324
caaacaucaa cuguaacugu a                                              21

<210> SEQ ID NO 325
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 325
aaguuuagga uaccgugggg g                                              21

<210> SEQ ID NO 326
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 326
aacuuugccu ucuguacugu u                                              21
```

```
<210> SEQ ID NO 327
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 327
uuucaugaau auguucauca c                                              21

<210> SEQ ID NO 328
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 328
aagguuugau aucucuguga a                                              21

<210> SEQ ID NO 329
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 329
uuauuugccc acuugguuug u                                              21

<210> SEQ ID NO 330
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 330
```
uaauaaucua ugauuaauac a                                              21

<210> SEQ ID NO 331
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 331
uccaguagcu gcaucuccag g                                              21

<210> SEQ ID NO 332
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 332
uugcccuuaa guuuauaguu u                                              21

<210> SEQ ID NO 333
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 333
auuccagugu gcuugaacca c                                              21

<210> SEQ ID NO 334
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 334
uacagacaug auggaaacga a                                    21

<210> SEQ ID NO 335
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 335
auuguaauaa acuccuugcc c                                    21

<210> SEQ ID NO 336
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 336
uaaguuuaua guuuauaaua a                                    21

<210> SEQ ID NO 337
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 337
aauauauagc ugcuacaagu u                                    21

<210> SEQ ID NO 338
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

```
<400> SEQUENCE: 338
ugacaggagu auacagacau g                                              21

<210> SEQ ID NO 339
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 339
uccacacaau agaacgguca g                                              21

<210> SEQ ID NO 340
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 340
aucaaucaag gcacauugcu a                                              21

<210> SEQ ID NO 341
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 341
auagaggagg aauucaaaca a                                              21

<210> SEQ ID NO 342
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"
```

```
<400> SEQUENCE: 342
uuauguuacu gagcuccauu u                                                21

<210> SEQ ID NO 343
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 343
cauuacuaca uccaaaucca u                                                21

<210> SEQ ID NO 344
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 344
ucaccucuuu gaacgcaaca u                                                21

<210> SEQ ID NO 345
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 345
aacaugauau uucaaacagg a                                                21

<210> SEQ ID NO 346
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
```

<223> OTHER INFORMATION: /ncRNA_class="siRNA"

<400> SEQUENCE: 346
aucuuuaucu aaucaaucaa g                    21

<210> SEQ ID NO 347
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 347
auccuagauu uauuacaacu g                    21

<210> SEQ ID NO 348
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 348
uaaauuccuc cuuugucucc c                    21

<210> SEQ ID NO 349
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 349
acuguaacug uaaagcaaca g                    21

<210> SEQ ID NO 350
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA

```
<222> LOCATION: 1..21
<223> OTHER INFORMATION: /ncRNA_class="siRNA"

<400> SEQUENCE: 350
uguugacaga accauaagcu c                                              21

<210> SEQ ID NO 351
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 351
ucaguaaucu auugcacuug g                                              21

<210> SEQ ID NO 352
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 352
uccuguagga uugggauuca g                                              21

<210> SEQ ID NO 353
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 353
uagaucaaag agauaaucac u                                              21

<210> SEQ ID NO 354
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
```

```
<221> NAME/KEY: ncRNA
<222> LOCATION: 1..21
<223> OTHER INFORMATION: /ncRNA_class="siRNA"

<400> SEQUENCE: 354
ugggagagcu gggaguagcu g                                              21

<210> SEQ ID NO 355
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 355
uggucgaagg cagacauaga g                                              21

<210> SEQ ID NO 356
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 356
ugcacguucu aggugacagg a                                              21

<210> SEQ ID NO 357
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 357
agacauagag caaugucucc u                                              21

<210> SEQ ID NO 358
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
```

```
<220> FEATURE:
<221> NAME/KEY: ncRNA
<222> LOCATION: 1..21
<223> OTHER INFORMATION: /ncRNA_class="siRNA"

<400> SEQUENCE: 358
aaucuuauug cacauggugu c                                              21

<210> SEQ ID NO 359
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
     /note="siRNA specific for mRNA encoding MKK4"
     /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 359
aucaacugua acuguaaagc a                                              21

<210> SEQ ID NO 360
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
     /note="siRNA specific for mRNA encoding MKK4"
     /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 360
uagcugcauc uccagguuuu g                                              21

<210> SEQ ID NO 361
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
     /note="siRNA specific for mRNA encoding MKK4"
     /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 361
aacagcacca uucucccuuu a                                              21

<210> SEQ ID NO 362
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
     /note="siRNA specific for mRNA encoding MKK4"
```

```
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 362
uaggauuggg auucagagua a                                              21

<210> SEQ ID NO 363
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 363
aaucuaugau uaauacacua a                                              21

<210> SEQ ID NO 364
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 364
uggaaacgaa caccaaucuu a                                              21

<210> SEQ ID NO 365
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 365
ucacagugcu gcuucacugu c                                              21

<210> SEQ ID NO 366
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
```

```
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 366
aguaaucuau ugcacuuggu g                                              21

<210> SEQ ID NO 367
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 367
uaucuaauca aucaaggcac a                                              21

<210> SEQ ID NO 368
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 368
uuucagaaca gugggaaguc u                                              21

<210> SEQ ID NO 369
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 369
ucagaagcuc uuuauacuuu g                                              21

<210> SEQ ID NO 370
<211> LENGTH: 21
<212> TYPE: RNA
<213> ORGANISM: Artificial Sequence
<220> FEATURE:
<221> NAME/KEY: source
<222> LOCATION: 1..21
```

```
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 370
uaggaucagc accuucuuug a                                              21

<210> SEQ ID NO 371
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 371
uauuggaagg uuugauaucu c                                              21

<210> SEQ ID NO 372
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 372
uauugcacau ggugucuggg c                                              21

<210> SEQ ID NO 373
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 373
aucuaaucaa ucaaggcaca u                                              21

<210> SEQ ID NO 374
<211> LENGTH: 21
<212> TYPE: RNA
<213> ORGANISM: Artificial Sequence
<220> FEATURE:
<221> NAME/KEY: source
```

```
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 374
ugggauucag aguaaaccuu g                                              21

<210> SEQ ID NO 375
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 375
aucagcaccu ucuuugacaa g                                              21

<210> SEQ ID NO 376
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 376
aagccuaagg uucagugcca g                                              21

<210> SEQ ID NO 377
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 377
uccugaugac ucaaugcugu g                                              21

<210> SEQ ID NO 378
<211> LENGTH: 21
<212> TYPE: RNA
<213> ORGANISM: Artificial Sequence
<220> FEATURE:
```

```
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 378
uaauggguaa gugaagaagc a                                              21

<210> SEQ ID NO 379
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 379
uucacaguug cuaaagugau u                                              21

<210> SEQ ID NO 380
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 380
uaucaggcuu gggaccaagg g                                              21

<210> SEQ ID NO 381
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 381
aaacaucaac uguaacugua a                                              21

<210> SEQ ID NO 382
<211> LENGTH: 21
<212> TYPE: RNA
<213> ORGANISM: Artificial Sequence
```

-continued

```
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 382
aucaaagaga uaaucacuuu u                                           21

<210> SEQ ID NO 383
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 383
uauuggauua agcgcaaguc a                                           21

<210> SEQ ID NO 384
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 384
aaggcacauu gcuacuagcu a                                           21

<210> SEQ ID NO 385
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 385
auuugaaagg uggauuugca a                                           21

<210> SEQ ID NO 386
<211> LENGTH: 21
<212> TYPE: RNA
```

```
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 386
uugucgugau gcgcuugggu c                                              21

<210> SEQ ID NO 387
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 387
uguaaagcaa cagaauauca c                                              21

<210> SEQ ID NO 388
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 388
ucauucuaau uuaacaugau a                                              21

<210> SEQ ID NO 389
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 389
ucagguauua caaggaugca c                                              21

<210> SEQ ID NO 390
<211> LENGTH: 21
```

```
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 390
uagcagguga ugaacguaaa g                                              21

<210> SEQ ID NO 391
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 391
aaacacuagc gaauaugaga g                                              21

<210> SEQ ID NO 392
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 392
aaucaaucaa ggcacauugc u                                              21

<210> SEQ ID NO 393
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 393
ucuuaugugg ucauccacac a                                              21

<210> SEQ ID NO 394
```

```
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 394
ugaagaaagu aaauuccucc u                                              21

<210> SEQ ID NO 395
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 395
uucuauguuc agacauagua c                                              21

<210> SEQ ID NO 396
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 396
ugaggucucu cugaccagca c                                              21

<210> SEQ ID NO 397
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 397
ucuauugcac uuggugaaga a                                              21
```

```
<210> SEQ ID NO 398
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 398
auucuuagga ucagcaccuu c                                              21

<210> SEQ ID NO 399
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 399
uguaacagug cugaggguuu u                                              21

<210> SEQ ID NO 400
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 400
aucaaucgac auacauggga g                                              21

<210> SEQ ID NO 401
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 401
cuauuacaua aacacuucga u                                              21
```

```
<210> SEQ ID NO 402
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 402
ucacugucau acaaagccua a                                              21

<210> SEQ ID NO 403
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 403
uuauaauaau cuaugauuaa u                                              21

<210> SEQ ID NO 404
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 404
ugugaacacu auacacccuu u                                              21

<210> SEQ ID NO 405
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 405
uuuccucaga auuacucagc u                                              21
```

<210> SEQ ID NO 406
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 406
ugauguagca gcgauaucaa u                                              21

<210> SEQ ID NO 407
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 407
augcgcuugg gucuauucuu u                                              21

<210> SEQ ID NO 408
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 408
auaaacacuu cgauuccaug u                                              21

<210> SEQ ID NO 409
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 409
ugaacuccug uaggauuggg a                                              21

<210> SEQ ID NO 410
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 410
uguacaguuc uuacacuauu u                                              21

<210> SEQ ID NO 411
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 411
aaaccuugcu guagauuuga a                                              21

<210> SEQ ID NO 412
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 412
uuaauauuuc cacuucuguc c                                              21

<210> SEQ ID NO 413
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 413
aacaucaacu guaacuguaa a                                                21

<210> SEQ ID NO 414
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 414
aguagcugca ucuccagguu u                                                21

<210> SEQ ID NO 415
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 415
auuccaguag cugcaucucc a                                                21

<210> SEQ ID NO 416
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 416
auauccuugu cgugaugcgc u                                                21

<210> SEQ ID NO 417
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

```
<400> SEQUENCE: 417 aaucauucu aauuuaacau g                                              21

<210> SEQ ID NO 418
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 418
uucuccaagg ucuuucaagu c                                             21

<210> SEQ ID NO 419
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 419
uaaacacuag cgaauaugag a                                             21

<210> SEQ ID NO 420
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 420
uagcgaauau gagagauuug g                                             21

<210> SEQ ID NO 421
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"
```

<400> SEQUENCE: 421
uggauuaagc gcaagucaca u                                              21

<210> SEQ ID NO 422
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 422
ucacccucuc ugaagagugc a                                              21

<210> SEQ ID NO 423
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 423
uccacauuuc augaauaugu u                                              21

<210> SEQ ID NO 424
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 424
aauacacuau uccacuuugg a                                              21

<210> SEQ ID NO 425
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21

-continued

```
<223> OTHER INFORMATION: /ncRNA_class="siRNA"

<400> SEQUENCE: 425
acaccauucc aguagcugca u                                              21

<210> SEQ ID NO 426
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 426
uucuuaugug gucauccaca c                                              21

<210> SEQ ID NO 427
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 427
ugaucaauca gguauuacaa g                                              21

<210> SEQ ID NO 428
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 428
ucguccaauu ucuccaaggu c                                              21

<210> SEQ ID NO 429
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
```

<222> LOCATION: 1..21
<223> OTHER INFORMATION: /ncRNA_class="siRNA"

<400> SEQUENCE: 429
ucccuuuauu guuugacagu a                                              21

<210> SEQ ID NO 430
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 430
ucagaauuac ucagcugcgg a                                              21

<210> SEQ ID NO 431
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 431
ugaggcaagu agaucaaaga g                                              21

<210> SEQ ID NO 432
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 432
uuuaaacagc accauucucc c                                              21

<210> SEQ ID NO 433
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:

```
<221> NAME/KEY: ncRNA
<222> LOCATION: 1..21
<223> OTHER INFORMATION: /ncRNA_class="siRNA"

<400> SEQUENCE: 433
auaucccugc acauuagcuu u                                              21

<210> SEQ ID NO 434
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 434
ucaaucgaca uacaugggag a                                              21

<210> SEQ ID NO 435
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 435
uggugaagaa aguaaauucc u                                              21

<210> SEQ ID NO 436
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 436
augauggaaa cgaacaccaa u                                              21

<210> SEQ ID NO 437
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
```

```
<220> FEATURE:
<221> NAME/KEY: ncRNA
<222> LOCATION: 1..21
<223> OTHER INFORMATION: /ncRNA_class="siRNA"

<400> SEQUENCE: 437
auagcaugcg accucaacgg c                                              21

<210> SEQ ID NO 438
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 438
augggcaauc acuacuccgc a                                              21

<210> SEQ ID NO 439
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 439
uucuguccag aagaauauug g                                              21

<210> SEQ ID NO 440
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 440
aucacaguca acaacuugau c                                              21

<210> SEQ ID NO 441
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
```

```
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 441
uacuagaaau cuuuaucuaa u                                              21

<210> SEQ ID NO 442
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 442
aaucccagug uuguucaggg g                                              21

<210> SEQ ID NO 443
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 443
aagaauauug gaagguuuga u                                              21

<210> SEQ ID NO 444
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 444
ucaaacaaga auacaggaua a                                              21

<210> SEQ ID NO 445
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
```

```
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 445
aagaaaguaa auccuccuu u                                                     21

<210> SEQ ID NO 446
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 446
uccucgucca auuucuccaa g                                                    21

<210> SEQ ID NO 447
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 447
uuugccuucu guacuguuuu c                                                    21

<210> SEQ ID NO 448
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 448
ugcuuugcgu uuacccugca u                                                    21

<210> SEQ ID NO 449
<211> LENGTH: 21
<212> TYPE: RNA
<213> ORGANISM: Artificial Sequence
<220> FEATURE:
<221> NAME/KEY: source
<222> LOCATION: 1..21
```

```
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 449
aacagauucc ucuugagucc c                                              21

<210> SEQ ID NO 450
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 450
auccuuggua aggaacaucc c                                              21

<210> SEQ ID NO 451
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 451
uuugucuccc agcuccagaa g                                              21

<210> SEQ ID NO 452
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 452
uacaugggag agcugggagu a                                              21

<210> SEQ ID NO 453
<211> LENGTH: 21
<212> TYPE: RNA
<213> ORGANISM: Artificial Sequence
<220> FEATURE:
<221> NAME/KEY: source
```

```
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 453
ugugcaagcu cuucucacuc a                                              21

<210> SEQ ID NO 454
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 454
uacaacugac cugcaggcaa a                                              21

<210> SEQ ID NO 455
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 455
auguacaguu cuuacacuau u                                              21

<210> SEQ ID NO 456
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 456
aagaugugau cuaaucacag u                                              21

<210> SEQ ID NO 457
<211> LENGTH: 21
<212> TYPE: RNA
<213> ORGANISM: Artificial Sequence
<220> FEATURE:
```

```
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 457
acuuuaaaca gcaccauucu c                                              21

<210> SEQ ID NO 458
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 458
auuacuacau ccaaauccau a                                              21

<210> SEQ ID NO 459
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 459
ucuucuggaa uaacaucauc u                                              21

<210> SEQ ID NO 460
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 460
acuccgcauu acuacaucca a                                              21

<210> SEQ ID NO 461
<211> LENGTH: 21
<212> TYPE: RNA
<213> ORGANISM: Artificial Sequence
```

```
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 461
aacuugaucg uacugacuuc c                                           21

<210> SEQ ID NO 462
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 462
auaaucuaug auuaauacac u                                           21

<210> SEQ ID NO 463
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 463
acauaaacac uucgauucca u                                           21

<210> SEQ ID NO 464
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 464
uccagaagaa uauuggaagg u                                           21

<210> SEQ ID NO 465
<211> LENGTH: 21
<212> TYPE: RNA
```

<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 465 ugagcuaga aaugaauuua a                                          21

<210> SEQ ID NO 466
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 466
uguuaguuga ucaaauacac u                                         21

<210> SEQ ID NO 467
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 467
uuuaacauga uauuucaaac a                                         21

<210> SEQ ID NO 468
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 468
aaugucuccu uucagaacag u                                         21

<210> SEQ ID NO 469
<211> LENGTH: 21

```
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 469
uggaauaaca ucaucuaaua c                                              21

<210> SEQ ID NO 470
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 470
aucagguauu acaaggaugc a                                              21

<210> SEQ ID NO 471
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 471
ugcacauggu gucugggcga g                                              21

<210> SEQ ID NO 472
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 472
ucuauguuca gacauaguac a                                              21

<210> SEQ ID NO 473
```

```
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 473
uuuacaggga ugugacuuua a                                              21

<210> SEQ ID NO 474
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 474
gauucggaaa cugaagaccu g                                              21

<210> SEQ ID NO 475
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 475
ugaacacuau acacccuuuu g                                              21

<210> SEQ ID NO 476
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 476
aggucuuuca aguccucugc a                                              21
```

```
-continued

<210> SEQ ID NO 477
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 477
cuuaggauca gcaccuucuu u                                             21

<210> SEQ ID NO 478
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 478
auauaucuua aauagaggag g                                             21

<210> SEQ ID NO 479
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 479
agcgacaaua gaccacaggg g                                             21

<210> SEQ ID NO 480
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 480
agaacgguca gauuagcucc u                                             21
```

<210> SEQ ID NO 481
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 481
ucagagcgga caucauaucc u                                              21

<210> SEQ ID NO 482
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 482
uguauauauc uuaaauagag g                                              21

<210> SEQ ID NO 483
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 483
aagcucuucu cacucaagcc c                                              21

<210> SEQ ID NO 484
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 484
auuuacaggg augugacuuu a                                              21

```
<210> SEQ ID NO 485
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 485
ucauauccuu gucgugaugc g                                                   21

<210> SEQ ID NO 486
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 486
aucaucacau ccuagauuua u                                                   21

<210> SEQ ID NO 487
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 487
uacugacuuc cacauuucau g                                                   21

<210> SEQ ID NO 488
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 488
```
auuucuucug gaauaacauc a                                             21

<210> SEQ ID NO 489
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 489
agagcggaca ucauauccuu g                                             21

<210> SEQ ID NO 490
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 490
ugcagugaaa ucccaguguu g                                             21

<210> SEQ ID NO 491
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 491
uuacccugca ugcugcugac g                                             21

<210> SEQ ID NO 492
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 492 uaaguggu uu agugcuuuca c                                              21

<210> SEQ ID NO 493
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 493
ucuagaaaug aauuuaagau g                                               21

<210> SEQ ID NO 494
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 494
auccaaaucc auaagaaguu g                                               21

<210> SEQ ID NO 495
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 495
acagcagaga aacagauucc u                                               21

<210> SEQ ID NO 496
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

```
<400> SEQUENCE: 496
uccagugugc uugaaccacu c                                              21

<210> SEQ ID NO 497
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 497
uuugcccacu ugguuugugg a                                              21

<210> SEQ ID NO 498
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 498
ucugcaguga aaucccagug u                                              21

<210> SEQ ID NO 499
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 499
acaaacauag caugcgaccu c                                              21

<210> SEQ ID NO 500
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"
```

```
<400> SEQUENCE: 500
uguucagaca uaguacauuc a                                              21

<210> SEQ ID NO 501
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 501
ucaucuaaua cacuauauac a                                              21

<210> SEQ ID NO 502
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 502
agcucuucuc acucaagccc g                                              21

<210> SEQ ID NO 503
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 503
accaaucuua uugcacaugg u                                              21

<210> SEQ ID NO 504
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
```

<223> OTHER INFORMATION: /ncRNA_class="siRNA"

<400> SEQUENCE: 504
aaucacuacu ccgcauuacu a                                             21

<210> SEQ ID NO 505
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 505
ucguaaggca caaguugaca a                                             21

<210> SEQ ID NO 506
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 506
uggauaagga aaucggccug u                                             21

<210> SEQ ID NO 507
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 507
ucugcaauuu acagggaugu g                                             21

<210> SEQ ID NO 508
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA

```
<222> LOCATION: 1..21
<223> OTHER INFORMATION: /ncRNA_class="siRNA"

<400> SEQUENCE: 508
ucggaaacug aagaccugga c                                              21

<210> SEQ ID NO 509
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 509
ucaaagagau aaucacuuuu g                                              21

<210> SEQ ID NO 510
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 510
uccuccuuug ucucccagcu c                                              21

<210> SEQ ID NO 511
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 511
uaccacaucg gcugggcccc a                                              21

<210> SEQ ID NO 512
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
```

```
<221> NAME/KEY: ncRNA
<222> LOCATION: 1..21
<223> OTHER INFORMATION: /ncRNA_class="siRNA"

<400> SEQUENCE: 512
uauuuccacu ucuguccaga a                                              21

<210> SEQ ID NO 513
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 513
auacagacau gauggaaacg a                                              21

<210> SEQ ID NO 514
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 514
aacagaauau cacaucagua a                                              21

<210> SEQ ID NO 515
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 515
acaguugcua aagugauuuu g                                              21

<210> SEQ ID NO 516
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
```

-continued

<220> FEATURE:
<221> NAME/KEY: ncRNA
<222> LOCATION: 1..21
<223> OTHER INFORMATION: /ncRNA_class="siRNA"

<400> SEQUENCE: 516
aggaacaucc cugcuaacug u                                              21

<210> SEQ ID NO 517
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 517
agcaccuucu uugacaagug g                                              21

<210> SEQ ID NO 518
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 518
auugccuucu uaugugguca u                                              21

<210> SEQ ID NO 519
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 519
uaaacuccuu gcccuuaagu u                                              21

<210> SEQ ID NO 520
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"

```
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 520
aucuuauugc acaugguguc u                                              21

<210> SEQ ID NO 521
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 521
uuucggaucc ucaucugguc c                                              21

<210> SEQ ID NO 522
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 522
cucuuugaac gcaacauggu u                                              21

<210> SEQ ID NO 523
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 523
uacauccaaa uccauaagaa g                                              21

<210> SEQ ID NO 524
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
```

```
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 524
gaaacugaag accuggacca g                                              21

<210> SEQ ID NO 525
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 525
auccacacaa uagaacgguc a                                              21

<210> SEQ ID NO 526
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 526
ugacaaaguu gaugaaacuc g                                              21

<210> SEQ ID NO 527
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 527
agacauagua cauucaucac u                                              21

<210> SEQ ID NO 528
<211> LENGTH: 21
<212> TYPE: RNA
<213> ORGANISM: Artificial Sequence
<220> FEATURE:
<221> NAME/KEY: source
<222> LOCATION: 1..21
```

-continued

```
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 528
agcaggauga ggucucucug a                                              21

<210> SEQ ID NO 529
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 529
uucaaguccu cugcagugaa a                                              21

<210> SEQ ID NO 530
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 530
ugcaugcugc ugacggccgg g                                              21

<210> SEQ ID NO 531
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 531
ucagauuagc uccuggacag u                                              21

<210> SEQ ID NO 532
<211> LENGTH: 21
<212> TYPE: RNA
<213> ORGANISM: Artificial Sequence
<220> FEATURE:
<221> NAME/KEY: source
```

```
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 532
ucaaacgagg uagacaugag u                                              21

<210> SEQ ID NO 533
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 533
ugcuguagau uugaaaggug g                                              21

<210> SEQ ID NO 534
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 534
uugcuguggu cgaaggcaga c                                              21

<210> SEQ ID NO 535
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 535
aaauuccucc uuugucuccc a                                              21

<210> SEQ ID NO 536
<211> LENGTH: 21
<212> TYPE: RNA
<213> ORGANISM: Artificial Sequence
<220> FEATURE:
```

```
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 536
uuccagugug cuugaaccac u                                              21

<210> SEQ ID NO 537
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 537
uacucagcug cggaggaucu c                                              21

<210> SEQ ID NO 538
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 538
caguaaucua uugcacuugg u                                              21

<210> SEQ ID NO 539
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 539
uaaagauaaa uucauucuaa u                                              21

<210> SEQ ID NO 540
<211> LENGTH: 21
<212> TYPE: RNA
<213> ORGANISM: Artificial Sequence
```

```
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 540
aucguacuga cuuccacauu u                                         21

<210> SEQ ID NO 541
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 541
acagauccaa cagucacccu c                                         21

<210> SEQ ID NO 542
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 542
agagucugau guagcagcga u                                         21

<210> SEQ ID NO 543
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 543
augccgaagu cacagagcuu a                                         21

<210> SEQ ID NO 544
<211> LENGTH: 21
<212> TYPE: RNA
```

```
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 544
caaaguugau gaaacucggg g                                              21

<210> SEQ ID NO 545
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 545
acacuauaua cauauuugua a                                              21

<210> SEQ ID NO 546
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 546
uaaucaauca aggcacauug c                                              21

<210> SEQ ID NO 547
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 547
auuagcuccu ggacagucag a                                              21

<210> SEQ ID NO 548
<211> LENGTH: 21
```

```
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 548
uuggauuaag cgcaagucac a                                              21

<210> SEQ ID NO 549
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 549
acaucuguaa acuuugccuu c                                              21

<210> SEQ ID NO 550
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 550
uaugggcaau cacuacuccg c                                              21

<210> SEQ ID NO 551
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 551
uuaaguuuau aguuuauaau a                                              21

<210> SEQ ID NO 552
```

```
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 552
ugaacguaaa ggcugccguu u                                              21

<210> SEQ ID NO 553
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 553
acaacugaga uuuggucuuu u                                              21

<210> SEQ ID NO 554
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 554
uugggaguga agagccgagc g                                              21

<210> SEQ ID NO 555
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 555
uaaagggaug uuucagaagc u                                              21
```

```
<210> SEQ ID NO 556
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 556
ucuagcaggu gaugaacgua a                                              21

<210> SEQ ID NO 557
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 557
ucagugcuuu gcguuuaccc u                                              21

<210> SEQ ID NO 558
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 558
ugaugaacgu aaaggcugcc g                                              21

<210> SEQ ID NO 559
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 559
ucuaugauua auacacuaaa a                                              21
```

```
<210> SEQ ID NO 560
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 560
uaaauagagg aggaauucaa a                                              21

<210> SEQ ID NO 561
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 561
aagcacaaga uacuuaaaug g                                              21

<210> SEQ ID NO 562
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 562
cugacuucca cauuucauga a                                              21

<210> SEQ ID NO 563
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 563
uacuucuccc uguuagugag u                                              21
```

<210> SEQ ID NO 564
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 564
auuggaaggu uugauaucuc u                                              21

<210> SEQ ID NO 565
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 565
uggugaugga cuacgagagg u                                              21

<210> SEQ ID NO 566
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 566
auacagaucc aacagucacc c                                              21

<210> SEQ ID NO 567
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 567
uugcccacuu gguuugugga c    21

<210> SEQ ID NO 568
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 568
aacacuagcg aauaugagag a    21

<210> SEQ ID NO 569
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 569
agacacagca auacgugcca c    21

<210> SEQ ID NO 570
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 570
aucaaggcac auugcuacua g    21

<210> SEQ ID NO 571
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 571
ucaagcccga guuucuaugu u                                              21

<210> SEQ ID NO 572
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 572
uugauaucuc ugugaauaau u                                              21

<210> SEQ ID NO 573
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 573
ugucuccuuu cagaacagug g                                              21

<210> SEQ ID NO 574
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 574
cacagucaac aacuugaucg u                                              21

<210> SEQ ID NO 575
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 575
uucaaacaag aauacaggau a				21

<210> SEQ ID NO 576
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 576
aauuacucag cugcggagga u				21

<210> SEQ ID NO 577
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 577
uucagacaua guacauucau c				21

<210> SEQ ID NO 578
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 578
auucuguccu gucucuauau u				21

<210> SEQ ID NO 579
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

```
<400> SEQUENCE: 579
uuacuacauc caaauccaua a                                              21

<210> SEQ ID NO 580
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 580
ucccugcuaa cuguaaaggu u                                              21

<210> SEQ ID NO 581
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 581
ucauccuucg uaaggcacaa g                                              21

<210> SEQ ID NO 582
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 582
ucuggaauaa caucaucuaa u                                              21

<210> SEQ ID NO 583
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
```

```
<223> OTHER INFORMATION: /ncRNA_class="siRNA"

<400> SEQUENCE: 583
uguugggagu gaagagccga g                                          21

<210> SEQ ID NO 584
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 584
aaacgaacac caaucuuauu g                                          21

<210> SEQ ID NO 585
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 585
aaucuauugc acuuggugaa g                                          21

<210> SEQ ID NO 586
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 586
uuugaaaggu ggauuugcaa a                                          21

<210> SEQ ID NO 587
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
```

-continued

<222> LOCATION: 1..21
<223> OTHER INFORMATION: /ncRNA_class="siRNA"

<400> SEQUENCE: 587
uaaccagagc ucacaaugua c                                              21

<210> SEQ ID NO 588
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
     /note="siRNA specific for mRNA encoding MKK4"
     /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 588
uauacagaca ugauggaaac g                                              21

<210> SEQ ID NO 589
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
     /note="siRNA specific for mRNA encoding MKK4"
     /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 589
uauuacaagg augcacguuc u                                              21

<210> SEQ ID NO 590
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
     /note="siRNA specific for mRNA encoding MKK4"
     /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 590
gaacggucag auuagcuccu g                                              21

<210> SEQ ID NO 591
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
     /note="siRNA specific for mRNA encoding MKK4"
     /organism="Artificial Sequence"
<220> FEATURE:

<221> NAME/KEY: ncRNA
<222> LOCATION: 1..21
<223> OTHER INFORMATION: /ncRNA_class="siRNA"

<400> SEQUENCE: 591
aacacuucga uuccauguau a                                              21

<210> SEQ ID NO 592
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 592 ucguccugu cucuauauuu u                                               21

<210> SEQ ID NO 593
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 593
aucaaucagg uauuacaagg a                                              21

<210> SEQ ID NO 594
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 594
uacccugcau gcugcugacg g                                              21

<210> SEQ ID NO 595
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"

```
<220> FEATURE:
<221> NAME/KEY: ncRNA
<222> LOCATION: 1..21
<223> OTHER INFORMATION: /ncRNA_class="siRNA"

<400> SEQUENCE: 595
cuacuagaaa ucuuuaucua a                                              21

<210> SEQ ID NO 596
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 596
acauacaugg gagagcuggg a                                              21

<210> SEQ ID NO 597
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 597
auccaacagu cacccucucu g                                              21

<210> SEQ ID NO 598
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 598
aucaggcuug ggaccaaggg g                                              21

<210> SEQ ID NO 599
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
```

```
       /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 599
uguucaccuc uuugaacgca a                                              21

<210> SEQ ID NO 600
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
       /note="siRNA specific for mRNA encoding MKK4"
       /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 600
aagcgcaagu cacauagcga c                                              21

<210> SEQ ID NO 601
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
       /note="siRNA specific for mRNA encoding MKK4"
       /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 601
uugccuucuu auguggucau c                                              21

<210> SEQ ID NO 602
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
       /note="siRNA specific for mRNA encoding MKK4"
       /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 602
cuugaucgua cugacuucca c                                              21

<210> SEQ ID NO 603
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
```

```
       /note="siRNA specific for mRNA encoding MKK4"
       /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 603
uucugcaauu uacagggaug u                                             21

<210> SEQ ID NO 604
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
       /note="siRNA specific for mRNA encoding MKK4"
       /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 604
caugauggaa acgaacacca a                                             21

<210> SEQ ID NO 605
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
       /note="siRNA specific for mRNA encoding MKK4"
       /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 605
aaggucuuuc aaguccucug c                                             21

<210> SEQ ID NO 606
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
       /note="siRNA specific for mRNA encoding MKK4"
       /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 606
cagagcggac aucauauccu u                                             21

<210> SEQ ID NO 607
<211> LENGTH: 21
<212> TYPE: RNA
<213> ORGANISM: Artificial Sequence
<220> FEATURE:
<221> NAME/KEY: source
<222> LOCATION: 1..21
```

```
<223> OTHER INFORMATION: /mol_type="RNA"
     /note="siRNA specific for mRNA encoding MKK4"
     /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 607
uaagcuccuc guccaauuuc u                                              21

<210> SEQ ID NO 608
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
     /note="siRNA specific for mRNA encoding MKK4"
     /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 608
acuuuggaua aggaaaucgg c                                              21

<210> SEQ ID NO 609
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
     /note="siRNA specific for mRNA encoding MKK4"
     /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 609
cucagaauua cucagcugcg g                                              21

<210> SEQ ID NO 610
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
     /note="siRNA specific for mRNA encoding MKK4"
     /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 610
aauguacagu ucuuacacua u                                              21

<210> SEQ ID NO 611
<211> LENGTH: 21
<212> TYPE: RNA
<213> ORGANISM: Artificial Sequence
<220> FEATURE:
<221> NAME/KEY: source
```

```
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 611
agugacccua ugcugagcca g                                      21

<210> SEQ ID NO 612
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 612
augucuccuu ucagaacagu g                                      21

<210> SEQ ID NO 613
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 613
agguauuaca aggaugcacg u                                      21

<210> SEQ ID NO 614
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 614
ucgugaugcg cuugggucua u                                      21

<210> SEQ ID NO 615
<211> LENGTH: 21
<212> TYPE: RNA
<213> ORGANISM: Artificial Sequence
<220> FEATURE:
```

```
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 615
agaagcaguu auguuacuga g                                                     21

<210> SEQ ID NO 616
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 616
aacuucagug cuuugcguuu a                                                     21

<210> SEQ ID NO 617
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 617
caauguacag uucuuacacu a                                                     21

<210> SEQ ID NO 618
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 618
aggaucuccu uucacgacuu g                                                     21

<210> SEQ ID NO 619
<211> LENGTH: 21
<212> TYPE: RNA
<213> ORGANISM: Artificial Sequence
```

```
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 619
aagaagcaaa caacugagau u                                              21

<210> SEQ ID NO 620
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 620
aaauaaggca auaucccugc a                                              21

<210> SEQ ID NO 621
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 621
aguuccauac agauccaaca g                                              21

<210> SEQ ID NO 622
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 622
aaguugacaa aguugaugaa a                                              21

<210> SEQ ID NO 623
<211> LENGTH: 21
<212> TYPE: RNA
```

```
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 623
uucuuaggau cagcaccuuc u                                              21

<210> SEQ ID NO 624
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 624
ucucugaaga gugcaccaua a                                              21

<210> SEQ ID NO 625
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 625
auuauuugcc cacuugguuu g                                              21

<210> SEQ ID NO 626
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 626
auuguuugac aguauuuaug a                                              21

<210> SEQ ID NO 627
<211> LENGTH: 21
```

```
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 627
acaccaaucu uauugcacau g                                            21

<210> SEQ ID NO 628
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 628
cagagaaaca gauuccucuu g                                            21

<210> SEQ ID NO 629
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 629
acucacagug cugcuucacu g                                            21

<210> SEQ ID NO 630
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 630
acaugauauu ucaaacagga a                                            21

<210> SEQ ID NO 631
```

```
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 631
ucacucaagc ccgaguuucu a                                              21

<210> SEQ ID NO 632
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 632
aucuaugauu aauacacuaa a                                              21

<210> SEQ ID NO 633
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 633
ucuuuaucac cuaccacauc g                                              21

<210> SEQ ID NO 634
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 634
augaggucuc ucugaccagc a                                              21
```

```
<210> SEQ ID NO 635
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 635
aauacacuau auacauauuu g                                            21

<210> SEQ ID NO 636
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 636
aaacagcacc auucucccuu u                                            21

<210> SEQ ID NO 637
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 637
caacagaaua ucacaucagu a                                            21

<210> SEQ ID NO 638
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 638
acuugaucgu acugacuucc a                                            21
```

```
<210> SEQ ID NO 639
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 639
ucaugaauau guucaucaca a                                              21

<210> SEQ ID NO 640
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 640
cuucuggaau aacaucaucu a                                              21

<210> SEQ ID NO 641
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 641
ugcugccuac uagaaaucuu u                                              21

<210> SEQ ID NO 642
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 642
uccacuucug uccagaagaa u                                              21
```

<210> SEQ ID NO 643
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 643
uuguaacagu gcugaggguu u                                              21

<210> SEQ ID NO 644
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 644
ucacaguugc uaaagugauu u                                              21

<210> SEQ ID NO 645
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 645
ucguacugac uuccacauuu c                                              21

<210> SEQ ID NO 646
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 646
acacuagcga auaugagaga u                                         21

<210> SEQ ID NO 647
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 647
ucagacauag uacauucauc a                                         21

<210> SEQ ID NO 648
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 648
uggguaagug aagaagcaca a                                         21

<210> SEQ ID NO 649
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 649
aauggguaag ugaagaagca c                                         21

<210> SEQ ID NO 650
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 650
auccuucgua aggcacaagu u                                                          21

<210> SEQ ID NO 651
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 651
uuggugaaga aaguaaauuc c                                                          21

<210> SEQ ID NO 652
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 652
aauaaggcaa uaucccugca c                                                          21

<210> SEQ ID NO 653
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 653
acuagcuacu ucucccuguu a                                                          21

<210> SEQ ID NO 654
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 654
agaggagaca cagcaauacg u                                              21

<210> SEQ ID NO 655
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 655
ucaucaucac auccuagauu u                                              21

<210> SEQ ID NO 656
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 656
aaggcugccg uuucggaucc u                                              21

<210> SEQ ID NO 657
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 657
guagacauga guuccauaca g                                              21

<210> SEQ ID NO 658
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

```
<400> SEQUENCE: 658
uacgucuugc uuccucucag c                                          21

<210> SEQ ID NO 659
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 659
uucucacuca agcccgaguu u                                          21

<210> SEQ ID NO 660
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 660
uccuggacag ucagaauugc u                                          21

<210> SEQ ID NO 661
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 661
auugcacaug gugucugggc g                                          21

<210> SEQ ID NO 662
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
```

```
<223> OTHER INFORMATION: /ncRNA_class="siRNA"

<400> SEQUENCE: 662
aggugaugaa cguaaaggcu g                                              21

<210> SEQ ID NO 663
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 663
ucuaauuuaa caugauauuu c                                              21

<210> SEQ ID NO 664
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 664
uucaguccug gugguuugug g                                              21

<210> SEQ ID NO 665
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 665
aaguaucagg cuugggacca a                                              21

<210> SEQ ID NO 666
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
```

```
<222> LOCATION: 1..21
<223> OTHER INFORMATION: /ncRNA_class="siRNA"

<400> SEQUENCE: 666
augugacuuu aaacagcacc a                                              21

<210> SEQ ID NO 667
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 667
acaauguaca guucuuacac u                                              21

<210> SEQ ID NO 668
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 668
aagcucggcc ucucgcacgg c                                              21

<210> SEQ ID NO 669
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 669
gcuacuagcu acuucuccu g                                               21

<210> SEQ ID NO 670
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
```

```
<221> NAME/KEY: ncRNA
<222> LOCATION: 1..21
<223> OTHER INFORMATION: /ncRNA_class="siRNA"

<400> SEQUENCE: 670
uaucuuaaau agaggaggaa u                                              21

<210> SEQ ID NO 671
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 671
ucaaucaagg cacauugcua c                                              21

<210> SEQ ID NO 672
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 672
acaucauauc cuugucguga u                                              21

<210> SEQ ID NO 673
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 673
aucccugcua acuguaaagg u                                              21

<210> SEQ ID NO 674
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
```

```
<220> FEATURE:
<221> NAME/KEY: ncRNA
<222> LOCATION: 1..21
<223> OTHER INFORMATION: /ncRNA_class="siRNA"

<400> SEQUENCE: 674
ucuuuaucua aucaaucaag g                                              21

<210> SEQ ID NO 675
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 675
uucguaaggc acaaguugac a                                              21

<210> SEQ ID NO 676
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 676
caacuugauc guacugacuu c                                              21

<210> SEQ ID NO 677
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 677
acaucaucua auacacuaua u                                              21

<210> SEQ ID NO 678
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
```

```
              /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 678
uaauaaacuc cuugcccuua a                                              21

<210> SEQ ID NO 679
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 679
aacuguaaag caacagaaua u                                              21

<210> SEQ ID NO 680
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 680
agcaguuaug uuacugagcu c                                              21

<210> SEQ ID NO 681
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 681
uaauaaagau acauuguaau a                                              21

<210> SEQ ID NO 682
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
```

```
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 682
uucaccucuu ugaacgcaac a                                              21

<210> SEQ ID NO 683
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 683
aacggucaga uuagcuccug g                                              21

<210> SEQ ID NO 684
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 684
acucauacaa ugugaucccc a                                              21

<210> SEQ ID NO 685
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 685
aaagccuaag guucagugcc a                                              21

<210> SEQ ID NO 686
<211> LENGTH: 21
<212> TYPE: RNA
<213> ORGANISM: Artificial Sequence
<220> FEATURE:
<221> NAME/KEY: source
<222> LOCATION: 1..21
```

```
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 686
agauccaaca gucacccucu c                                              21

<210> SEQ ID NO 687
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 687
acagugcugc uucacuguca u                                              21

<210> SEQ ID NO 688
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 688
ucaggcuugg gaccaagggg a                                              21

<210> SEQ ID NO 689
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 689
uacaaagccu aagguucagu g                                              21

<210> SEQ ID NO 690
<211> LENGTH: 21
<212> TYPE: RNA
<213> ORGANISM: Artificial Sequence
<220> FEATURE:
<221> NAME/KEY: source
```

```
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 690
aucacuacuc cgcauuacua c                                              21

<210> SEQ ID NO 691
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 691
agcagcgaua ucaaucgaca u                                              21

<210> SEQ ID NO 692
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 692
uccuugucgu gaugcgcuug g                                              21

<210> SEQ ID NO 693
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 693
auggacuacg agagguucua g                                              21

<210> SEQ ID NO 694
<211> LENGTH: 21
<212> TYPE: RNA
<213> ORGANISM: Artificial Sequence
<220> FEATURE:
```

```
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 694
acauuucaug aauauguuca u                                              21

<210> SEQ ID NO 695
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 695
acaccgaauu cugagaauga a                                              21

<210> SEQ ID NO 696
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 696
ugcuugaacc acucacagug c                                              21

<210> SEQ ID NO 697
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 697
gaagaaagua aauuccuccu u                                              21

<210> SEQ ID NO 698
<211> LENGTH: 21
<212> TYPE: RNA
<213> ORGANISM: Artificial Sequence
```

```
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 698
accucuuuga acgcaacaug g                                          21

<210> SEQ ID NO 699
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 699
aaacugaaga ccuggaccag u                                          21

<210> SEQ ID NO 700
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 700
gugugcuuga accacucaca g                                          21

<210> SEQ ID NO 701
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 701
caaguugaca aaguugauga a                                          21

<210> SEQ ID NO 702
<211> LENGTH: 21
<212> TYPE: RNA
```

-continued

```
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 702
aucccugcac auuagcuuuu u                                              21

<210> SEQ ID NO 703
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 703
aauaaagaua cauuguaaua a                                              21

<210> SEQ ID NO 704
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 704
ugacaguauu uaugacuguc a                                              21

<210> SEQ ID NO 705
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 705
ccuacuagaa aucuuuaucu a                                              21

<210> SEQ ID NO 706
<211> LENGTH: 21
```

```
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 706
aucacaucag uaaucuauug c                                              21

<210> SEQ ID NO 707
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 707
ucuuuacguc uugcuuccuc u                                              21

<210> SEQ ID NO 708
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 708
uauaauaauc uaugauuaau a                                              21

<210> SEQ ID NO 709
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 709
aaaucuuuau cuaaucaauc a                                              21

<210> SEQ ID NO 710
```

```
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 710
uuccauguau auacuuaaa u                                              21

<210> SEQ ID NO 711
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 711
uccauacaga uccaacaguc a                                             21

<210> SEQ ID NO 712
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 712
uguaugggca aucacuacuc c                                             21

<210> SEQ ID NO 713
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 713
aggauuugga agucugacaa a                                             21
```

-continued

```
<210> SEQ ID NO 714
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 714
ugauauuuca aacaggaaau u                                              21

<210> SEQ ID NO 715
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 715
cuuguaacag ugcugagggu u                                              21

<210> SEQ ID NO 716
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 716
gaauucugca auuuacaggg a                                              21

<210> SEQ ID NO 717
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 717
ggacaucaua uccuugucgu g                                              21
```

```
<210> SEQ ID NO 718
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 718
agcuuaauau uccacuucu g                                              21

<210> SEQ ID NO 719
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 719
auauuuccac uucuguccag a                                             21

<210> SEQ ID NO 720
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 720
uccaggauuu ggaagucuga c                                             21

<210> SEQ ID NO 721
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 721
cuucacuguc auacaaagcc u                                             21
```

<210> SEQ ID NO 722
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 722
cagugcuuug cguuuacccu g                                              21

<210> SEQ ID NO 723
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 723
auguuacuga gcuccauuuu u                                              21

<210> SEQ ID NO 724
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 724
cuugaaccac ucacagugcu g                                              21

<210> SEQ ID NO 725
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 725
uguuugacag uauuuaugac u                                                 21

<210> SEQ ID NO 726
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 726
gucauccaca caauagaacg g                                                 21

<210> SEQ ID NO 727
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 727
acugaugccg aagucacaga g                                                 21

<210> SEQ ID NO 728
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 728
uugucuccca gcuccagaag g                                                 21

<210> SEQ ID NO 729
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 729
ugucgugaug cgcuuggguc u                                           21

<210> SEQ ID NO 730
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 730 auuccacuu cuguccagaa g                                            21

<210> SEQ ID NO 731
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 731
uuccacauuu caugaauaug u                                           21

<210> SEQ ID NO 732
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 732
aguauuuaug acugcacuc u                                            21

<210> SEQ ID NO 733
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 733
uuccuccuuu gucucccagc u                                              21

<210> SEQ ID NO 734
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 734
agaugugauc uaaucacagu c                                              21

<210> SEQ ID NO 735
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 735
cuccucgucc aauuucucca a                                              21

<210> SEQ ID NO 736
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 736
auuacauaaa cacuucgauu c                                              21

<210> SEQ ID NO 737
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

```
<400> SEQUENCE: 737
uccacaagcu guccacugau g                                              21

<210> SEQ ID NO 738
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 738
cacaucagua aucuauugca c                                              21

<210> SEQ ID NO 739
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 739
aggaucagca ccuucuuuga c                                              21

<210> SEQ ID NO 740
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 740
aaagagauuc ggaaacugaa g                                              21

<210> SEQ ID NO 741
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
```

```
<223> OTHER INFORMATION: /ncRNA_class="siRNA"

<400> SEQUENCE: 741
aaggaugcac guucuaggug a                                              21

<210> SEQ ID NO 742
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 742
auuggauuaa gcgcaaguca c                                              21

<210> SEQ ID NO 743
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 743
aaccuugcug uagauuugaa a                                              21

<210> SEQ ID NO 744
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 744
uugcuuccuc ucagcccuuu u                                              21

<210> SEQ ID NO 745
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
```

```
<222> LOCATION: 1..21
<223> OTHER INFORMATION: /ncRNA_class="siRNA"

<400> SEQUENCE: 745
acuguugacc gaauucuuuu a                                              21

<210> SEQ ID NO 746
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 746
gugaacacua uacacccuuu u                                              21

<210> SEQ ID NO 747
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 747
auucuaauuu aacaugauau u                                              21

<210> SEQ ID NO 748
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 748
gucuccuuuc agaacagugg g                                              21

<210> SEQ ID NO 749
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
```

```
<221> NAME/KEY: ncRNA
<222> LOCATION: 1..21
<223> OTHER INFORMATION: /ncRNA_class="siRNA"

<400> SEQUENCE: 749
auaagcuccu cguccaauuu c                                               21

<210> SEQ ID NO 750
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 750
uuacagggau gugacuuuaa a                                               21

<210> SEQ ID NO 751
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 751
auagaacuau uacauaaaca c                                               21

<210> SEQ ID NO 752
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 752
aaaugaggca aguagaucaa a                                               21

<210> SEQ ID NO 753
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
```

```
<220> FEATURE:
<221> NAME/KEY: ncRNA
<222> LOCATION: 1..21
<223> OTHER INFORMATION: /ncRNA_class="siRNA"

<400> SEQUENCE: 753
ucacaaugua caguucuuac a                                              21

<210> SEQ ID NO 754
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 754
cuaggugaca ggaguauaca g                                              21

<210> SEQ ID NO 755
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 755
cuacuagcua cuucucccug u                                              21

<210> SEQ ID NO 756
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 756
uuuacccugc augcugcuga c                                              21

<210> SEQ ID NO 757
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
```

```
           /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 757
cacauagcga caauagacca c                                              21

<210> SEQ ID NO 758
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 758
ugacuuuaaa cagcaccauu c                                              21

<210> SEQ ID NO 759
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 759
aauggugaug gacuacgaga g                                              21

<210> SEQ ID NO 760
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 760
auuccaugua uauaucuuaa a                                              21

<210> SEQ ID NO 761
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
```

-continued

```
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 761
uguccuucca ggauuuggaa g                                              21

<210> SEQ ID NO 762
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 762
acaaggaugc acguucuagg u                                              21

<210> SEQ ID NO 763
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 763
ugauaucucu gugaauaauu u                                              21

<210> SEQ ID NO 764
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 764
auucaacuuc agugcuuugc g                                              21

<210> SEQ ID NO 765
<211> LENGTH: 21
<212> TYPE: RNA
<213> ORGANISM: Artificial Sequence
<220> FEATURE:
<221> NAME/KEY: source
<222> LOCATION: 1..21
```

```
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 765
aagcaacaga auaucacauc a                                              21

<210> SEQ ID NO 766
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 766
ucagaacagu gggaagucua a                                              21

<210> SEQ ID NO 767
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 767
ugggaaguug acagcagaga a                                              21

<210> SEQ ID NO 768
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 768
auguggucau ccacacaaua g                                              21

<210> SEQ ID NO 769
<211> LENGTH: 21
<212> TYPE: RNA
<213> ORGANISM: Artificial Sequence
<220> FEATURE:
<221> NAME/KEY: source
```

```
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 769
acagucaccc ucucugaaga g                                              21

<210> SEQ ID NO 770
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 770
aacggcacgu ucuucauaca u                                              21

<210> SEQ ID NO 771
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 771
guccucugca gugaaauccc a                                              21

<210> SEQ ID NO 772
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 772
guucagacau aguacauuca u                                              21

<210> SEQ ID NO 773
<211> LENGTH: 21
<212> TYPE: RNA
<213> ORGANISM: Artificial Sequence
<220> FEATURE:
```

```
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 773
acucugagag gagacacagc a                                              21

<210> SEQ ID NO 774
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 774
cuagagucug auguagcagc g                                              21

<210> SEQ ID NO 775
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 775
cuauguucag acauaguaca u                                              21

<210> SEQ ID NO 776
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 776
ugcacuuggu gaagaaagua a                                              21

<210> SEQ ID NO 777
<211> LENGTH: 21
<212> TYPE: RNA
<213> ORGANISM: Artificial Sequence
```

```
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 777
augcacguuc uaggugacag g                                              21

<210> SEQ ID NO 778
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 778
uguaggauug ggauucagag u                                              21

<210> SEQ ID NO 779
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 779
acguucuagg ugacaggagu a                                              21

<210> SEQ ID NO 780
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 780
aagauacauu guaauaaacu c                                              21

<210> SEQ ID NO 781
<211> LENGTH: 21
<212> TYPE: RNA
```

```
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 781
agaguaaacc uugcuguaga u                                              21

<210> SEQ ID NO 782
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 782
gaguauacag acaugaugga a                                              21

<210> SEQ ID NO 783
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 783
ugugaucuaa ucacagucaa c                                              21

<210> SEQ ID NO 784
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 784
aaagggaugu uucagaagcu c                                              21

<210> SEQ ID NO 785
<211> LENGTH: 21
```

```
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 785
agauacauug uaauaaacuc c                                              21

<210> SEQ ID NO 786
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 786
uucucccugu uagugaguua u                                              21

<210> SEQ ID NO 787
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 787
aauagagucc acaagcuguc c                                              21

<210> SEQ ID NO 788
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 788
auagaacggu cagauuagcu c                                              21

<210> SEQ ID NO 789
```

```
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 789
aaacgaggua gacaugaguu c                                              21

<210> SEQ ID NO 790
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 790
caucaguaau cuauugcacu u                                              21

<210> SEQ ID NO 791
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 791 ugcacucug agaggagaca c                                               21

<210> SEQ ID NO 792
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 792
uucuuucagu ccuggugguu u                                              21
```

```
<210> SEQ ID NO 793
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 793
cuuuaucacc uaccacaucg g                                               21

<210> SEQ ID NO 794
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 794
auuucuccaa ggucuuucaa g                                               21

<210> SEQ ID NO 795
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 795
ccaaucuuau ugcacauggu g                                               21

<210> SEQ ID NO 796
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 796
caaggaugca cguucuaggu g                                               21
```

```
<210> SEQ ID NO 797
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 797
guauauaucu uaaauagagg a                                                   21

<210> SEQ ID NO 798
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 798
gugcuugaac cacucacagu g                                                   21

<210> SEQ ID NO 799
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 799
cuugucguga ugcgcuuggg u                                                   21

<210> SEQ ID NO 800
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 800
cuucuuucag uccugguggu u                                                   21
```

<210> SEQ ID NO 801
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 801
gaaaugguga uggacuacga g                                             21

<210> SEQ ID NO 802
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 802
acagugggaa gucuaaaguu u                                             21

<210> SEQ ID NO 803
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 803
cugcaugcug cugacggccg g                                             21

<210> SEQ ID NO 804
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 804
acauucuguc cugucucuau a                                              21

<210> SEQ ID NO 805
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 805
uacaaggaug cacguucuag g                                              21

<210> SEQ ID NO 806
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 806
uaauguucac cucuuugaac g                                              21

<210> SEQ ID NO 807
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 807
agugguuuag ugcuuucaca g                                              21

<210> SEQ ID NO 808
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 808
ucugauguag cagcgauauc a                                              21

<210> SEQ ID NO 809
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 809
aaauccauaa gaaguuguuu u                                              21

<210> SEQ ID NO 810
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 810
guuaguugau caaauacacu a                                              21

<210> SEQ ID NO 811
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 811
aauguucacc ucuuugaacg c                                              21

<210> SEQ ID NO 812
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

```
<400> SEQUENCE: 812
gaauaucaca ucaguaaucu a                                              21

<210> SEQ ID NO 813
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 813
auauuucaaa caggaaauuu g                                              21

<210> SEQ ID NO 814
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 814
uugaaaggug gauuugcaaa a                                              21

<210> SEQ ID NO 815
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 815
gacaaaguug augaaacucg g                                              21

<210> SEQ ID NO 816
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"
```

-continued

<400> SEQUENCE: 816
gacuacgaga gguucuagca g                                              21

<210> SEQ ID NO 817
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 817
aacuccugua ggauugggau u                                              21

<210> SEQ ID NO 818
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 818
agaagcaaac aacugagauu u                                              21

<210> SEQ ID NO 819
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 819
agacaugagu uccauacaga u                                              21

<210> SEQ ID NO 820
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21

-continued

<223> OTHER INFORMATION: /ncRNA_class="siRNA"

<400> SEQUENCE: 820
augaauaugu ucaucacaaa a                                              21

<210> SEQ ID NO 821
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 821
cuugcuguag auuugaaagg u                                              21

<210> SEQ ID NO 822
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 822
gaacacauuc uguccugucu c                                              21

<210> SEQ ID NO 823
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 823
aggaugaggu cucucugacc a                                              21

<210> SEQ ID NO 824
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 824
uacaaguugu uccagauaaa a                                         21

<210> SEQ ID NO 825
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 825
aaauauauag cugcuacaag u                                         21

<210> SEQ ID NO 826
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 826
acaguauuua ugacugucac u                                         21

<210> SEQ ID NO 827
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 827
auugggauuc agaguaaacc u                                         21

<210> SEQ ID NO 828
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:

```
<221> NAME/KEY: ncRNA
<222> LOCATION: 1..21
<223> OTHER INFORMATION: /ncRNA_class="siRNA"

<400> SEQUENCE: 828
guacugacuu ccacauuuca u                                              21

<210> SEQ ID NO 829
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 829
aucaaacgag guagacauga g                                              21

<210> SEQ ID NO 830
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 830
acgagguaga caugaguucc a                                              21

<210> SEQ ID NO 831
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 831
ucuagagucu gauguagcag c                                              21

<210> SEQ ID NO 832
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
```

-continued

<220> FEATURE:
<221> NAME/KEY: ncRNA
<222> LOCATION: 1..21
<223> OTHER INFORMATION: /ncRNA_class="siRNA"

<400> SEQUENCE: 832
ugaugccgaa gucacagagc u                                              21

<210> SEQ ID NO 833
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 833
uucuagguga caggaguaua c                                              21

<210> SEQ ID NO 834
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 834
cucugagagg agacacagca a                                              21

<210> SEQ ID NO 835
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 835
cagagcuuaa uauuuccacu u                                              21

<210> SEQ ID NO 836
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"

```
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 836
caguuuguga acacuauaca c                                              21

<210> SEQ ID NO 837
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 837
aggucucucu gaccagcacu a                                              21

<210> SEQ ID NO 838
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 838
cugcaaugca gcaagcucgg c                                              21

<210> SEQ ID NO 839
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 839
gugaagaagc acaagauacu u                                              21

<210> SEQ ID NO 840
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
```

```
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 840
aaugcagcaa gcucggccuc u                                              21

<210> SEQ ID NO 841
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 841
aaacagauuc cucuugaguc c                                              21

<210> SEQ ID NO 842
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 842
agaucaaaga gauaaucacu u                                              21

<210> SEQ ID NO 843
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 843
ucuaggugac aggaguauac a                                              21

<210> SEQ ID NO 844
<211> LENGTH: 21
<212> TYPE: RNA
<213> ORGANISM: Artificial Sequence
<220> FEATURE:
<221> NAME/KEY: source
<222> LOCATION: 1..21
```

```
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 844
acagauuccu cuugaguccc c                                              21

<210> SEQ ID NO 845
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 845
cuuauugcac auggugucug g                                              21

<210> SEQ ID NO 846
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 846
gacauagagc aaugucuccu u                                              21

<210> SEQ ID NO 847
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 847
agaaaguaaa uuccuccuuu g                                              21

<210> SEQ ID NO 848
<211> LENGTH: 21
<212> TYPE: RNA
<213> ORGANISM: Artificial Sequence
<220> FEATURE:
<221> NAME/KEY: source
```

```
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 848
uccaaaucca uagaaguug u                                                      21

<210> SEQ ID NO 849
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 849
auaucucugu gaauaauuuu c                                                     21

<210> SEQ ID NO 850
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 850
ugcagcaagc ucggccucuc g                                                     21

<210> SEQ ID NO 851
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 851
accagagcuc acaauguaca g                                                     21

<210> SEQ ID NO 852
<211> LENGTH: 21
<212> TYPE: RNA
<213> ORGANISM: Artificial Sequence
<220> FEATURE:
```

```
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 852
cuaaaguuua ggauaccgug g                                              21

<210> SEQ ID NO 853
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 853
ugacuuccac auuucaugaa u                                              21

<210> SEQ ID NO 854
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 854
aauagaacgg ucagauuagc u                                              21

<210> SEQ ID NO 855
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 855
cuguagauuu gaaaggugga u                                              21

<210> SEQ ID NO 856
<211> LENGTH: 21
<212> TYPE: RNA
<213> ORGANISM: Artificial Sequence
```

```
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 856
ugcuacaagu uguuccagau a                                              21

<210> SEQ ID NO 857
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 857
caagaagcaa acaacugaga u                                              21

<210> SEQ ID NO 858
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 858
uaaagauaca uuguaauaaa c                                              21

<210> SEQ ID NO 859
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 859
aucccagugu uguucagggg a                                              21

<210> SEQ ID NO 860
<211> LENGTH: 21
<212> TYPE: RNA
```

```
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 860
aagcaguuau guuacugagc u                                              21

<210> SEQ ID NO 861
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 861
caucuaauac acuauauaca u                                              21

<210> SEQ ID NO 862
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 862
ccucucugaa gagugcacca u                                              21

<210> SEQ ID NO 863
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 863
ugcaagcucu ucucacucaa g                                              21

<210> SEQ ID NO 864
<211> LENGTH: 21
```

```
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 864
aauccauaag aaguuguuuu u                                              21

<210> SEQ ID NO 865
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 865
gaaccacuca cagugcugcu u                                              21

<210> SEQ ID NO 866
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 866
aaagcaacag aauaucacau c                                              21

<210> SEQ ID NO 867
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 867
cauagcgaca auagaccaca g                                              21

<210> SEQ ID NO 868
```

-continued

```
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 868
uccauguaua uaucuuaaau a                                              21

<210> SEQ ID NO 869
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 869
aagugacccu augcugagcc a                                              21

<210> SEQ ID NO 870
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 870
augccucuuu aucaccuacc a                                              21

<210> SEQ ID NO 871
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 871
uguggucauc cacacaauag a                                              21
```

```
<210> SEQ ID NO 872
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 872
uauugcacuu ggugaagaaa g                                              21

<210> SEQ ID NO 873
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 873
ucacauccua gauuuauuac a                                              21

<210> SEQ ID NO 874
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 874
uguggucgaa ggcagacaua g                                              21

<210> SEQ ID NO 875
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 875
aaggcacaag uugacaaagu u                                              21
```

```
<210> SEQ ID NO 876
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 876
auccacuguu gaccgaauuc u                                              21

<210> SEQ ID NO 877
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 877
aaggcagaca uagagcaaug u                                              21

<210> SEQ ID NO 878
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 878
uaaggcacaa guugacaaag u                                              21

<210> SEQ ID NO 879
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 879
aagcuccucg uccaauuucu c                                              21
```

<210> SEQ ID NO 880
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 880
aggcacaagu ugacaaaguu g                                              21

<210> SEQ ID NO 881
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 881
ugcaaugcag caagcucggc c                                              21

<210> SEQ ID NO 882
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 882
ucuuucaguc cuggugguuu g                                              21

<210> SEQ ID NO 883
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 883
cuuauguggu cauccacaca a                                                    21

<210> SEQ ID NO 884
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 884
ucucccagcu ccagaaggca a                                                    21

<210> SEQ ID NO 885
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 885
agaaaugaau uuaagaugug a                                                    21

<210> SEQ ID NO 886
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 886
acaauguaug ggcaaucacu a                                                    21

<210> SEQ ID NO 887
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 887
cacauugcua cuagcuacuu c                                              21

<210> SEQ ID NO 888
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 888
ugggucuauu cuuucaggug c                                              21

<210> SEQ ID NO 889
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 889
gaggagacac agcaauacgu g                                              21

<210> SEQ ID NO 890
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 890
aaggaacauc ccugcuaacu g                                              21

<210> SEQ ID NO 891
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

```
<400> SEQUENCE: 891
gaagguuuga uaucucugug a                                              21

<210> SEQ ID NO 892
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 892
gauucagagu aaaccuugcu g                                              21

<210> SEQ ID NO 893
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 893
gaucguacug acuuccacau u                                              21

<210> SEQ ID NO 894
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 894
cuguccagaa gaauauugga a                                              21

<210> SEQ ID NO 895
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"
```

-continued

```
<400> SEQUENCE: 895
ucauccacug uugaccgaau u                                               21

<210> SEQ ID NO 896
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 896
aauaaucuau gauuaauaca c                                               21

<210> SEQ ID NO 897
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 897
cauugcuacu agcuacuucu c                                               21

<210> SEQ ID NO 898
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 898
acaguuugug aacacuauac a                                               21

<210> SEQ ID NO 899
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
```

<223> OTHER INFORMATION: /ncRNA_class="siRNA"

<400> SEQUENCE: 899
acuugguuug uggaccauuu u                                              21

<210> SEQ ID NO 900
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 900
aggcacauug cuacuagcua c                                              21

<210> SEQ ID NO 901
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 901
aauuuaacau gauauuucaa a                                              21

<210> SEQ ID NO 902
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 902
cuugggucua uucuuucagg u                                              21

<210> SEQ ID NO 903
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA

```
<222> LOCATION: 1..21
<223> OTHER INFORMATION: /ncRNA_class="siRNA"

<400> SEQUENCE: 903
auggugaugg acuacgagag g                                              21

<210> SEQ ID NO 904
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 904
aagugguuua gugcuuucac a                                              21

<210> SEQ ID NO 905
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 905
guugacagca gagaaacaga u                                              21

<210> SEQ ID NO 906
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 906
aucaucuaau acacuauaua c                                              21

<210> SEQ ID NO 907
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
```

```
<221> NAME/KEY: ncRNA
<222> LOCATION: 1..21
<223> OTHER INFORMATION: /ncRNA_class="siRNA"

<400> SEQUENCE: 907
gagcaggaug aggucucucu g                                               21

<210> SEQ ID NO 908
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 908
caucauaucc uugucgugau g                                               21

<210> SEQ ID NO 909
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 909
agguuugaua ucucugugaa u                                               21

<210> SEQ ID NO 910
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 910
cagacuccug agucuuccca u                                               21

<210> SEQ ID NO 911
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
```

-continued

```
<220> FEATURE:
<221> NAME/KEY: ncRNA
<222> LOCATION: 1..21
<223> OTHER INFORMATION: /ncRNA_class="siRNA"

<400> SEQUENCE: 911
ucccuguuag ugaguuauga u                                          21

<210> SEQ ID NO 912
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 912
acaucaguaa ucuauugcac u                                          21

<210> SEQ ID NO 913
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 913
aaaguaaauu ccuccuuugu c                                          21

<210> SEQ ID NO 914
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 914
aagauaaauu cauucuaauu u                                          21

<210> SEQ ID NO 915
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
```

```
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 915
uagcuccugg acagucagaa u                                              21

<210> SEQ ID NO 916
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 916
uaaaguauca ggcuugggac c                                              21

<210> SEQ ID NO 917
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 917
cagugugcuu gaaccacuca c                                              21

<210> SEQ ID NO 918
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 918
gugcaagcuc uucucacuca a                                              21

<210> SEQ ID NO 919
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
```

-continued

```
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 919
cauauccuug ucgugaugcg c                                              21

<210> SEQ ID NO 920
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 920
cagauuccuc uugaguccccc g                                             21

<210> SEQ ID NO 921
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 921
aaguuuauag uuuauaauaa u                                              21

<210> SEQ ID NO 922
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 922
acuacgagag guucuagcag g                                              21

<210> SEQ ID NO 923
<211> LENGTH: 21
<212> TYPE: RNA
<213> ORGANISM: Artificial Sequence
<220> FEATURE:
<221> NAME/KEY: source
<222> LOCATION: 1..21
```

```
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 923
ucuaaucaau caaggcacau u                                              21

<210> SEQ ID NO 924
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 924
auuuaagaug ugaucuaauc a                                              21

<210> SEQ ID NO 925
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 925
ugaugcgcuu gggucuauuc u                                              21

<210> SEQ ID NO 926
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 926
caaagcucca agaagcaguu a                                              21

<210> SEQ ID NO 927
<211> LENGTH: 21
<212> TYPE: RNA
<213> ORGANISM: Artificial Sequence
<220> FEATURE:
<221> NAME/KEY: source
```

```
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 927
ugacagcaga gaaacagauu c                                               21

<210> SEQ ID NO 928
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 928
ccucuuugaa cgcaacaugg u                                               21

<210> SEQ ID NO 929
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 929
ugagaggaga cacagcaaua c                                               21

<210> SEQ ID NO 930
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 930
guaaucuauu gcacuuggug a                                               21

<210> SEQ ID NO 931
<211> LENGTH: 21
<212> TYPE: RNA
<213> ORGANISM: Artificial Sequence
<220> FEATURE:
```

```
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 931
aagaagcaca agauacuuaa a                                              21

<210> SEQ ID NO 932
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 932
gauaucucug ugaauaauuu u                                              21

<210> SEQ ID NO 933
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 933
aucuauugca cuuggugaag a                                              21

<210> SEQ ID NO 934
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 934
auauuggaag guuugauauc u                                              21

<210> SEQ ID NO 935
<211> LENGTH: 21
<212> TYPE: RNA
<213> ORGANISM: Artificial Sequence
```

```
-continued

<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 935
gauacauugu aauaaacucc u                                              21

<210> SEQ ID NO 936
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 936
agacaucaga gcggacauca u                                              21

<210> SEQ ID NO 937
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 937
aaaguaucag gcuugggacc a                                              21

<210> SEQ ID NO 938
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 938
auagagcaau gucuccuuuc a                                              21

<210> SEQ ID NO 939
<211> LENGTH: 21
<212> TYPE: RNA
```

```
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 939
cuggacaguc agaauugcuu u                                              21

<210> SEQ ID NO 940
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 940
ccuugguaag gaacaucccu g                                              21

<210> SEQ ID NO 941
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 941
uagcuacuuc ucccuguuag u                                              21

<210> SEQ ID NO 942
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 942
cucuucucac ucaagcccga g                                              21

<210> SEQ ID NO 943
<211> LENGTH: 21
```

```
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 943
auguaugggc aaucacuacu c                                              21

<210> SEQ ID NO 944
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 944
cauuguaaua aacuccuugc c                                              21

<210> SEQ ID NO 945
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 945
cuguaaacuu ugccuucugu a                                              21

<210> SEQ ID NO 946
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 946
cagaaccaua agcuccucgu c                                              21

<210> SEQ ID NO 947
```

```
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 947
aaacuccuug cccuuaaguu u                                           21

<210> SEQ ID NO 948
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 948
aacugaagac cuggaccagu g                                           21

<210> SEQ ID NO 949
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 949
aucgacauac augggagagc u                                           21

<210> SEQ ID NO 950
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 950
uuuccacuuc uguccagaag a                                           21
```

-continued

```
<210> SEQ ID NO 951
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 951
cugaagaccu ggaccaguga u                                                 21

<210> SEQ ID NO 952
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 952
agcuacuucu cccuguuagu g                                                 21

<210> SEQ ID NO 953
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 953
gguauuacaa ggaugcacgu u                                                 21

<210> SEQ ID NO 954
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 954
caaugcagca agcucggccu c                                                 21
```

<210> SEQ ID NO 955
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 955
ugggaagucu aaaguuuagg a                                              21

<210> SEQ ID NO 956
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 956
agaagauagg gaaaugaggc a                                              21

<210> SEQ ID NO 957
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 957
ggaagguuug auaucucugu g                                              21

<210> SEQ ID NO 958
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 958
agauucggaa acugaagacc u                                              21

<210> SEQ ID NO 959
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 959
acauugcuac uagcuacuuc u            21

<210> SEQ ID NO 960
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 960
caguagcugc aucuccaggu u            21

<210> SEQ ID NO 961
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 961
auaucacauc aguaaucuau u            21

<210> SEQ ID NO 962
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 962
aagucacaua gcgacaauag a				21

<210> SEQ ID NO 963
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 963
guaugggcaa ucacuacucc g				21

<210> SEQ ID NO 964
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 964
uggauucauc cuucguaagg c				21

<210> SEQ ID NO 965
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 965
aaguaaauuc cuccuuuguc u				21

<210> SEQ ID NO 966
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 966
auaaagauac auuguaauaa a    21

<210> SEQ ID NO 967
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 967
caugaguucc auacagaucc a    21

<210> SEQ ID NO 968
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 968
acaucaacug uaacuguaaa g    21

<210> SEQ ID NO 969
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 969
cauagcaugc gaccucaacg g    21

<210> SEQ ID NO 970
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 970
aguccacaag cuguccacug a                                              21

<210> SEQ ID NO 971
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 971
acaggaguau acagacauga u                                              21

<210> SEQ ID NO 972
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 972
agaacacauu cuguccuguc u                                              21

<210> SEQ ID NO 973
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 973
ugcgcuuggg ucuauucuuu c                                              21

<210> SEQ ID NO 974
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

```
<400> SEQUENCE: 974
agggauguuu cagaagcucu u                                              21

<210> SEQ ID NO 975
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 975
aagucacaga gcuuaauauu u                                              21

<210> SEQ ID NO 976
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 976
caagcugucc acugaugccg a                                              21

<210> SEQ ID NO 977
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 977
acagaaccau aagcuccucg u                                              21

<210> SEQ ID NO 978
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
```

-continued

<223> OTHER INFORMATION: /ncRNA_class="siRNA"

<400> SEQUENCE: 978
auauuggauu aagcgcaagu c                                           21

<210> SEQ ID NO 979
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 979 ucaucaaag ccuaagguuc a                                            21

<210> SEQ ID NO 980
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 980
uguagauuug aaagguggau u                                           21

<210> SEQ ID NO 981
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 981
uucagugcuu ugcguuuacc c                                           21

<210> SEQ ID NO 982
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 982
auagcugcua caaguuguuc c                                              21

<210> SEQ ID NO 983
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 983
aguaaauucc uccuuugucu c                                              21

<210> SEQ ID NO 984
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 984
cugcagugaa aucccagugu u                                              21

<210> SEQ ID NO 985
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 985
cuguccuguc ucuauauuuu a                                              21

<210> SEQ ID NO 986
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:

<221> NAME/KEY: ncRNA
<222> LOCATION: 1..21
<223> OTHER INFORMATION: /ncRNA_class="siRNA"

<400> SEQUENCE: 986
agagaaacag auuccucuug a                                              21

<210> SEQ ID NO 987
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 987
acugacuucc acauuucaug a                                              21

<210> SEQ ID NO 988
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 988
gacauaguac auucaucacu g                                              21

<210> SEQ ID NO 989
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 989
guccacaagc uguccacuga u                                              21

<210> SEQ ID NO 990
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"

-continued

```
<220> FEATURE:
<221> NAME/KEY: ncRNA
<222> LOCATION: 1..21
<223> OTHER INFORMATION: /ncRNA_class="siRNA"

<400> SEQUENCE: 990
uagggaaaug aggcaaguag a                                              21

<210> SEQ ID NO 991
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 991
acggucagau uagcuccugg a                                              21

<210> SEQ ID NO 992
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 992
agaaaucuuu aucuaaucaa u                                              21

<210> SEQ ID NO 993
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 993
cuuaauauuu ccacuucugu c                                              21

<210> SEQ ID NO 994
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
```

-continued

```
       /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 994
cacaaguuga caaaguugau g                                              21

<210> SEQ ID NO 995
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
       /note="siRNA specific for mRNA encoding MKK4"
       /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 995
cugccuacua gaaaucuuua u                                              21

<210> SEQ ID NO 996
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
       /note="siRNA specific for mRNA encoding MKK4"
       /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 996
acaugaugga aacgaacacc a                                              21

<210> SEQ ID NO 997
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
       /note="siRNA specific for mRNA encoding MKK4"
       /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 997
acuucugucc agaagaauau u                                              21

<210> SEQ ID NO 998
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
```

```
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 998
uuccacuuug gauaaggaaa u                                              21

<210> SEQ ID NO 999
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 999
agauaaauuc auucuaauuu a                                              21

<210> SEQ ID NO 1000
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1000
ggucuuucaa guccucugca g                                              21

<210> SEQ ID NO 1001
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1001
aagagauucg gaaacugaag a                                              21

<210> SEQ ID NO 1002
<211> LENGTH: 21
<212> TYPE: RNA
<213> ORGANISM: Artificial Sequence
<220> FEATURE:
<221> NAME/KEY: source
<222> LOCATION: 1..21
```

```
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1002
guacaguucu uacacuauuu u                                              21

<210> SEQ ID NO 1003
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1003
cauacaaagc cuaagguuca g                                              21

<210> SEQ ID NO 1004
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1004
aauuuacagg gaugugacuu u                                              21

<210> SEQ ID NO 1005
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1005 aguucuaug uucagacaua g                                               21

<210> SEQ ID NO 1006
<211> LENGTH: 21
<212> TYPE: RNA
<213> ORGANISM: Artificial Sequence
<220> FEATURE:
<221> NAME/KEY: source
```

-continued

```
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1006
aggaguauac agacaugaug g                                              21

<210> SEQ ID NO 1007
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1007
aaugaauuua agaugugauc u                                              21

<210> SEQ ID NO 1008
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1008
ggcaauagag uccacaagcu g                                              21

<210> SEQ ID NO 1009
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1009
aacaucccug cuaacuguaa a                                              21

<210> SEQ ID NO 1010
<211> LENGTH: 21
<212> TYPE: RNA
<213> ORGANISM: Artificial Sequence
<220> FEATURE:
```

```
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1010
gugacuuuaa acagcaccau u                                              21

<210> SEQ ID NO 1011
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1011
gacaucauau ccuugucgug a                                              21

<210> SEQ ID NO 1012
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1012
guggucaucc acacaauaga a                                              21

<210> SEQ ID NO 1013
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1013
cagaauuacu cagcugcgga g                                              21

<210> SEQ ID NO 1014
<211> LENGTH: 21
<212> TYPE: RNA
<213> ORGANISM: Artificial Sequence
```

```
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1014
cagacauagu acauucauca c                                           21

<210> SEQ ID NO 1015
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1015
uacagacaaa uaaggcaaua u                                           21

<210> SEQ ID NO 1016
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1016
gcacauugcu acuagcuacu u                                           21

<210> SEQ ID NO 1017
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1017
agacaugaug gaaacgaaca c                                           21

<210> SEQ ID NO 1018
<211> LENGTH: 21
<212> TYPE: RNA
```

<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1018
guagcagcga uaucaaucga c					21

<210> SEQ ID NO 1019
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1019
auguuucaga agcucuuuau a					21

<210> SEQ ID NO 1020
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1020
uagcagcgau aucaaucgac a					21

<210> SEQ ID NO 1021
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1021
agagcuuaau auuuccacuu c					21

<210> SEQ ID NO 1022
<211> LENGTH: 21

```
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1022
ugcccuuaag uuuauaguuu a                                             21

<210> SEQ ID NO 1023
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1023
uguccacuga ugccgaaguc a                                             21

<210> SEQ ID NO 1024
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1024
agagauucgg aaacugaaga c                                             21

<210> SEQ ID NO 1025
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1025
auauuccaaa gcuccaagaa g                                             21

<210> SEQ ID NO 1026
```

```
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1026
caggauuugg aagucugaca a                                         21

<210> SEQ ID NO 1027
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1027
agucacauag cgacaauaga c                                         21

<210> SEQ ID NO 1028
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1028
agaaacagau uccucuugag u                                         21

<210> SEQ ID NO 1029
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1029
uaaauucauu cuaauuuaac a                                         21
```

-continued

```
<210> SEQ ID NO 1030
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1030
aagaagcagu uauguuacug a                                              21

<210> SEQ ID NO 1031
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1031
ugaagaccug gaccagugau g                                              21

<210> SEQ ID NO 1032
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1032
cgagguagac augaguucca u                                              21

<210> SEQ ID NO 1033
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1033
aaccacucac agugcugcuu c                                              21
```

```
<210> SEQ ID NO 1034
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1034
gugacaggag uauacagaca u                                              21

<210> SEQ ID NO 1035
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1035
aucacauccu agauuuauua c                                              21

<210> SEQ ID NO 1036
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1036
caauuuacag ggaugugacu u                                              21

<210> SEQ ID NO 1037
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1037
aacuccuugc ccuuaaguuu a                                              21
```

<210> SEQ ID NO 1038
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
/note="siRNA specific for mRNA encoding MKK4"
/organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1038
cucugaccag cacuaacacu g                                               21

<210> SEQ ID NO 1039
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
/note="siRNA specific for mRNA encoding MKK4"
/organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1039
aucauauccu ugucgugaug c                                               21

<210> SEQ ID NO 1040
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
/note="siRNA specific for mRNA encoding MKK4"
/organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1040
uccacugaug ccgaagucac a                                               21

<210> SEQ ID NO 1041
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
/note="siRNA specific for mRNA encoding MKK4"
/organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1041
gucuauucuu ucaggugcca u                                              21

<210> SEQ ID NO 1042
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1042
uuucuccaag gucuuucaag u                                              21

<210> SEQ ID NO 1043
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1043
agcagagaaa cagauuccuc u                                              21

<210> SEQ ID NO 1044
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1044
auacauggga gagcugggag u                                              21

<210> SEQ ID NO 1045
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1045
acaauagaac ggucagauua g                                                    21

<210> SEQ ID NO 1046
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1046
gucgugaugc gcuugggucu a                                                    21

<210> SEQ ID NO 1047
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1047
caaucuuauu gcacauggug u                                                    21

<210> SEQ ID NO 1048
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1048
agaaauggug auggacuacg a                                                    21

<210> SEQ ID NO 1049
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1049
aacuguaacu guaaagcaac a                                      21

<210> SEQ ID NO 1050
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1050
agugcuuuca caguugcuaa a                                      21

<210> SEQ ID NO 1051
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1051
guaaagauaa auucauucua a                                      21

<210> SEQ ID NO 1052
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1052
caaucgacau acaugggaga g                                      21

<210> SEQ ID NO 1053
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1053
ggaugagguc ucucugacca g                                              21

<210> SEQ ID NO 1054
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1054
auuccaaagc uccaagaagc a                                              21

<210> SEQ ID NO 1055
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1055
caggaguaua cagacaugau g                                              21

<210> SEQ ID NO 1056
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1056
agcucacaau guacaguucu u                                              21

<210> SEQ ID NO 1057
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21

<223> OTHER INFORMATION: /ncRNA_class="siRNA"

<400> SEQUENCE: 1057
acagaauauc acaucaguaa u                                              21

<210> SEQ ID NO 1058
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1058
gagaaacaga uuccucuuga g                                              21

<210> SEQ ID NO 1059
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1059
acaugguguc ugggcgagca a                                              21

<210> SEQ ID NO 1060
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1060
cacuacuccg cauuacuaca u                                              21

<210> SEQ ID NO 1061
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1061
caggugauga acguaaaggc u          21

<210> SEQ ID NO 1062
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1062
uguaaacuuu gccuucugua c          21

<210> SEQ ID NO 1063
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1063
gauaucaauc gacauacaug g          21

<210> SEQ ID NO 1064
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1064
uggucaucca cacaauagaa c          21

<210> SEQ ID NO 1065
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:

```
<221> NAME/KEY: ncRNA
<222> LOCATION: 1..21
<223> OTHER INFORMATION: /ncRNA_class="siRNA"

<400> SEQUENCE: 1065
ugauggacua cgagagguuc u                                      21

<210> SEQ ID NO 1066
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1066
aagagccgag cggcgccgcg g                                      21

<210> SEQ ID NO 1067
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1067
acuuugccuu cuguacuguu u                                      21

<210> SEQ ID NO 1068
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1068
cagcacaccg aauucugaga a                                      21

<210> SEQ ID NO 1069
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
```

```
<220> FEATURE:
<221> NAME/KEY: ncRNA
<222> LOCATION: 1..21
<223> OTHER INFORMATION: /ncRNA_class="siRNA"

<400> SEQUENCE: 1069
aggaauucaa acaagaauac a                                              21

<210> SEQ ID NO 1070
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1070
gacaaauaag gcauauccc u                                               21

<210> SEQ ID NO 1071
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1071
ucuccaaggu cuuucaaguc c                                              21

<210> SEQ ID NO 1072
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1072
gaguccacaa gcuguccacu g                                              21

<210> SEQ ID NO 1073
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
```

```
            /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1073
acugaagacc uggaccagug a                                              21

<210> SEQ ID NO 1074
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1074
aucuaaucac agucaacaac u                                              21

<210> SEQ ID NO 1075
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1075
acuauauaca uauuuguaaa a                                              21

<210> SEQ ID NO 1076
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1076
uccucagaau uacucagcug c                                              21

<210> SEQ ID NO 1077
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
```

```
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1077
gaagauaggg aaaugaggca a                                          21

<210> SEQ ID NO 1078
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1078
cucugcagug aaaucccagu g                                          21

<210> SEQ ID NO 1079
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1079
gaacuauuac auaaacacuu c                                          21

<210> SEQ ID NO 1080
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
        /note="siRNA specific for mRNA encoding MKK4"
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1080
caaacaacug agauuugguc u                                          21

<210> SEQ ID NO 1081
<211> LENGTH: 21
<212> TYPE: RNA
<213> ORGANISM: Artificial Sequence
<220> FEATURE:
<221> NAME/KEY: source
<222> LOCATION: 1..21
```

<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1081
gauuagcucc uggacaguca g                                              21

<210> SEQ ID NO 1082
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1082
uauauuccag ugugcuugaa c                                              21

<210> SEQ ID NO 1083
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1083
cucuuguaac agugcugagg g                                              21

<210> SEQ ID NO 1084
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1084
auagggaaau gaggcaagua g                                              21

<210> SEQ ID NO 1085
<211> LENGTH: 21
<212> TYPE: RNA
<213> ORGANISM: Artificial Sequence
<220> FEATURE:
<221> NAME/KEY: source

```
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1085
uguccagaag aauauuggaa g                                              21

<210> SEQ ID NO 1086
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1086 gcuugcuuc cucucagccc u                                               21

<210> SEQ ID NO 1087
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1087
cuugguuugu ggaccauuuu g                                              21

<210> SEQ ID NO 1088
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1088
augggaaguu gacagcagag a                                              21

<210> SEQ ID NO 1089
<211> LENGTH: 21
<212> TYPE: RNA
<213> ORGANISM: Artificial Sequence
<220> FEATURE:
```

```
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1089
uccagacauc agagcggaca u                                              21

<210> SEQ ID NO 1090
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1090
caauagaguc cacaagcugu c                                              21

<210> SEQ ID NO 1091
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1091
uaaggaacau cccugcuaac u                                              21

<210> SEQ ID NO 1092
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1092
cuuuacgucu ugcuuccucu c                                              21

<210> SEQ ID NO 1093
<211> LENGTH: 21
<212> TYPE: RNA
<213> ORGANISM: Artificial Sequence
```

```
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1093
cuccugaguc uucccauuga a                                            21

<210> SEQ ID NO 1094
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1094
agcaaacaac ugagauuugg u                                            21

<210> SEQ ID NO 1095
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1095
cuacuucucc cuguuaguga g                                            21

<210> SEQ ID NO 1096
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1096
agucuaaagu uuaggauacc g                                            21

<210> SEQ ID NO 1097
<211> LENGTH: 21
<212> TYPE: RNA
```

```
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1097
aauauuggaa gguuugauau c                                              21

<210> SEQ ID NO 1098
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1098
ugaauauguu caucacaaaa g                                              21

<210> SEQ ID NO 1099
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1099
gaaaugaggc aaguagauca a                                              21

<210> SEQ ID NO 1100
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1100
auguucagac auaguacauu c                                              21

<210> SEQ ID NO 1101
<211> LENGTH: 21
```

```
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1101
caucaucaca uccuagauuu a                                       21

<210> SEQ ID NO 1102
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1102
caucuguaaa cuuugccuuc u                                       21

<210> SEQ ID NO 1103
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1103
caaacauagc augcgaccuc a                                       21

<210> SEQ ID NO 1104
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1104
cucacagugc ugcuucacug u                                       21

<210> SEQ ID NO 1105
```

```
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1105
caaggucuuu caaguccucu g                                              21

<210> SEQ ID NO 1106
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1106
cuaauuuaac augauauuuc a                                              21

<210> SEQ ID NO 1107
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1107
acauuguaau aaacuccuug c                                              21

<210> SEQ ID NO 1108
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1108
gaugccgaag ucacagagcu u                                              21
```

-continued

```
<210> SEQ ID NO 1109
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1109
caaugucucc uuucagaaca g                                             21

<210> SEQ ID NO 1110
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1110
agaaccauaa gcuccucguc c                                             21

<210> SEQ ID NO 1111
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1111
guucuagcag gugaugaacg u                                             21

<210> SEQ ID NO 1112
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1112
guaacuguaa agcaacagaa u                                             21
```

<210> SEQ ID NO 1113
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1113
guaagugaag aagcacaaga u                                              21

<210> SEQ ID NO 1114
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1114
aaagcuccaa gaagcaguua u                                              21

<210> SEQ ID NO 1115
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1115
caccauucuc ccuuuauugu u                                              21

<210> SEQ ID NO 1116
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1116
acuccugagu cuucccauug a                                              21

<210> SEQ ID NO 1117
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1117
caaacuccag acaucagagc g                                              21

<210> SEQ ID NO 1118
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1118
auucucccuu uauuguuuga c                                              21

<210> SEQ ID NO 1119
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1119
caccucuuug aacgcaacau g                                              21

<210> SEQ ID NO 1120
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1120
ucaaggcaca uugcuacuag c    21

<210> SEQ ID NO 1121
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1121
cagacauaga gcaaugucuc c    21

<210> SEQ ID NO 1122
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1122
caagaagcag uuauguuacu g    21

<210> SEQ ID NO 1123
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1123
acauccuaga uuuauuacaa c    21

<210> SEQ ID NO 1124
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1124
gaaacgaaca ccaaucuuau u    21

<210> SEQ ID NO 1125
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1125
ugguaaagau aaauucauuc u    21

<210> SEQ ID NO 1126
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1126
ccaacaguca cccucucuga a    21

<210> SEQ ID NO 1127
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1127
cagcagagaa acagauuccu c    21

<210> SEQ ID NO 1128
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

```
<400> SEQUENCE: 1128
caaacgaggu agacaugagu u                                              21

<210> SEQ ID NO 1129
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1129
cuuuauuguu ugacaguauu u                                              21

<210> SEQ ID NO 1130
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1130
auaauaaucu augauuaaua c                                              21

<210> SEQ ID NO 1131
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1131
caaauccaua agaaguuguu u                                              21

<210> SEQ ID NO 1132
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"
```

-continued

<400> SEQUENCE: 1132
ucacuacucc gcauuacuac a                                              21

<210> SEQ ID NO 1133
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1133
acuacaucca aauccauaag a                                              21

<210> SEQ ID NO 1134
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1134
ucagcaccuu cuuugacaag u                                              21

<210> SEQ ID NO 1135
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1135
aguuugugaa cacuauacac c                                              21

<210> SEQ ID NO 1136
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21

<223> OTHER INFORMATION: /ncRNA_class="siRNA"

<400> SEQUENCE: 1136
aacaauguau gggcaaucac u                                          21

<210> SEQ ID NO 1137
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1137
uaggacuggu aaaggagaaa a                                          21

<210> SEQ ID NO 1138
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1138
gcuugaacca cucacagugc u                                          21

<210> SEQ ID NO 1139
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1139
agaugggaag uugacagcag a                                          21

<210> SEQ ID NO 1140
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA

```
<222> LOCATION: 1..21
<223> OTHER INFORMATION: /ncRNA_class="siRNA"

<400> SEQUENCE: 1140
gcagacuccu gagucuuccc a                                              21

<210> SEQ ID NO 1141
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1141
augcgaccuc aacggcacgu u                                              21

<210> SEQ ID NO 1142
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1142
agaauuacuc agcugcggag g                                              21

<210> SEQ ID NO 1143
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1143
ucucucugac cagcacuaac a                                              21

<210> SEQ ID NO 1144
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
```

<221> NAME/KEY: ncRNA
<222> LOCATION: 1..21
<223> OTHER INFORMATION: /ncRNA_class="siRNA"

<400> SEQUENCE: 1144
cugucauaca aagccuaagg u                                              21

<210> SEQ ID NO 1145
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1145
ucugaagagu gcaccauaaa a                                              21

<210> SEQ ID NO 1146
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1146
caaauacacu auuccacuuu g                                              21

<210> SEQ ID NO 1147
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1147
auacaaagcc uaagguucag u                                              21

<210> SEQ ID NO 1148
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"

```
<220> FEATURE:
<221> NAME/KEY: ncRNA
<222> LOCATION: 1..21
<223> OTHER INFORMATION: /ncRNA_class="siRNA"

<400> SEQUENCE: 1148
aacgagguag acaugaguuc c                                              21

<210> SEQ ID NO 1149
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1149
aaagauaaau ucauucuaau u                                              21

<210> SEQ ID NO 1150
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1150
ugaagagccg agcggcgccg c                                              21

<210> SEQ ID NO 1151
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1151
acaaguugac aaaguugaug a                                              21

<210> SEQ ID NO 1152
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
```

```
        /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1152
ccuucuuaug uggucaucca c                                                  21

<210> SEQ ID NO 1153
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1153
acuucucccu guuagugagu u                                                  21

<210> SEQ ID NO 1154
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1154
agcccgaguu ucuauguuca g                                                  21

<210> SEQ ID NO 1155
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1155
gacaggagua uacagacaug a                                                  21

<210> SEQ ID NO 1156
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
```

```
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1156
ugaaaggugg auuugcaaaa u                                               21

<210> SEQ ID NO 1157
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1157
guuccauaca gauccaacag u                                               21

<210> SEQ ID NO 1158
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1158
cugauguagc agcgauauca a                                               21

<210> SEQ ID NO 1159
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1159
aaggcaauau cccugcacau u                                               21

<210> SEQ ID NO 1160
<211> LENGTH: 21
<212> TYPE: RNA
<213> ORGANISM: Artificial Sequence
<220> FEATURE:
<221> NAME/KEY: source
<222> LOCATION: 1..21
```

```
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1160
cugcuaacug uaaagguuuu u                                              21

<210> SEQ ID NO 1161
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1161
gacaguauuu augacuguca c                                              21

<210> SEQ ID NO 1162
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1162
ccacuguuga ccgaauucuu u                                              21

<210> SEQ ID NO 1163
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1163
cuccuuucag aacaguggga a                                              21

<210> SEQ ID NO 1164
<211> LENGTH: 21
<212> TYPE: RNA
<213> ORGANISM: Artificial Sequence
<220> FEATURE:
<221> NAME/KEY: source
```

```
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1164
auucugcaau uuacagggau g                                              21

<210> SEQ ID NO 1165
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1165
guaaaccuug cuguagauuu g                                              21

<210> SEQ ID NO 1166
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1166
agagguucua gcaggugaug a                                              21

<210> SEQ ID NO 1167
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1167
uccaaagcuc caagaagcag u                                              21

<210> SEQ ID NO 1168
<211> LENGTH: 21
<212> TYPE: RNA
<213> ORGANISM: Artificial Sequence
<220> FEATURE:
```

```
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1168
caacaacuug aucguacuga c                                              21

<210> SEQ ID NO 1169
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1169
guuugugaac acuauacacc c                                              21

<210> SEQ ID NO 1170
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1170
agacuccuga gucuucccau u                                              21

<210> SEQ ID NO 1171
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1171
cgcuuggguc uauucuuuca g                                              21

<210> SEQ ID NO 1172
<211> LENGTH: 21
<212> TYPE: RNA
<213> ORGANISM: Artificial Sequence
```

```
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1172
cuugcuuccu cucagcccuu u                                          21

<210> SEQ ID NO 1173
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1173
gaaccauaag cuccucgucc a                                          21

<210> SEQ ID NO 1174
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1174
ucuuaaauag aggaggaauu c                                          21

<210> SEQ ID NO 1175
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1175
augauauuuc aaacaggaaa u                                          21

<210> SEQ ID NO 1176
<211> LENGTH: 21
<212> TYPE: RNA
```

-continued

```
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1176
agagcucaca auguacaguu c                                              21

<210> SEQ ID NO 1177
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1177
uuacucagcu gcggaggauc u                                              21

<210> SEQ ID NO 1178
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1178
acacuauucc acuuuggaua a                                              21

<210> SEQ ID NO 1179
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1179
cauucugucc ugucucuaua u                                              21

<210> SEQ ID NO 1180
<211> LENGTH: 21
```

```
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1180
ccagugugcu ugaaccacuc a                                        21

<210> SEQ ID NO 1181
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1181
gaagcaaaca acugagauuu g                                        21

<210> SEQ ID NO 1182
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1182
cuuugaacgc aacaugguuu u                                        21

<210> SEQ ID NO 1183
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1183
agaagaauau uggaagguuu g                                        21

<210> SEQ ID NO 1184
```

```
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1184
cagggaugug acuuuaaaca g                                              21

<210> SEQ ID NO 1185
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1185
auaggacugg uaaaggagaa a                                              21

<210> SEQ ID NO 1186
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1186
aaauggugau ggacuacgag a                                              21

<210> SEQ ID NO 1187
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1187
agaguccaca agcuguccac u                                              21
```

```
<210> SEQ ID NO 1188
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1188
agcgaauaug agagauuugg g                                           21

<210> SEQ ID NO 1189
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1189
ccuugucgug augcgcuugg g                                           21

<210> SEQ ID NO 1190
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1190
uguuucagaa gcucuuuaua c                                           21

<210> SEQ ID NO 1191
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1191
gagcuuaaua uuuccacuuc u                                           21
```

```
<210> SEQ ID NO 1192
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1192
cacaauagaa cggucagauu a                                              21

<210> SEQ ID NO 1193
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1193
augcugcuga cggccgggug g                                              21

<210> SEQ ID NO 1194
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1194
ucucacucaa gcccgaguuu c                                              21

<210> SEQ ID NO 1195
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1195
aggaggaauu caaacaagaa u                                              21
```

<210> SEQ ID NO 1196
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1196
cacauucugu ccugucucua u                                              21

<210> SEQ ID NO 1197
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1197
ugccgaaguc acagagcuua a                                              21

<210> SEQ ID NO 1198
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1198
acagagcuua auauuuccac u                                              21

<210> SEQ ID NO 1199
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
      /note="siRNA specific for mRNA encoding MKK4"
      /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1199
cagagcucac aauguacagu u 21

<210> SEQ ID NO 1200
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1200
auguagcagc gauaucaauc g 21

<210> SEQ ID NO 1201
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1201
guaauaaacu ccuugcccuu a 21

<210> SEQ ID NO 1202
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1202
acacaauaga acggucagau u 21

<210> SEQ ID NO 1203
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="RNA"
    /note="siRNA specific for mRNA encoding MKK4"
    /organism="Artificial Sequence"
<220> FEATURE:
<221> NAME/KEY: ncRNA
<222> LOCATION: 1..21
<223> OTHER INFORMATION: /ncRNA_class="siRNA"

<400> SEQUENCE: 1203

| | |
|---|---|
| cacagugcug cuucacuguc a | 21 |

<210> SEQ ID NO 1204
<211> LENGTH: 3752
<212> TYPE: RNA
<213> ORGANISM: Homo sapiens
<220> FEATURE:
<221> NAME/KEY: source
<222> LOCATION: 1..3752
<223> OTHER INFORMATION: /mol_type="mRNA"
    /organism="Homo sapiens"
<220> FEATURE:
<221> NAME/KEY: mRNA
<222> LOCATION: 1..3752
<223> OTHER INFORMATION: /gene="mitogen-activated protein kinase
    kinase 4"

<400> SEQUENCE: 1204

| | |
|---|---|
| ggccgugcga gaggccgagc uugcugcauu gcagccgccg cggcgccgcu cggcucuuca | 60 |
| cucccaacaa uggcggcucc gagcccgagc ggcggcggcg gcuccggggg cggcagcggc | 120 |
| agcggcaccc ccggccccgu agggucccecg cgccaggcc acccggccgu cagcagcaug | 180 |
| cagggkuaaac gcaaagcacu gaaguugaau uuugcaaauc caccuuucaa aucuacagca | 240 |
| agguuuacuc ugaaucccaa uccuacagga guucaaaacc cacacauaga gagacugaga | 300 |
| acacacagca uugagucauc aggaaaacug aagaucccc cugaacaaca cugggauuuc | 360 |
| acugcagagg acuugaaaga ccuuggagaa auuggacgag gagcuuaugg uucugucaac | 420 |
| aaaauggucc acaaaccaag ugggcaaaua augcaguua aaagaauucg gucaacagug | 480 |
| gaugaaaaag aacaaaaaca acuucuuaug gauuuggaug uaguaaugcg gaguagugau | 540 |
| ugcccauaca uuguucaguu uuauggugca cucuucagag agggugacug uuggaucugu | 600 |
| auggaacuca ugucuaccuc guuugauaag uuuuacaaau auguauauag uguauuagau | 660 |
| gauguuauuc cagaagaaau uuuaggcaaa aucacuuuag caacugugaa agcacuaaac | 720 |
| cacuuaaaag aaaacuugaa aauuauucac agagauauca aaccuuccaa uauucuucug | 780 |
| gacagaagug gaaauauuaa gcucuguagc uucggcauca guggacagcu uguggacucu | 840 |
| auugccaaga caagagaugc uggcuguagg ccauacaugg caccgaaaag aauagaccca | 900 |
| agcgcaucac gacaaggaua ugauguccgc ucugauguccu ggaguuuggg gaucacauug | 960 |
| uaugaguugg ccacaggccg auuuccuuau ccaaagugga auagguauu ugaucaacua | 1020 |
| acacaagucg ugaaggaga uccuccgcag cugaguaauu cugaggaaag ggaauucucc | 1080 |
| ccgaguuuca ucaacuuugu caacuugugc cuuacgaagg augaauccaa aaggccaaag | 1140 |
| uauaaagagc uucugaaaca ucccuuuauu uugauguaug aagaacgugc cguugagguc | 1200 |
| gcaugcuaug uuuguaaaaau ccuggaucaa augccagcua ucccagcuc ucccauguau | 1260 |
| gucgauugau aucgcugcua caucagacuc uagaaaaag gcugagagg aagcaagacg | 1320 |
| uaaagaauuu ucauccegua ucacaguguu uuauugcuc gcccagacac caugugcaau | 1380 |
| aagauugug uucguuucca ucaugucgu auacuccuug caccuagaac gugcauccuu | 1440 |
| guaauaccug auugaucaca caguguuagu gcuggucaga gagaccucau ccugcucuuu | 1500 |
| ugugaugaac auauucauga aauguggaag ucagacgau caagugugg acugauua | 1560 |
| gaucacaucu uaaauucauu ucuagacuca aaaccuggag augcagcuac uggaauggug | 1620 |
| uuuugucaga cuuccaaauc cuggaaggac acagugauga auguacuaug ucugaacaua | 1680 |
| gaaacucggg cuugagugag aagagcuugc acagccaacg agacacauug ccuucuggag | 1740 |

-continued

```
cugggagaca aaggaggaau uuacuuucuu caccaagugc aauagauuac ugaugugaua    1800
uucuguugcu uuacaguuac aguugauguu uggggaucga ugugcucagc caaauuuccu    1860
guuugaaaua ucauguuaaa uuagaaugaa uuuaucuuua ccaaaaacca uguugcguuc    1920
aaagaggguga acauuaaaau auagagacag gacagaaugu guucuuuucu ccuuuaccag   1980
uccuauuuuu caaugggaag acucaggagu cugccacuug ucaagaagg ugcugauccu     2040
aagaauuuuu cauucucaga auucggugug cugccaacuu gauguccac cugccacaaa    2100
ccaccaggac ugaaagaaga aaacaguaca gaaggcaaag uuuacagaug uuuuaauuc    2160
uaguauuuua ucggaacaa cuuguagcag cuauauauuu ccccuuggu ccaagccuga     2220
uacuuuagcc aucauaacuc acuaacaggg agaaguagcu aguagcaaug ugccuugauu   2280
gauuagauaa agauuucuag uaggcagcaa aagaccaaau cucaguuguu ugcuucuugc   2340
caucacuggu ccaggucuuc aguuuccgaa ucucuuuccc uccccugug gucuauuguc    2400
gcuaugugac uugcgcuuaa uccaauauuu ugccuuuuuu cuauaucaaa aaaccuuuac   2460
aguuagcagg gauguuccuu accaaggauu uuuagccca aaucucucau auucgcuagu    2520
guuuaaaagg cuaagaauag ugggcccag ccgaugggu aggugauaaa gaggcaucuu     2580
uucuagagac acauuggacc agaugaggau ccgaaacggc agccuuuacg uucaucaccu   2640
gcuagaaccu cucguagucc aucaccauuu cuuggcauug gaauucuacu ggaaaaaaau   2700
acaaaaagca aaacaaaacc cucagcacug uuacaagagg ccauuuaagu aucuugugcu   2760
ucuucacuua cccauuagcc agguucucau uagguuuugc uugggccucc cuggcacuga   2820
accuuaggcu uuguaugaca gugaagcagc acugugagug guucaagcac acuggaauau   2880
aaaacaguca uggccugaga ugcaggugau gccauuacag aaccaaaucg uggcacguau   2940
ugcugugucu ccucucagag ugacagucau aaauacuguc aaacaauaaa gggagaaugg   3000
ugcuguuuaa agucacaucc cuguaaauug cagaauucaa aagugauuau cucuuugauc   3060
uacuugccuc auuucccuau cuucuccccc acgguauccu aaacuuuaga cuucccacug   3120
uucugaaagg agacauugcu cuauguccgc cuucgaccac agcaagccau caucuccau    3180
ugcucccggg gacucaagag gaaucuguuu cucugcuguc aacuucccau cuggcucagc   3240
auagggucac uuugccauua ugcaaaugga gauaaaagca auucugacug uccaggagcu   3300
aaucugaccg uucuauugug uggaugacca cauaagaagg caauuuuagu guauuaauca   3360
uagauuauua uaaacuauaa acuuaagggc aaggaguuua uuacaaugua ucuuuauuaa   3420
aacaaagggg uguauagugu ucacaaacug ugaaaauagu guaagaacug uacauuguga   3480
gcucugguua uuuuucucuu guaccauaga aaaauguaua aaaauuauca aaaagcuaau   3540
gugcagggau auugccuuau uugucuguaa aaauggagc ucaguaacau aacugcuucu    3600
uggagcuuug gaauauuuua uccuguauuc uuguuugaau uccuccucua uuuaagauau   3660
auacauggaa ucgaaguguu uauguaauag uucuauccuu ugccugcag gucaguugua   3720
auaaaucuag gaugugauga ugaaaaaaaa aa                                  3752
```